US012052997B2

(12) United States Patent
Slade et al.

(10) Patent No.: US 12,052,997 B2
(45) Date of Patent: Aug. 6, 2024

(54) PLANTS WITH REDUCED LIPASE 1 ACTIVITY

(71) Applicant: ARCADIA BIOSCIENCES, INC., Davis, CA (US)

(72) Inventors: Ann Slade, Davis, CA (US); Michelle Noval, Davis, CA (US); Dayna Loeffler, Davis, CA (US); Jessica Mullenberg, Davis, CA (US); Aaron Holm, Davis, CA (US); Lisa Chambers, Davis, CA (US)

(73) Assignee: ARCADIA BIOSCIENCES, INC., Dallas, TX (US)

( * ) Notice: Subject to any disclaimer, the term of this patent is extended or adjusted under 35 U.S.C. 154(b) by 0 days.

(21) Appl. No.: 17/402,216

(22) Filed: Aug. 13, 2021

(65) Prior Publication Data

US 2022/0039404 A1 Feb. 10, 2022

Related U.S. Application Data

(60) Division of application No. 16/653,288, filed on Oct. 15, 2019, now Pat. No. 11,116,227, which is a continuation of application No. 15/624,974, filed on Jun. 16, 2017, now Pat. No. 10,463,051.

(60) Provisional application No. 62/351,584, filed on Jun. 17, 2016.

(51) Int. Cl.
| | | |
|---|---|---|
| *A01H 5/10* | (2018.01) | |
| *A01H 1/00* | (2006.01) | |
| *A01H 1/04* | (2006.01) | |
| *A01H 1/06* | (2006.01) | |
| *A01H 6/46* | (2018.01) | |
| *A21D 13/06* | (2017.01) | |
| *C12N 9/20* | (2006.01) | |
| *C12N 15/82* | (2006.01) | |
| *C12Q 1/6895* | (2018.01) | |

(52) U.S. Cl.
CPC ............. *A21D 13/06* (2013.01); *A01H 1/045* (2021.01); *A01H 1/06* (2013.01); *A01H 1/104* (2021.01); *A01H 5/10* (2013.01); *A01H 6/4678* (2018.05); *C12N 9/20* (2013.01); *C12N 15/8213* (2013.01); *C12N 15/8242* (2013.01); *C12N 15/8247* (2013.01); *C12N 15/8266* (2013.01); *C12Y 301/01003* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 6,616,957 | B1 * | 9/2003 | Wilhelm | ............... A21D 13/068 426/549 |
| 6,660,915 | B2 | 12/2003 | Douma et al. | |
| 6,696,294 | B1 | 2/2004 | Konzak | |
| 7,897,850 | B2 | 3/2011 | Hirota et al. | |
| 8,455,036 | B2 * | 6/2013 | Haynes | ................... A21D 13/02 426/462 |
| 8,952,216 | B2 | 2/2015 | Spangenberg et al. | |
| 10,087,455 | B2 | 10/2018 | Slade et al. | |
| 10,463,051 | B2 | 11/2019 | Slade et al. | |
| 2003/0166855 | A1 | 9/2003 | Acevedo et al. | |
| 2003/0167544 | A1 | 9/2003 | Douma et al. | |
| 2007/0044171 | A1 | 2/2007 | Kovalic et al. | |
| 2007/0292583 | A1 | 12/2007 | Haynes et al. | |
| 2009/0238935 | A1 | 9/2009 | Haynes et al. | |
| 2013/0276169 | A1 | 10/2013 | Poraty et al. | |
| 2014/0099421 | A1 | 4/2014 | Zhao et al. | |
| 2014/0106052 | A1 | 4/2014 | Hawley et al. | |
| 2014/0130203 | A1 | 5/2014 | La Rosa et al. | |
| 2015/0004301 | A1 | 1/2015 | Arndt et al. | |
| 2017/0044566 | A1 | 2/2017 | Slade et al. | |

FOREIGN PATENT DOCUMENTS

| | | |
|---|---|---|
| CN | 102123598 A | 7/2011 |
| CN | 102925576 A | 2/2013 |
| CN | 103636699 A | 3/2014 |
| JP | 2015192662 A | 11/2015 |
| WO | 2002096190 A2 | 12/2002 |
| WO | 2007149320 A1 | 12/2007 |

(Continued)

OTHER PUBLICATIONS

First Examination Report in Australian Patent Application No. 2017285439 (dated Sep. 15, 2022).
Final Rejection in Japan Patent Application No. 2018566266 and translation (dated Mar. 22, 2022).
Examination Report in European Patent Application EP 17814163.6 (dated Jul. 7, 2022).
Second Office Action in China Patent Application CN201780037253.8 and translation (dated Jun. 28, 2022).
Examination Report in India Patent Application IN201837046411 (dated Sep. 23, 2022).
Office Action in Ukraine Patent Application a201900403 and translation (dated Jul. 13, 2022).

(Continued)

*Primary Examiner* — Phuong T Bui
(74) *Attorney, Agent, or Firm* — Troutman Pepper Hamilton Sanders LLP (Rochester)

(57) ABSTRACT

The disclosure relates to a series of independent human-induced non-transgenic mutations found at one or more of the Lip1 genes of a plant; plants having these mutations in one or more of their Lip1 genes; and a method of creating and finding similar and/or additional mutations of Lip1 by screening pooled and/or individual plants. The plants disclosed herein exhibit decreased lipase activity without having the inclusion of foreign nucleic acids in their genomes. Additionally, products produced from the plants disclosed herein exhibit increased hydrolytic and oxidative stability and increased shelf life without having the inclusion of foreign nucleic acids in their genomes.

9 Claims, 2 Drawing Sheets

Specification includes a Sequence Listing.

(56) References Cited

FOREIGN PATENT DOCUMENTS

| WO | 2012142399 A2 | 10/2012 |
|---|---|---|
| WO | 2017218883 A1 | 12/2017 |

OTHER PUBLICATIONS

Feng et al., "A Secreted Lipase Encoded by LIP1 is Necessary for Efficient Use of Saturated Triglyceride Lipids in Fusarium graminearum," Microbiology 151:3911-3921 (2005).
Office Action in Russian Patent Application No. 2018142860 and translation (mailed Aug. 12, 2021).
Office Action in Chinese Patent Application No. 201780037253.8 and translation (Nov. 3, 2021).
GenBank KC679302.1, Apr. 1, 2014.
Notice of Allowance U.S. Appl. No. 16/653,288 (May 6, 2021).
Office Action in Argentinian Patent Application No. 20170101659 and partial translation (Nov. 10, 2021).
Genbank ADP02185.1, Sep. 7, 2012.
BLAST results of SEQ ID No. 3, Genbank ADP02185.1, Sep. 7, 2012.
GenBank KC679301.1, Apr. 1, 2014.
A0A0D3GUR5_9ORYZ, https://www.uniprot.org/uniprot/A0A0D3GUR5.txt, Retrieved Oct. 14, 2019.
K3ZUR2_SETIT, https://www.uniprot.org/uniprot/K3ZUR2.txt, Retrieved Oct. 14, 2019.
NCBI, GenBank accession No. ADR71857.1, Dec. 9, 2010.
NCBI, GenBank accession No. AHG59317.01 (Apr. 1, 2014).
Extended European Search Report for EP 17814163.6 (Nov. 8, 2019).
International Search Report and Written Opinion of Intl. Appln. No. PCT/US2016/038071, mailed Jan. 4, 2017, 17 pages.
International Preliminary Report on Patentability of Intl. Appln. No. PCT/US2016/038071, mailed Dec. 19, 2017, 11 pages.
International Search Report of Intl. Appln. No. PCT/US2017/37859, mailed Nov. 3, 2017, 4 pages.
Written Opinion of Intl. Appln. No. PCT/US 17137859, mailed Nov. 3, 2017, 4 pages.
International Preliminary Report on Patentability for PCT/US2017/037859 (Dec. 27, 2018).
Office Action in Japanese Patent Application No. 2018-566266 and translation (May 24, 2021).
Office Action in Russian Patent Application No. 2018142860 (Oct. 14, 2020).
Akhter et al., "Inactivation of Lipase Enzyme by Using Chemicals to Maximize Rice Bran Shelf Life and its Edible Oil Recovery," J. Nutr. Food Sci. S12:S12002 (2015).
Almeida et al, Cereal Chemistry 91 (4):321-326, 2014.
Anthon and Barrell, Journal of Agricultural Food Chemistry 49: 32-37, 2001.
Barone, R., 1999. Journal of agricultural and food chemistry, 47(5), pp. 1924-1931.
Barros et al., "Seed lipases: Sources, Applications and Properties—a Review," Brazilian Journal of Chemical Engineering, vol. 27, No. 01, pp. 15-29, Jan.-Mar. 2010.
Borrelli, et al., "Lipoxygenas e in durum wheat: What is the role in Pasta Color?," CIHEAM—Options Mediterraneennes, pp. 497-500 (2000).
Borrelli, et al., Durum Wheat Lipoxygenase Activity and Other Quality Parameters that Affect Pasta Color, Cereal Chemistry, 76(3):335-340 (1999).
Butt, M.S., Nasir, M. and Akhtar, S., Sharifik. 2004. Int. J_ Food Safely, 4, pp. 1-4.
Carrera et al, A Deletion at the Lpx-B1 Locus is Associated with Low Lipoxygenase Activity and Improved Pasta Color in Durum Wheat (Triticum turgidum ssp. durum), Journal of Cereal Science, 45(1):67-77 (2007).
Cato, et al., "Measurement of Lipoxygenase in Australian White Wheat Flour: The Effect of Lipoxygenase on the Quality Properties of White Salted Noodles," Journal of the Science of Food and Agriculture, 86(11 ):1670-1678 (2006).
Chuang et al., "Functional Proteomic Analysis of Rice Bran Esterases/Lipases and Characterization of a Novel Recombinant Esterase," J. Agric. Food Chem., 59(5): 2019-2025 (2011).
De Simone, et al., "Different Mechanisms Control Lipoxygenase Activity in Durum Wheat Kernels," Journal of Cereal Science, 52(2):121-128 (2010).
Doblado-Maldonado, et al., "Key Issues and Challenges in Whole Wheat Flour Milling and Storage," Journal of Cereal Science, 56(2):119-126 (2012).
Doblado-Maldonado, et al., "Effect of Salt Solutions Applied During Wheat Conditioning on Lipase Activity and Lipid Stability of Whole Wheat Flour," Food Chemistry, 140(1-2):204-209 (2013).
Doblado-Maldonado, A.F., "New Technologies for Whole Wheat Processing: Addressing Milling and Storage Issues," Thesis University of Nebraska-Lincoln (2012).
Dong, et al, "Grain-specific Reduction in Lipoxygenase Activity Improves Flour Color Quality and Seed Longevity in Common Wheat," Molecular breeding, 35(7):150 (2015).
P. Eastmond, "Sugar-Dependent1 Encodes a Patatin Domain Triacylglycerol Lipase That Initiates Storage Oil Breakdown in Germinating Arabidopsis SeedsThe Plant Cell," 18:665-675 (2006).
Feng et al, "Molecular Analysis of Lipoxygenase (LOX) Genes in Common Wheat and Phylogenetic Investigation of LOX Proteins From Model and Crop Plants," Journal of Cereal Science, 52(3):387-394 (2010).
Feng et al, "Molecular Characterization of a Novel Type of Lipoxygenase (LOX) Gene From Common Wheat (Triticum aestivum L.)," Molecular Breeding, 30:113-124 (2012).
Fritsch and Gale, "Hexanal as a Measure of Rancidity in Low Fat Foods," JAOCS, 54:225 (1977).
Galliard, T., "Hydrolytic and Oxidative Degradation of Lipids During Storage of Wholemeal Flour: Effects of Bran and Germ Components," Journal of Cereal Science 4(2):179-192 (1986).
Galliard, T., "Oxygen Consumption of Aqueous Suspensions of Wheat Wholemeal, Bran and Germ: Involvement of Lipase and Lipoxygenase," Journal of Cereal Science, 4(1):33-50 (1986).
Galliard, T., Rancidity in Foods, edited by JC Allen and RJ Hamilton (1983).
Garbus, et al., "Physical Mapping of Durum Wheat Lipoxygenase Genes," Journal of Cereal Science, 50:67-73 (2009).
Garbus et al., "Identification, mapping and evolutionary course of wheat lipoxygenase-1 genes located on the A genome," Journal of Cereal Science, 58:298-304 (2013).
Geng et al, Molecular Breeding vol. 28, No. 1, p. 117-126, 2011.
Geng, H., "Development of Functional Markers for a Lipoxygenase Gene TaLox-B1 on Chromosome 4BS in Common Wheat," Crop Science, 52(2):568-576 (2012).
Goesaert, H., "Wheat Flour Constituents: How They Impact Bread Quality, and How to Impact Their Functionality," Trends in food science & technology, 16(1):12-30 (2005).
Goffman and Bergman, "Hydrolytic Degradation of Triacylglycerols and Changes in Fatty Acid Composition in Rice Bran During Storage," Cereal Chem., 80(4):459-461 (2003).
Goutam, et al., "Biotechnological Approaches for Grain Quality Improvement in wheat: Present status and Future Possibilities," Australian Journal of Crop Science, 7(4):469-483 (2013).
Guo, et al., "Rare Allele of HvLox-1 Associated With Lipoxygenase Activity in Barley (Hordeum vulgare L.)," Theor. Appl. Genet., 127(10):2095-2103 (2014).
Hamilton-Kemp, et al., "Effects of Lipoxygenase Inhibitors on the Formation of Volatile Compounds in Wheat," Phytochemistry, 26(5):1273-1277 (1987).
Hessler, T.G., et al., Crop Science, 42(5), Sep. 2002, pp. 1695-1700.
Hidalgo, A. and Brandolini, A., "Lipoxygenase Activity in Wholemeal Flours From Triticum Monococcum, Triticum turgidum and Triticum aestivum," Food Chemistry, 131(4):1499-1503 (2012).
Jakab, G., et al., "Molecular Characterization of a Novel Lipase-Like Pathogen-Inducible Gene Family of Arabidopsis ," Plant Physiology, 132(4):2230-2239 (2003).
Jiang, et al., "Analysis of GDSL Lipase (GLIP) Family Genes in Rice (Oryza sativa)," Plant Omics Journal, 5(4):351-358 (2012).

(56) References Cited

OTHER PUBLICATIONS

Kelly, et al., "Seed Storage Oil Mobilization Is Important but Not Essential for Germination or Seedling Establishment in *Arabidopsis*1," Plant Physiology, 157(2):866-875 (2011).
Leenhardt, et al., "Genetic Variability of Carotenoid Concentration, and Lipoxygenase and Peroxidase Activities Among Cultivated Wheat Species and Bread Wheat Varieties," European Journal of Agronomy, 25(2):170-176 (2006).
Leenhardt, F., et al., "Wheat Lipoxygenase Activity Induces Greater Loss of Carotenoids than Vitamin E during Breadmaking," J. Agric. Food Chem., 54(5):1710-1715 (2006).
Loiseau, J., et al., "Seed Lipoxygenases: Occurrence and Functions," Seed Science Research, 11 (3):199-211 (2001).
Malekian et al., "Lipase and Lipoxygenase Activity, Functionality, and Nutrient Losses in Rice Bran During Storage," Louisiana State University, LSU Digital Commons, LSU Agricultural Experiment Station Reports, Bulletin No. 870, pp. 1-69 (2000).
Manna, et al., "Differential Expression of Lipoxygenase Genes Among Durum Wheat Cultivars," Cereal Research Communications, 26:23-30 (1998).
Marathe, S.A., et al., "Extension of Shelf-life of Whole-Wheat Flour by Gamma Radiation," International Journal of Food Science & Technology, 37(2):pp. 163-168 (2002).
Narvel ,et al, "Agronomic and Seed Traits of Soybean Lines Lacking Seed Lipoxygenases," American Society of Agronomy, 38(4):926-928 (1998).
Nicolas, J., et al., "Purification and some properties of wheat germ lipoxygenase," Journal of the Science of Food and Agriculture, 33(4):pp. 365-372 (1982).
Pico, J., et al., "Wheat bread aroma compounds in crumb and crust: A review," Food Research International, 75:200-215 (2015).
Sharma, S., et al., 2014. Storage Stability and Quality Assessment of Processed Cereal Brans, Journal of Food Science and Technology, 51(3):583-588 (2014).
Shiiba, et al., "Purification and Characterization of Lipoxygenase Isozymes from Wheat Germ," Cereal Chem, 68(2):115-122 (1991).
Shirasawa, et al., "Identification of Gene for Rice (*Oryza sativa*) Seed Lipoxygenase-3 Involved in the Generation of Stale Flavor and Development of SNP Markers for Lipoxygenase-3 Deficiency," Breeding science, 58(2):169-176 (2008).
R. Singh, Dissertation submitted to Jaipur Engineering College and Research Centre, Rajasthan University, Rice Bran Lipase Cloning and Expression, pp. 1-47 (2007).
Surrey, K., "Spectrophotometric Method for Determination of Lipoxidase Activity," Plant Physiology 39(1):65-70 (1964).
Suzuki, et al., "Volatile Components in Stored Rice [*Oryza sativa* (L.)] of Varieties with and without Lipoxygenase-3 in Seeds," J. Agric. Food Chem., 47(3):1119-1124 (1999).
Rose and Pike, "A simple method to measure lipase activity in wheat and wheat bran as an estimation of storage quality," Journal of the American Oil Chemists' Society, 83(5):415-419 (2006).
Umate, P., "Genome-Wide Analysis of Lipoxygenase Gene Family in *Arabidopsis* and Rice," Plant Signaling & Behavior, 6(3):335-338 (2011).
Verlotta ,et al, "Insight Into Durum Wheat Lpx-B1: A Small Gene Family Coding for the Lipoxygenase Responsible for Carotenoid Bleaching in Mature Grains," BMC Plant Biology, 10:263 (2010).
Vijayakumar, et al., "Temporal Expression Profiling of Lipase During Germination and Rice Caryopsis Development," Plant Physiology and Biochemistry, 57:245-253 (2012).
Vijayakumar and Gowda, "Rice (*Oryza sativa*) Lipase: Molecular Cloning, Functional Expression and Substrate Specificity," Protein Expression and Purification, 88(1):67-79 (2013).
Wallace, J.M. and Wheeler, E.L., America Associate of Cereal chemists, pp. 92-98 (1972).
Wang, L. and Flores, R. A., "The effects of storage on flour quality and baking performance," Food Rev. Int., 15(2):215-234 (1999).
Wang et al, Nature Biotechnology, 32(9):947-952 (2014).
Warwick, M., et al., "Changes in Total Fatty Acids and Individual Lipid Classes on Prolonged Storage of Wheat Flour," J. Sci. Food Agric., 30:1131-1138 (1979).
Warwick, M., and Shearer, G., "The Identification and Quantification of Some Non-volatile Oxidation Products of Fatty Acids Developed During Prolonged Storage of Wheat Flour," J. Sci. Food Agric., 31:316-318 (1980).
Wu, P., et al., "The Allelic Variation of Lipoxygenase Genes in Bread Wheat Cultivars from the Yellow and Huai Wheat Areas of China," Scientia Agricultura Sinica, 48(2): 207-214 (2015).
Xu, B., et al., Quality Assurance and Safety of Crops & Foods, 4(1):26-32 (2012).
Xu, B., et al., "Study on the stabilization effect of continuous microwave on wheat germ," Journal of Food Engineering, 117(1):1-7 (2013).
Zhang, et al, "Effect of the absence of lipoxygenase isoenzymes on the storage characteristics of rice grains," J. of Stored Products Research, 43(1):87-91 (2007).
Zhang, W., et al., "QTL analysis of pasta quality using a composite microsatellite and SNP map of durum wheat," Theoretical and Applied Genetics, 117(8):1361-1377 (2008).
Zhang, et al., Journal of Triticeae Crops, 32(4):005 (2012).
Office Action in Mexican Patent Application No. MX/a/2018/015927 and translation (dated Jul. 7, 2021).
Office Action in Russian Patent Application No. 2018142860 and translation (Jan. 26, 2022).
Office Action in Mexican Patent Application No. MX/a/2018/015927 and translation (dated Feb. 1, 2022).
Office Action in Brazil Patent Application BR112018076321-7 and Translation (dated Dec. 4, 2023).
Office Action in Canada Patent Application No. 3026761, dated Jul. 6, 2023.
Akhter et al., "Inactivation of Lipase Enzyme by Using Chemicals to Maximize Rice Bran Shelf Life and its Edible Oil Recovery," Integrative Food, Nutrition and Metabolism, 2(2):166-170 (2015).
Preliminary Office Action in Brazil Patent Application BR112018076321-7 and translation (published Dec. 20, 2022).
I1GRD9_BRADI, https://www.uniprot.org/uniprot/I1GRD9.txt (Jun. 13, 2012).

* cited by examiner

FIG. 1

SEQUENCE LISTING

<160> NUMBER OF SEQ ID NOS: 48

<210> SEQ ID NO 1
<211> LENGTH: 3280
<212> TYPE: DNA
<213> ORGANISM: Triticum aestivum

<400> SEQUENCE: 1

| | | | | | |
|---|---|---|---|---|---|
| atggagcgac | ggaggcgggt | cgccgtgctg | gccctggtgc | tcctgctgct | ctcggcttgt | 60 |
| catggcagaa | gaggtatgac | ctcgattatc | tttctttttt | tttgttgggt | aactgttcta | 120 |
| agttttcctc | aaatgaattc | caagaacgcg | ttaactaatt | cagtagcgat | tgggctgttt | 180 |
| actgaattca | ttctgactgc | catgattgga | gaaagcatag | acgaatatca | gtgcacacgc | 240 |
| aggcatttca | aaggtgtaa | tcatgcaggg | agagaaaggg | ggcagctatg | gcactgacga | 300 |
| aattgccctg | ctccctgtaa | atttccccaa | gttctgattg | cctgttagcc | gcacactggc | 360 |
| ctacaactga | actaattgaa | tgcacttctt | gttgttgtgg | ctggggcctt | ggggggttgta | 420 |
| tccaaacatc | tggagaaagt | tgtaccatct | ttgtgtggac | agaaaaggaa | attaggtggc | 480 |
| tggcagttgg | aacctacctg | gtcccttgtt | aacaaaatga | agttctggtt | gcatatggtt | 540 |
| ggtcacctcc | agaaaataaa | agggttgaat | taagaagaac | gagttgatga | accgtggcgg | 600 |
| caaagaacca | ttgtactgtt | gtggagcttg | acttgctctg | gggattccac | tagcatcacc | 660 |
| catgatgccc | ccaattgatc | tttagctgcc | atatctaagc | attatgttca | gtgattcaca | 720 |
| gcaaagacc | atcatagatt | cttttggagc | ttggcttgac | agatctagtg | cgtgtacaac | 780 |
| atatggcact | taacctaata | ctcctatttg | ataaggcccc | caactgattt | tgtctgtcat | 840 |
| atactcatat | cactgcaata | ttttcagtta | tccacttgct | ctaggtggat | ttgtgatttg | 900 |
| tgaatataag | tggtttcagc | cttcaggaca | tgagaatagg | tgaaattgaa | tcacctatgc | 960 |
| ccttttaact | tggctgtcac | ccgttcatgc | ttaacctctc | ctggtaatta | gaacttagtt | 1020 |
| tgttatatcc | ctcagatatt | atatgcacaa | acttaatcaa | agtgaaattc | tgctaaaagc | 1080 |
| tgccacagat | atgacaggca | aaatcaatt | ggggtcattt | attctgtttg | ctttcagttt | 1140 |
| gttcaatttg | ttttttcttgg | cgcaaatgtt | tgtccatctg | ctttggcatc | ttcttatatc | 1200 |
| tgaaattgat | cttctgcact | tgtgttcagg | attgcatcat | ttataaatatg | ctaataaact | 1260 |
| aactgttttc | attatcgcag | agttctctgt | caagaatcac | gatcagagtc | ttatatatga | 1320 |
| tcatactctt | gctaagacca | ttgtggagta | tgcttcggct | gtaagttaaa | cttatgctca | 1380 |
| ttattgcatt | aagtgcatgt | catgctttct | aaatggagct | ttagttcgtc | tttgtcttga | 1440 |
| gtcttgttaa | gtcaaaatta | actaaatact | gtctgcaggt | gtatatgaca | gatttaacag | 1500 |
| ctttgtatac | atggacatgc | tcaagatgca | atgacttgac | tcaagtaaga | aaccttgcaa | 1560 |
| ctgttctctt | ccattcatat | ctatctaggg | gtgcttattt | gttttcctga | aactatactg | 1620 |
| ttcaaacagt | aagggatcta | tcaagatgct | cgccaatggt | tggttgggtg | tcatatgcag | 1680 |
| ctgcccgaca | actatacagc | ttatagaatc | tgtcctttct | tatttatata | ttcacctact | 1740 |
| tctgaaatag | gacttcgaga | tgaggtctct | aattgttgat | gtggagaact | gcttgcaggt | 1800 |
| tcctatctta | acacactcca | ttttaagttg | tcataaattt | ccggcatatt | tctcatcaag | 1860 |
| tgtactgaac | ttctcatgat | atggccttcc | ttttacctgc | cattctacgg | gtgaacaatg | 1920 |
| tgacaggcat | ttgtcggtgt | agctcacaat | ctaaatgcca | taatagttgc | aatcagaggg | 1980 |
| actcaagaga | acaggtacta | atcaaattgc | atgtgcttct | agtattccca | gttaaaccgg | 2040 |
| tatgctttat | gtgttactat | tctgatttct | tgagtcacat | gtcatttatg | ttttagattt | 2100 |

```
gcttgctcag tgtgcagaat tggatcaagg acttggtatg gaagcagctt gatctaagct    2160
atccagacat gccaaatgca aaggttattg ccaataaact gtttatactt tcttaaaaga    2220
gaaaaggaaa ggcagatgca ccttttttgct aaaagacttt ctactactct ggttaaaggt   2280
gcacagtgga ttttttctcct cctataataa tacaattttg cgtctagcta tcacaagtgc   2340
tgtgcacaac gcaagaaaga catatgggga tatcggtgtc atagtcacag ggcactcaat    2400
gggaggagcc atggctgcct tctgtgcact cgatcttgct gtaagtacac aagatccaat    2460
gtttcacaaa tacattcaat gtccagactc ttaattcctt ccaggttata taaatttcgg    2520
tcttgtttca aattcctaac accagcactc taatatttga ggcttgttat tatgtaagct    2580
gttgattttt ctcttcaaac cctatccaca gatcaagctc ggaagcgaca atgttcaact    2640
catgactttc ggacagcctc gtgttggcaa tgctgttttc gcctcctact ttgccaaata    2700
tgtaccaaac acaattcgac tggtacacgg acatgatatt gtgccgcatt tgccacctta    2760
tttctccttc ctttccaaac tgacgtacca ccacttccca agagaggtac accttgggca    2820
caaacttata aatatgcttt ccaactccta ggaagccttt atcgctgtgt tatgcttagt    2880
gcttgctcat atttaggta tggatcgacg aatctgatgg caacacaacg gaacagatat     2940
gtgatgccag cggcgaagac ccaaactgct gcaggttttt acagagcaca gacctcctgc    3000
agctcaactg cctgtctctt tagctcctag ttctaacatt atccccatct atcgtcttac    3060
taggtgcctc tccatattga gcctgagcat tcaggaccat ttcacatacc tgggagtaga    3120
catgaaatca gatgactgga gcacctgcag aatcatcaca gcacaaagcg ttgagcgatt    3180
acgtaagcat ctcagcagca acatcatcat gacaaagcac gccatcgagg tctccattgt    3240
cgagaatagc atgcagacag actggagcag ttccagatag                          3280

<210> SEQ ID NO 2
<211> LENGTH: 1060
<212> TYPE: DNA
<213> ORGANISM: Triticum aestivum

<400> SEQUENCE: 2
atggagcgac ggaggcgggt cgccgtgctg gccctggtgc tcctgctgct ctcggcttgt      60
catggcagaa gaggagttct ctgtcaagaa tcacgatcag agtcttatat atgatcatac     120
tcttgctaag accattgtgg agtatgcttc ggctgtgtat atgacagatt taacagcttt     180
gtatacatgg acatgctcaa gatgcaatga cttgactcaa gacttcgaga tgaggtctct     240
aattgttgat gtggagaact gcttgcaggc atttgtcggt gtagctcaca atctaaatgc     300
cataatagtt gcaatcagag ggactcaaga gaacagtgtg cagaattgga tcaaggactt     360
ggtatggaag cagcttgatc taagctatcc agacatgcca aatgcaaagg tgcacagtgg     420
atttttctcc tcctataata atacaatttt gcgtctagct atcacaagtg ctgtgcacaa     480
cgcaagaaag acatatgggg atatcggtgt catagtcaca gggcactcaa tgggaggagc     540
catggctgcc ttctgtgcac tcgatcttgc tatcaagctc ggaagcgaca atgttcaact     600
catgactttc ggacagcctc gtgttggcaa tgctgttttc gcctcctact ttgccaaata     660
tgtaccaaac acaattcgac tggtacacgg acatgatatt gtgccgcatt tgccacctta    720
tttctccttc ctttccaaac tgacgtacca ccacttccca agagaggtat ggatcgacga    780
atctgatggc aacacaacgg aacagatatg tgatgccagc ggcgaagacc caaactgctg    840
caggtgcctc tccatattga gcctgagcat tcaggaccat ttcacatacc tgggagtaga    900
```

```
catggaatca gatgactgga gcacctgcag aatcatcaca gcacaaagcg ttgagcgatt    960
acgtaagcat ctcagcagca acatcatcat gacaaagcac gccatcgagg tctccattgt   1020
cgagaatagc atgcagacag actggagcag ttccagatag                         1060
```

<210> SEQ ID NO 3
<211> LENGTH: 352
<212> TYPE: PRT
<213> ORGANISM: Triticum aestivum

<400> SEQUENCE: 3

```
Met Glu Arg Arg Arg Val Ala Val Leu Ala Leu Val Leu Leu
1               5                   10                  15

Leu Ser Ala Cys His Gly Arg Arg Glu Phe Ser Val Lys Asn His Asp
            20                  25                  30

Gln Ser Leu Ile Tyr Asp His Thr Leu Ala Lys Thr Ile Val Glu Tyr
        35                  40                  45

Ala Ser Ala Val Tyr Met Thr Asp Leu Thr Ala Leu Tyr Thr Trp Thr
    50                  55                  60

Cys Ser Arg Cys Asn Asp Leu Thr Gln Asp Phe Glu Met Arg Ser Leu
65                  70                  75                  80

Ile Val Asp Val Glu Asn Cys Leu Gln Ala Phe Val Gly Val Ala His
                85                  90                  95

Asn Leu Asn Ala Ile Ile Val Ala Ile Arg Gly Thr Gln Glu Asn Ser
            100                 105                 110

Val Gln Asn Trp Ile Lys Asp Leu Val Trp Lys Gln Leu Asp Leu Ser
        115                 120                 125

Tyr Pro Asp Met Pro Asn Ala Lys Val His Ser Gly Phe Phe Ser Ser
    130                 135                 140

Tyr Asn Asn Thr Ile Leu Arg Leu Ala Ile Thr Ser Ala Val His Asn
145                 150                 155                 160

Ala Arg Lys Thr Tyr Gly Asp Ile Gly Val Ile Val Thr Gly His Ser
                165                 170                 175

Met Gly Gly Ala Met Ala Ala Phe Cys Ala Leu Asp Leu Ala Ile Lys
            180                 185                 190

Leu Gly Ser Asp Asn Val Gln Leu Met Thr Phe Gly Gln Pro Arg Val
        195                 200                 205

Gly Asn Ala Val Phe Ala Ser Tyr Phe Ala Lys Tyr Val Pro Asn Thr
    210                 215                 220

Ile Arg Leu Val His Gly His Asp Ile Val Pro His Leu Pro Pro Tyr
225                 230                 235                 240

Phe Ser Phe Leu Ser Lys Leu Thr Tyr His His Phe Pro Arg Glu Val
                245                 250                 255

Trp Ile Asp Glu Ser Asp Gly Asn Thr Thr Glu Gln Ile Cys Asp Ala
            260                 265                 270

Ser Gly Glu Asp Pro Asn Cys Cys Arg Cys Leu Ser Ile Leu Ser Leu
        275                 280                 285

Ser Ile Gln Asp His Phe Thr Tyr Leu Gly Val Asp Met Glu Ser Asp
    290                 295                 300

Asp Trp Ser Thr Cys Arg Ile Ile Thr Ala Gln Ser Val Glu Arg Leu
305                 310                 315                 320

Arg Lys His Leu Ser Ser Asn Ile Ile Met Thr Lys His Ala Ile Glu
                325                 330                 335

Val Ser Ile Val Glu Asn Ser Met Gln Thr Asp Trp Ser Ser Arg
            340                 345                 350
```

<210> SEQ ID NO 4
<211> LENGTH: 3263
<212> TYPE: DNA
<213> ORGANISM: Triticum aestivum

<400> SEQUENCE: 4

```
atggagcgac ggaggcgggt cgctgtgctg ccctggtgc tcctgctgct ctcggcttgt      60
catggaagaa gaggtatgac ctcgattatc tttcttttttt ttgttgggta actgttctaa    120
gttttcctca aatgaattcc aagaacgtgt taactaattc agtagcgatc gggctgttta    180
ctgagttcat tctgactgcc atgattgaag caagcataga tgaatatcag tgcatacgca    240
ggcatttcaa aaggtgtaat catgcaggga gagaaagggg gcagctgtgg cactgacgaa    300
attgccctgc tccctgtaaa tttcgccgag ttctgattgc ctgttagcag cacactggcc    360
aacaactgaa ctaattgaat gcacttcttg ttgtggctgg ggccttgggg gttgtatcca    420
aacatctgga aaaagttgta ctatctttgt gtggacagaa aaggaaatta ggtggccgac    480
agttggaact tacctggtgc cttgttaaca aaatggagtt ctggttgcat attggttggt    540
catctctaga aaataaaagg gttgaattaa gaagaacgag ttgatgatga accgtggcag    600
caaacaacca ttgtactgtt gtggagcttg acttgctctg gggactctac tagcatcatc    660
cacgatgccc ccaattgatc tttagctgcc atatctaagc attattttca gtgattcaca    720
gcaaaagacc atcatagatt cttttggagc ttggcttgac agatctagtg cgtttacagc    780
atatggcact taacctagta ctcctatttg ataagccccc cacctgattt ctgtctgtca    840
tgtactcata tcgttgcaat attttcagtt atccacttgc tctaggtgga ttctgtgatt    900
tgtgaatata agtggtttca gagaataggt gaaattgaat catctatgcc cttttaactt    960
ggctgtcacc cgttcatgct taacctctcc tggtaattag aacttacttt tgttctatcc   1020
ctcagatatt atatgcacaa actgaatcaa agcgaacttg tgctagaagc tgccacagat   1080
atgacaggca aaaatcaatt ggggtcattt attctgtttg ctttcatttt gttcaatttg   1140
tctttcttgg cgtaaatgtt tgtccatctg ctttggcatc ttcttatgtc tgaaattgat   1200
cttctgcact tgtgctcaag atggcatcat ttaatatgct agtaaactaa ctgttttcat   1260
tgtcgcagag ttctctgtca atcaggatca gagtcttata tatgatcata ctcttgctaa   1320
gaccatcgtg aatatgcttc ggctgtaag ttaaacttat gctcattatt ccattaaatg    1380
catgtcatgc tttctaaatg gagctttagt tcgtctttat ctagaatctt gttaagtcaa   1440
attaactaaa tactgtctgc aggtgtatat gacagattta acagctttgt atacatggac   1500
atgctcaaga tgcaatgact tgactcaagt aagaaacctt ccaactgttc tcttccattc   1560
atatctatct aggggtgctt atttgttttc ctgaaattac aactgtcaaa cagtaaggga   1620
tctatcaaga tgctcgccaa tggttggttg ggtgtcatat gcagcagccc gtcaactata   1680
cagcttatag aatctgtcct ttcttattta tacattcacc tacttctgaa ataggacttc   1740
gagatgaggt ctctaattgt tgatgtggag aactgcttgc aggttcctat cttaacacac   1800
tccatttaa gttgtcataa atttccggca tatttcttat caagtgtact aaacttttca   1860
tgatatggcc ttccttttac ctgccattct acgggtgaac aatgtgacag gcatttgtcg   1920
gtgtagctca caatctaaat gccataatag ttgcaatcag agggactcaa gagaacaggt   1980
actaataaaa ttgcatgtgc ttctagtatt cccagttaaa ccggtatgct ttatgtgtta   2040
ctattctgat ttcttgagtt acatgtcatt tatgtttag atttgcttgc tcagtgtgca   2100
```

```
gaattggatc aaggacttgg tatggaagca gcttgatcta agctatccag acatgccaaa    2160
tgcaaaggtt attgccaata aactgtttat actttcttaa aagagaaaag gaaaggcaga    2220
tgcacgtttt gctaaaagac tttctactac tctggttaaa ggtgcacagt ggattttct    2280 cctcctataa taatacaatt ttgcgtctag ctatcacaag tgctgtgcac aaggcaagaa    2340
agacatatgg ggatatcggc gtcatagtca cagggcactc aatgggagga gccatggctg    2400
ccttctgtgc actcgatctt gctgtaagta cacaagatcc aatgtttcac aaatacattc    2460
aatgtccaga ctcttaattc cttccaggtt ataaagtgcg gtcttgcatc atattcctaa    2520
caccagcact ctaataattg aggcttgtta ttatgtaagc tgttgatttt tctcttcaaa    2580
ccctatccac agatcaagct cggaagcgac aatgttcaac tcatgacttt cggacagcct    2640
cgtgttggca atgctgtttt cgcctcctac tttgccaaat atgtgccaaa cacaattcga    2700
ctggtacacg gacatgatat cgtgccgcat ttgccacctt atttctcctt tctttccaaa    2760
ctgacgtacc accacttccc aagagaggta taccttgggc acaaacgtat aattacgctt    2820
tcttggatat caactcagtc cctgggcttc atctctgtgc tatgcttatt ccgcccaaat    2880
ttcaggtatg gatcgatgat tctgacgaca acacaaccga acagatttgt gatgccagcg    2940
gcgaagaccc aaaactgctg caggttttaca gctcagacct tccttgcagt tcaattgcct    3000
gtctcttctc ctaattctaa catttcccca ctgatcattt tactaggtgc ctctccatac    3060
tgagtttgag cattcaggac catttcacat acctgggagt cgatatggaa tcagatgact    3120
ggagcacctg cagaatcatc acagcacaaa gtgttgagcg actacggaag gatctcgcca    3180
gcaacatcat catgacaaag cacggcgtcg aggtctccat tgtcgagaat agcgtgcaga    3240
cagactggag cagttccata tag                                            3263

<210> SEQ ID NO 5
<211> LENGTH: 1056
<212> TYPE: DNA
<213> ORGANISM: Triticum aestivum

<400> SEQUENCE: 5
atggagcgac ggaggcgggt cgctgtgctg gccctggtgc tcctgctgct ctcggcttgt     60
catggaagaa gagagttctc tgtcaatcag gatcagagtc ttatatatga tcatactctt    120
gctaagacca tcgtggaata tgcttcggct gtgtatatga cagatttaac agctttgtat    180
acatggacat gctcaagatg caatgacttg actcaagact tcgagatgag gtctctaatt    240
gttgatgtgg agaactgctt gcaggcattt gtcggtgtag ctcacaatct aaatgccata    300
atagttgcaa tcagagggac tcaagagaac agtgtgcaga attggatcaa ggacttggta    360
tggaagcagc ttgatctaag ctatccagac atgccaaatg caaaggtgca cagtggatttt   420 ttctcctcct ataataatac aattttgcgt ctagctatca caagtgctgt gcacaaggca    480
agaaagacat atggggatat cggcgtcata gtcacagggc actcaatggg aggagccatg    540
gctgccttct gtgcactcga tcttgctatc aagctcggaa cgacaatgt tcaactcatg     600 actttcggac agcctcgtgt tggcaatgct gttttcgcct cctactttgc caaatatgtg    660
ccaaacacaa ttcgactggt acacggacat gatatcgtgc cgcatttgcc accttatttc    720
tcctttcttt ccaaactgac gtaccaccac ttcccaagag aggtatggat cgatgattct    780
gacgacaaca caaccgaaca gatttgtgat gccagcggcg aagacccaaa ctgctgcagg    840
tgcctctcca tactgagttt gagcattcag gaccatttca catacctggg agtcgatatg    900
gaatcagatg actggagcac ctgcagaatc atcacagcac aaagtgttga gcgactacgg    960
```

```
aaggatctcg ccagcaacat catcatgaca aagcacggcg tcgaggtctc cattgtcgag    1020
aatagcgtgc agacagactg gagcagttcc atatag                              1056
```

<210> SEQ ID NO 6
<211> LENGTH: 351
<212> TYPE: PRT
<213> ORGANISM: Triticum aestivum

<400> SEQUENCE: 6

| | | | | | | | | | | | | | | |
|---|---|---|---|---|---|---|---|---|---|---|---|---|---|---|
| Met | Glu | Arg | Arg | Arg | Val | Ala | Val | Leu | Ala | Leu | Val | Leu | Leu | Leu |
| 1 | | | | 5 | | | | | 10 | | | | | 15 |
| Leu | Ser | Ala | Cys | His | Gly | Arg | Arg | Glu | Phe | Ser | Val | Asn | Gln | Asp | Gln |
| | | | 20 | | | | | 25 | | | | | 30 | | |
| Ser | Leu | Ile | Tyr | Asp | His | Thr | Leu | Ala | Lys | Thr | Ile | Val | Glu | Tyr | Ala |
| | | 35 | | | | | 40 | | | | | 45 | | | |
| Ser | Ala | Val | Tyr | Met | Thr | Asp | Leu | Thr | Ala | Leu | Tyr | Thr | Trp | Thr | Cys |
| | 50 | | | | | 55 | | | | | 60 | | | | |
| Ser | Arg | Cys | Asn | Asp | Leu | Thr | Gln | Asp | Phe | Glu | Met | Arg | Ser | Leu | Ile |
| 65 | | | | | 70 | | | | | 75 | | | | | 80 |
| Val | Asp | Val | Glu | Asn | Cys | Leu | Gln | Ala | Phe | Val | Gly | Val | Ala | His | Asn |
| | | | | 85 | | | | | 90 | | | | | 95 | |
| Leu | Asn | Ala | Ile | Ile | Val | Ala | Ile | Arg | Gly | Thr | Gln | Glu | Asn | Ser | Val |
| | | | 100 | | | | | 105 | | | | | 110 | | |
| Gln | Asn | Trp | Ile | Lys | Asp | Leu | Val | Trp | Lys | Gln | Leu | Asp | Leu | Ser | Tyr |
| | | 115 | | | | | 120 | | | | | 125 | | | |
| Pro | Asp | Met | Pro | Asn | Ala | Lys | Val | His | Ser | Gly | Phe | Phe | Ser | Ser | Tyr |
| | 130 | | | | | 135 | | | | | 140 | | | | |
| Asn | Asn | Thr | Ile | Leu | Arg | Leu | Ala | Ile | Thr | Ser | Ala | Val | His | Lys | Ala |
| 145 | | | | | 150 | | | | | 155 | | | | | 160 |
| Arg | Lys | Thr | Tyr | Gly | Asp | Ile | Gly | Val | Ile | Val | Thr | Gly | His | Ser | Met |
| | | | | 165 | | | | | 170 | | | | | 175 | |
| Gly | Gly | Ala | Met | Ala | Ala | Phe | Cys | Ala | Leu | Asp | Leu | Ala | Ile | Lys | Leu |
| | | | 180 | | | | | 185 | | | | | 190 | | |
| Gly | Ser | Asp | Asn | Val | Gln | Leu | Met | Thr | Phe | Gly | Gln | Pro | Arg | Val | Gly |
| | | 195 | | | | | 200 | | | | | 205 | | | |
| Asn | Ala | Val | Phe | Ala | Ser | Tyr | Phe | Ala | Lys | Tyr | Val | Pro | Asn | Thr | Ile |
| | 210 | | | | | 215 | | | | | 220 | | | | |
| Arg | Leu | Val | His | Gly | His | Asp | Ile | Val | Pro | His | Leu | Pro | Pro | Tyr | Phe |
| 225 | | | | | 230 | | | | | 235 | | | | | 240 |
| Ser | Phe | Leu | Ser | Lys | Leu | Thr | Tyr | His | His | Phe | Pro | Arg | Glu | Val | Trp |
| | | | | 245 | | | | | 250 | | | | | 255 | |
| Ile | Asp | Asp | Ser | Asp | Asn | Thr | Thr | Glu | Gln | Ile | Cys | Asp | Ala | Ser |
| | | | 260 | | | | | 265 | | | | | 270 | | |
| Gly | Glu | Asp | Pro | Asn | Cys | Cys | Arg | Cys | Leu | Ser | Ile | Leu | Ser | Leu | Ser |
| | | 275 | | | | | 280 | | | | | 285 | | | |
| Ile | Gln | Asp | His | Phe | Thr | Tyr | Leu | Gly | Val | Asp | Met | Glu | Ser | Asp | Asp |
| | 290 | | | | | 295 | | | | | 300 | | | | |
| Trp | Ser | Thr | Cys | Arg | Ile | Ile | Thr | Ala | Gln | Ser | Val | Glu | Arg | Leu | Arg |
| 305 | | | | | 310 | | | | | 315 | | | | | 320 |
| Lys | Asp | Leu | Ala | Ser | Asn | Ile | Ile | Met | Thr | Lys | His | Gly | Val | Glu | Val |
| | | | | 325 | | | | | 330 | | | | | 335 | |
| Ser | Ile | Val | Glu | Asn | Ser | Val | Gln | Thr | Asp | Trp | Ser | Ser | Ile |
| | | | 340 | | | | | 345 | | | | | 350 | |

<210> SEQ ID NO 7
<211> LENGTH: 3460
<212> TYPE: DNA
<213> ORGANISM: Triticum aestivum

<400> SEQUENCE: 7

| | | | | | |
|---|---|---|---|---|---|
| atggggaggt | ggaggcgggc | cggcgtgctg | gctctggtgc | tcctgctgct | ctccgcttgc | 60 |
| catggaagac | gaggtatggt | cttggttacc | ttttctttcc | tttttctttg | cgaaacatag | 120 |
| taagtagaac | atatcacaaa | cgtgcttcgg | ttaccaattt | tgatgcttgc | ttgttgggtg | 180 |
| actgttctaa | gttttcctca | aatgaatttc | caagaacgtg | ttagctaatt | cagtagcgat | 240 |
| cgggctgttt | actgaattca | ttctgactgc | cataattaga | gaaagcataa | gatgaatgtc | 300 |
| agtgcatacg | caggcttttc | aaaaggtgta | atcatgcagg | gagaggaagg | gggcagctgt | 360 |
| ggcagactga | cgaaattgcc | ctgctccctg | taaatttcgc | caagttctga | ttgcctgtta | 420 |
| gccgcgcact | ggccaacaac | tcaactaatt | gaatgcgctt | cttgttgttg | tggctggggc | 480 |
| cttggggtt | gtatccaaac | atctggaaaa | agttgtacta | tctttgtgtg | acagaaaag | 540 |
| gaaattaggt | ggctgacagt | tggaacatac | ctggtgcctt | gttaacataa | cgaagttctg | 600 |
| gttgcatatg | gttggtcacc | tccagaaaat | agaagtgttg | aattaagaag | aacgagtcga | 660 |
| tgaaccgtgg | caggcaaaca | gccattatac | tgttgtggag | cttgacttgc | tctggggatt | 720 |
| ctactagcat | catccatgat | gcccccaatt | gatctttagc | tgccatatct | aagcattatt | 780 |
| ttcagtgatt | cacagcaaaa | gaccatcata | acttcttttg | gagcttggct | tgacagatct | 840 |
| agtgcgttta | caacatatgg | cacttaacct | aatactccta | tttgataagg | ccccaactg | 900 |
| atttctgtct | gtcatatact | catatcattg | caatattttc | agttatccac | ttgctctagg | 960 |
| tggattctgt | gatttgtgaa | ataagtggt | ttcagccttc | aggacatgag | aataggtgaa | 1020 |
| attgaatcat | ctatgcccctt | ttaacttggc | tgtcacccgt | tcatgcttaa | cctctcctgg | 1080 |
| taattagaac | ttacttttgt | tctatacaca | aacttaatca | aagtgaactt | gtgctaaaag | 1140 |
| ctgccacaga | tatgacaggc | aaaaatcaat | tggggtcatt | tattctgttt | gctttcagtt | 1200 |
| tgttcaattt | gttttttcttg | gcataaatgt | ttgtccatct | gctttggcat | cttcttatat | 1260 |
| ctgaaattga | tcttctgcac | ttgtgttatt | gcatcattta | atatgctaat | aaactaactg | 1320 |
| ttttcattat | cgcagagttc | tctgtcaaga | atcacggtca | gagtcttata | tatgatcata | 1380 |
| ctcttgctaa | gaccatcgtg | gagtatgctt | cggctgtaag | tttaacttat | gctcattatt | 1440 |
| gcattaaatg | catgtcatgc | tttctaaata | gagctttagt | ttgtcttttgt | cttgaatctt | 1500 |
| gttaagtcaa | attaactaaa | tactgtctgc | aggtgtatat | gacagattta | acagctttgt | 1560 |
| atacatggac | atgctcaaga | tgcaatgact | tgactcaagt | aagaaaccgt | ccaactgttc | 1620 |
| tcttccattc | atatctactc | cctccgtccc | aaaattattg | tcttaaattt | gtctagatac | 1680 |
| ggatgtacct | aatactaaaa | cgtgacttga | tacatccgta | tttagacaaa | tctaagacaa | 1740 |
| gaattttggg | acggagggag | tatctagggg | tgcttatttg | ttttcctgaa | attataactg | 1800 |
| ttcaaacagt | aagggatcta | tcaagatgct | cgccaatggt | tggttaggtg | tcatatgcag | 1860 |
| cagcccgtca | actatacagc | ttatagaatc | tgtcatttct | tatttataca | ttcacctact | 1920 |
| tctgaaatag | gacttcgaga | tgaggtctct | aattgttgat | gtggagaact | gcttgcaggt | 1980 |
| tcctatctta | acacactcca | tttaagttg | tcataaattt | ccggcatatt | tcttatcaag | 2040 |
| tgtactgaac | atctcatgat | atggccttcc | ttttacctgc | cattctacgg | gtgaacaatg | 2100 |
| tgacaggcat | ttgtcggtgt | agctcacaat | ctaaattcca | taatagttgc | aatcagagga | 2160 |

-continued

```
actcaagaga acaggtacta atcaaattgc atgtgcttct agtattccca gttaaaccgg      2220
tatgctttat gtgttactat tccgatttct tgagtcacat gtcatttatg ttttagattt      2280
gcttgctcag tgtgcagaat tggatcaagg acttggtatg gaagcagctt gatctaagct      2340
atccagacat gccaaatgca aaggttattg ccaataaact gtttatactt tcttaaaaga      2400
gaaaaggaaa ggcagatgca ccttttttgct aaaagacttt ctactactct ggttaaaggt     2460
gcacagtgga ttttctcct cctataataa tacaattttg cgtctagcta tcacaagtga       2520
tgtgcacaac gcaagaaaga catatgggga tattggtgtc atagtcacag ggcactcaat      2580
gggaggagcc atggctgcct tctgtgcact cgatcttgct gtaagtacac aagatccaat      2640
gtttcacaaa tacattcaat gtccagactc ttaattcctc ccaggttata aattgcggtc      2700
ttgtatcaaa ttcctaacac cagcactcta atatttgagg cttgttatta tgtaagctgt      2760
tgatttttct cttcaaaccc tatccacaga tcaagctcgg aagcgacaat gttcaactca      2820
tgactttcgg acagcctcgt gtcggcaatg ctgttttcgc ctcctacttt gccaaatatg      2880
taccaaacac aattcgactg gtacacggac atgatattgt gccgcatttg ccaccttatt      2940
tctccttcct ttccaaactg acgtaccacc acttcccaag agaggtatac cttgggcaca      3000
aacttataaa tatgctttcc aactcctagg aagccttat cgctgtgtta tgcttagtgc       3060
ttgctcatat tttaggtatg gatcaacgaa tctgatggca acacaacgga acagatatgt      3120
gatgccagcg gcgaagaccc aaactgctgc aggtttttac agagcacaga ccttccttgc      3180
ggctcaactg cttgtctctt tagctcctag ttctgacatt atccccatcg atcgttttac      3240
taggtgcctc tccatattga gcctgagcat tcaggaccat ttcacatacc tgggagtaga      3300
catggaatca gatgactgga gcacctgcag aatcatcaca gcacaaagcg ttgagcgatt      3360
acgtaaggat ctcggcagca acatcatcat gacaaagcac ggcgtcgagg tctccattgt      3420
cgagaatagc atgcagacag actggagcag ttccagatag                            3460
```

<210> SEQ ID NO 8
<211> LENGTH: 1059
<212> TYPE: DNA
<213> ORGANISM: Triticum aestivum

<400> SEQUENCE: 8

```
atggggaggt ggaggcgggc cggcgtgctg gctctggtgc tcctgctgct ctccgcttgc        60
catggaagac gagagttctc tgtcaagaat cacggtcaga gtcttatata tgatcatact       120
cttgctaaga ccatcgtgga gtatgcttcg gctgtgtata tgacagattt aacagctttg       180
tatacatgga catgctcaag atgcaatgac ttgactcaag acttcgagat gaggtctcta       240
attgttgatg tggagaactg cttgcaggca tttgtcggtg tagctcacaa tctaaattcc       300
ataatagttg caatcagagg aactcaagag aacagtgtgc agaattggat caaggacttg       360
gtatggaagc agcttgatct aagctatcca gacatgccaa atgcaaaggt gcacagtgga       420 ttttctcct cctataataa tacaattttg cgtctagcta tcacaagtga tgtgcacaac        480
gcaagaaaga catatgggga tattggtgtc atagtcacag ggcactcaat gggaggagcc      540
atggctgcct tctgtgcact cgatcttgct atcaagctcg gaagcgacaa tgttcaactc       600
atgactttcg gacagcctcg tgtcggcaat gctgttttcg cctcctactt tgccaaatat      660
gtaccaaaca caattcgact ggtacacgga catgatattg tgccgcattt gccaccttat      720
ttctcctttc tttccaaact gacgtaccac cacttcccaa gagaggtatg gatcaacgaa      780
```

-continued

```
tctgatggca acacaacgga acagatatgt gatgccagcg gcgaagaccc aaactgctgc    840
aggtgcctct ccatattgag cctgagcatt caggaccatt tcacatacct gggagtagac    900
atggaatcag atgactggag cacctgcaga atcatcacag cacaaagcgt tgagcgatta    960
cgtaaggatc tcggcagcaa catcatcatg acaaagcacg cgtcgaggt ctccattgtc    1020 gagaatagca tgcagacaga ctggagcagt tccagatag                          1059
```

<210> SEQ ID NO 9
<211> LENGTH: 352
<212> TYPE: PRT
<213> ORGANISM: Triticum aestivum

<400> SEQUENCE: 9

| Met | Gly | Arg | Trp | Arg | Ala | Gly | Val | Leu | Ala | Leu | Val | Leu | Leu | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Leu Ser Ala Cys His Gly Arg Arg Glu Phe Ser Val Lys Asn His Gly
            20                  25                  30

Gln Ser Leu Ile Tyr Asp His Thr Leu Ala Lys Thr Ile Val Glu Tyr
        35                  40                  45

Ala Ser Ala Val Tyr Met Thr Asp Leu Thr Ala Leu Tyr Thr Trp Thr
    50                  55                  60

Cys Ser Arg Cys Asn Asp Leu Thr Gln Asp Phe Glu Met Arg Ser Leu
65                  70                  75                  80

Ile Val Asp Val Glu Asn Cys Leu Gln Ala Phe Val Gly Val Ala His
                85                  90                  95

Asn Leu Asn Ser Ile Ile Val Ala Ile Arg Gly Thr Gln Glu Asn Ser
            100                 105                 110

Val Gln Asn Trp Ile Lys Asp Leu Val Trp Lys Gln Leu Asp Leu Ser
        115                 120                 125

Tyr Pro Asp Met Pro Asn Ala Lys Val His Ser Gly Phe Phe Ser Ser
    130                 135                 140

Tyr Asn Asn Thr Ile Leu Arg Leu Ala Ile Thr Ser Asp Val His Asn
145                 150                 155                 160

Ala Arg Lys Thr Tyr Gly Asp Ile Gly Val Ile Val Thr Gly His Ser
                165                 170                 175

Met Gly Gly Ala Met Ala Ala Phe Cys Ala Leu Asp Leu Ala Ile Lys
            180                 185                 190

Leu Gly Ser Asp Asn Val Gln Leu Met Thr Phe Gly Gln Pro Arg Val
        195                 200                 205

Gly Asn Ala Val Phe Ala Ser Tyr Phe Ala Lys Tyr Val Pro Asn Thr
    210                 215                 220

Ile Arg Leu Val His Gly His Asp Ile Val Pro His Leu Pro Pro Tyr
225                 230                 235                 240

Phe Ser Phe Leu Ser Lys Leu Thr Tyr His His Phe Pro Arg Glu Val
                245                 250                 255

Trp Ile Asn Glu Ser Asp Gly Asn Thr Thr Glu Gln Ile Cys Asp Ala
            260                 265                 270

Ser Gly Glu Asp Pro Asn Cys Cys Arg Cys Leu Ser Ile Leu Ser Leu
        275                 280                 285

Ser Ile Gln Asp His Phe Thr Tyr Leu Gly Val Asp Met Glu Ser Asp
    290                 295                 300

Asp Trp Ser Thr Cys Arg Ile Ile Thr Ala Gln Ser Val Glu Arg Leu
305                 310                 315                 320

Arg Lys Asp Leu Gly Ser Asn Ile Ile Met Thr Lys His Gly Val Glu

```
                325                 330                 335
Val Ser Ile Val Glu Asn Ser Met Gln Thr Asp Trp Ser Ser Ser Arg
        340                 345                 350
```

<210> SEQ ID NO 10
<211> LENGTH: 30
<212> TYPE: DNA
<213> ORGANISM: Artificial Sequence
<220> FEATURE:
<223> OTHER INFORMATION: Primer for OsLip1

<400> SEQUENCE: 10
gaaattgatc ttctgcactt gtgttcagga                              30

<210> SEQ ID NO 11
<211> LENGTH: 27
<212> TYPE: DNA
<213> ORGANISM: Artificial Sequence
<220> FEATURE:
<223> OTHER INFORMATION: Primer for OsLip1

<400> SEQUENCE: 11
tggggataat gttagaacta ggagcta                                 27

<210> SEQ ID NO 12
<211> LENGTH: 28
<212> TYPE: DNA
<213> ORGANISM: Artificial Sequence
<220> FEATURE:
<223> OTHER INFORMATION: Primer for OsLip1

<400> SEQUENCE: 12
gacaggcaaa aatcaattgg ggtcattt                                28

<210> SEQ ID NO 13
<211> LENGTH: 31
<212> TYPE: DNA
<213> ORGANISM: Artificial Sequence
<220> FEATURE:
<223> OTHER INFORMATION: Primer for OsLip1

<400> SEQUENCE: 13
tgatcagtgg ggaaatgtta gaattaggag a                            31

<210> SEQ ID NO 14
<211> LENGTH: 33
<212> TYPE: DNA
<213> ORGANISM: Artificial Sequence
<220> FEATURE:
<223> OTHER INFORMATION: Primer for OsLip1

<400> SEQUENCE: 14
ctgaaattga tcttctgcac ttgtgttatt gca                          33

<210> SEQ ID NO 15
<211> LENGTH: 30
<212> TYPE: DNA
<213> ORGANISM: Artificial Sequence
<220> FEATURE:
<223> OTHER INFORMATION: Primer for OsLip1

<400> SEQUENCE: 15
agcataacac agcgataaag gcttcctagg                              30

<210> SEQ ID NO 16

```
<211> LENGTH: 21
<212> TYPE: DNA
<213> ORGANISM: Artificial Sequence
<220> FEATURE:
<223> OTHER INFORMATION: Primer for OsLip1

<400> SEQUENCE: 16
tctctgtcaa gaatcacggt c                                              21

<210> SEQ ID NO 17
<211> LENGTH: 20
<212> TYPE: DNA
<213> ORGANISM: Artificial Sequence
<220> FEATURE:
<223> OTHER INFORMATION: Primer for OsLip1

<400> SEQUENCE: 17
gctgctgcat atgacaccta                                                20

<210> SEQ ID NO 18
<211> LENGTH: 22
<212> TYPE: DNA
<213> ORGANISM: Artificial Sequence
<220> FEATURE:
<223> OTHER INFORMATION: Primer for OsLip1

<400> SEQUENCE: 18
cacagtggat ttttctcctc ct                                             22

<210> SEQ ID NO 19
<211> LENGTH: 22
<212> TYPE: DNA
<213> ORGANISM: Artificial Sequence
<220> FEATURE:
<223> OTHER INFORMATION: Primer for OsLip1

<400> SEQUENCE: 19
ccgatatccc catatgtctt tc                                             22

<210> SEQ ID NO 20
<211> LENGTH: 20
<212> TYPE: DNA
<213> ORGANISM: Artificial Sequence
<220> FEATURE:
<223> OTHER INFORMATION: Primer for OsLip1

<400> SEQUENCE: 20
gacccagttt caacagcaac                                                20

<210> SEQ ID NO 21
<211> LENGTH: 21
<212> TYPE: DNA
<213> ORGANISM: Artificial Sequence
<220> FEATURE:
<223> OTHER INFORMATION: Primer for OsLip1

<400> SEQUENCE: 21
cggacctaac agctctatat a                                              21

<210> SEQ ID NO 22
<211> LENGTH: 23
<212> TYPE: DNA
<213> ORGANISM: Artificial Sequence
<220> FEATURE:
<223> OTHER INFORMATION: Primer for OsLip1

<400> SEQUENCE: 22
```

```
cacttgatct tgttgtgaac tac                                              23

<210> SEQ ID NO 23
<211> LENGTH: 20
<212> TYPE: DNA
<213> ORGANISM: Artificial Sequence
<220> FEATURE:
<223> OTHER INFORMATION: Primer for OsLip1

<400> SEQUENCE: 23
gcgtgaggca agtatctctt                                                  20

<210> SEQ ID NO 24
<211> LENGTH: 20
<212> TYPE: DNA
<213> ORGANISM: Artificial Sequence
<220> FEATURE:
<223> OTHER INFORMATION: Primer for OsLip1

<400> SEQUENCE: 24
tgtccatgcc atgactgcaa                                                  20

<210> SEQ ID NO 25
<211> LENGTH: 21
<212> TYPE: DNA
<213> ORGANISM: Artificial Sequence
<220> FEATURE:
<223> OTHER INFORMATION: Primer for OsLip1

<400> SEQUENCE: 25
ccagtgctgc ttggaatgat g                                                21

<210> SEQ ID NO 26
<211> LENGTH: 3672
<212> TYPE: DNA
<213> ORGANISM: Oryza sativa

<400> SEQUENCE: 26
atgatgggag gttggttggg atgtgtctgt aggttcatgg agaggtggag atgcgtcagt       60
gtgttggctc tggtgctctt gctgtcaaat gcttcccatg ggagaggtag tttcatgtga      120 cccttttgccc taagtttcca attttgatgc ttgttgggta attgttctaa gtttgcctca    180
atgtattcca aaatgggtta acgtttaaca gaacaaatag caaatcaagg tattagtaac     240
tgactgcttt ggtgggagaa agcagaccaa tgcttatgca ggcatctgta ataaggttta     300
attttctaga gaaatgggga gtgctgatga tggatgagat tgtcttgttc ttttgatttt     360
accaagttct gggttttggc tgtcggtttg gtatgaaatg accagtaatt tactggagtt     420
actggactag ttgaccaagt tatagctgtt ctgctgttgt aattggggat gcatgagcaa     480
gagtaggtgg gtgacagttg gaatttcttg ctgccctgtc cttactaata taattgatgc     540
cctaattgct gaaaggaag acaaggttgg tgggtgagta gaaaataaca acattggaaa      600
taaagaagtt gatggcaaga agataatgg atataattgt gctcagagat tcctattatt      660
ccaaacacat atttgaacct taaacctaat atttattgag ttctcaactt ctttcttgct     720
tccttaaact tgaattccac ttcattacag cttgtggatt ctttgcattc ataaaacttt     780
gtctcaggat cctgaaatat gtgaagttca acatttata gagtattctt tagtttggcc      840
ttcaccaatg caagcttgac actctgttgg tgaaagttta tttagtactg ctatatgctg     900
catgccatct gccatatatt atatacacaa cttgatcgag cattttttct gcaccaccta     960
```

```
ctccgattgg gcttaatttc acaagaagat ttagctagca gttagcacaa ttttgggc      1020
attaatagtt actcgtcaca tggaactgct gatttgaggt ttaagattga gcttgaagct    1080
accacaagtt taccaggcca gaacgtgata ctggggccac ttttcctata agtttgatgc    1140
cataaaaatt gagaatatga aatcagcttt cggctttcct tcacttatga gcaaatgggg    1200
cttaatatct taagcatgtc caaacaagtc aaatgtcctt aatcaatttt cttttcattt    1260
gtcaacattt gattttatta ccgaatataa tgtcggttcg tctgctgcat accttcgtat    1320
agtagatgta gttgatcatc aatgtttgta ttcatgctct catcatcaaa actggagtg    1380
aactaacttt tttcattata acagatatct ctgtccagca ctctcagcaa actttgaact    1440
atagccatac tcttgccatg actcttgtgg aatatgcttc tgctgtaaga aacttttcct    1500
tatttttaca taagcagtat gtgttctagg taacatttct gttcatgttt tgcatttcac    1560
aaaggcaact gtctctcttt cttgttttct ccttttgccc caaaataaaa tcagctactt    1620
taaaaatgaa aaagaagaa gaagaactta gctgatggct cttcgttttc tccaggtgta     1680
catgacagat ttaacagctc tttatacatg gacgtgctca aggtgtaatg acttgactca    1740
agtaagaagc cttcaagttt gttctgttca attcatattt agagggatac tcattaactg    1800
cgaagtaaag cttatattgt tactgatggt tgggggcaga atcacctcaa atgtccgctt    1860
gtcaggatct gccattcctc ttaatgaatc ataaaagcat tttccttttc ttcttcttta    1920
ggaaaaatat ttcttttgtc atggacagga taaatttgtt gctagttttg atatgactac    1980
atttgaaata gggctttgag atgaaatctc taatcgtgga tgtggagaac tgcctacagg    2040
ttcttatctt acaaatttca aactaatatc ataaattctc gatgatattt gagtacatta    2100
agcgtttaat gattttattt atattgtgtg acactatgtg ggtgaacaat gtaacaggca    2160
ttcgttggtg tggattataa tttaaattca ataattgttg caataagagg gactcaagaa    2220
aacaggtaca ctgattttgc acagtgtgtt actgttccct gttcccatgt gatttatatc    2280
ttgatttgct tactcagtat gcagaattgg atcaaggact tgatatgaa acaacttgat     2340
ctgagctatc ctaacatgcc taacgcaaag gttattatcg ctagcaaagt gtttctatct    2400
ccttaagtcc ttttattaaa agaagatcag tgccttttt ttcccctaaa atatctccac     2460
ttctctgttt aaaggtgcac agtggatttt tctcctccta taataacacg attttacgtc    2520
tagctatcac aagtgctgtc cacaaggcaa gacagtcata tggagatatc aatgtcatag    2580
ttacagggca ctcaatggga ggagccatgg catccttctg tgcgcttgat ctcgctgtaa    2640
gtaccccga ggctcaaagt tttactaata catccagtgt tcagattaca gactcttcta     2700
agacattata gatgtaatat ctgtatcaca ttctttccat aaaaaaattg aatgccatca    2760
ttggttgtta tgtaaactga tacagtcttg ttcttttact ctgtccacag atcaatcttg    2820
gaagcaatag tgttcaactc atgactttcg gacagcctcg tgttggcaat gctgcttttg    2880
cctcttattt tgccaaatat gtgcccaaca cgattcgagt cacacatgga catgatattg    2940
tgccacattt gccccttat ttctcctttc ttccccatct aacttaccac cacttcccaa     3000
gagaggtatg cctcacaggc ttgcacataa gctaattaag aatgcgctct tgtacactta    3060
acttggccct ggctttatct attttatcac tatagcacac tttatgaatt tttgtattaa    3120
cacccttttt atatttacca ttaataatac aaaatcaatg cctagtgcag caagttgtta    3180
gatgctctgc acaccttcca tgggacaatg atactaatct aaatcaaata tgctaatatt    3240
ctttagagat gtggtgttac atcctgtaca gtgtacacac ataatatgct tgttcgaatt    3300
tcaggtatgg gtcaatgatt ctgagggcga cataaccgaa cagatatgtg atgatagtgg    3360
```

```
tgaagatcca aattgctgca ggtttagagg ctcattttaa caacctaaca actcaaatct   3420 ggtttttta gcttctaatt ataatttctg ttccctcgtt tatttcctag gtgcatctcc   3480
acatggagtt tgagcgttca agaccatttc atacctgg gagttgatat ggaagctgac   3540
gactggagca cttgtagaat catcacagct gaaaatgtta ggcaactcca aaaggatctc   3600
gccagcaaca tcatcgtctc caagcactct gtcgatgtca ctattgtaga acctagttca   3660
caaacatatt ga                                                      3672

<210> SEQ ID NO 27
<211> LENGTH: 1077
<212> TYPE: DNA
<213> ORGANISM: Oryza sativa

<400> SEQUENCE: 27
atgatgggag ttggtttgg atgtgtctgt aggttcatgg agaggtggag atgcgtcagt     60
gtgttggctc tggtgctctt gctgtcaaat gcttcccatg ggagagatat ctctgtccag    120
cactctcagc aaactttgaa ctatagccat actcttgcca tgactcttgt ggaatatgct    180
tctgctgtgt acatgacaga tttaacagct ctttatacat ggacgtgctc aaggtgtaat    240
gacttgactc aaggctttga gatgaaatct ctaatcgtgg atgtggagaa ctgcctacag    300
gcattcgttg gtgtggatta taatttaaat tcaataattg ttgcaataag aggaactcaa    360
gaaaacagta tgcagaattg gatcaaggac ttgatatgga acaacttga tctgagctat    420 cctaacatgc ctaacgcaaa ggtgcacagt ggattttct cctcctataa taacacgatt    480
ttacgtctag ctatcacaag tgctgtccac aaggcaagac agtcatatgg agatatcaat    540
gtcatagtta cagggcactc aatgggagga gccatggcat ccttctgtgc gcttgatctc    600
gctatcaatc ttggaagcaa tagtgttcaa ctcatgactt tcggacagcc tcgtgttggc    660
aatgctgctt tgcctctta ttttgccaaa tatgtgccca acacgattcg agtcacacat    720
ggacatgata ttgtgccaca tttgcccct tatttctcct ttcttcccca tctaacttac    780
caccacttcc aagagaggt atgggtcaat gattctgagg gcgacataac cgaacagata    840
tgtgatgata gtggtgaaga tccaaattgc tgcaggtgca tctccacatg gagtttgagc    900
gttcaagacc atttcacata cctgggagtt gatatggaag ctgacgactg gagcacttgt    960
agaatcatca cagctgaaaa tgttaggcaa ctccaaaagg atctcgccag caacatcatc   1020
gtctccaagc actctgtcga tgtcactatt gtagaaccta gttcacaaac atattga     1077

<210> SEQ ID NO 28
<211> LENGTH: 358
<212> TYPE: PRT
<213> ORGANISM: Oryza sativa

<400> SEQUENCE: 28

Met Met Gly Gly Trp Phe Gly Cys Val Cys Arg Phe Met Glu Arg Trp
1               5                   10                  15

Arg Cys Val Ser Val Leu Ala Leu Val Leu Leu Ser Asn Ala Ser
            20                  25                  30

His Gly Arg Asp Ile Ser Val Gln His Ser Gln Gln Thr Leu Asn Tyr
        35                  40                  45

Ser His Thr Leu Ala Met Thr Leu Val Glu Tyr Ala Ser Ala Val Tyr
    50                  55                  60

Met Thr Asp Leu Thr Ala Leu Tyr Thr Trp Thr Cys Ser Arg Cys Asn
65                  70                  75                  80
```

```
Asp Leu Thr Gln Gly Phe Glu Met Lys Ser Leu Ile Val Asp Val Glu
                85                  90                  95

Asn Cys Leu Gln Ala Phe Val Gly Val Asp Tyr Asn Leu Asn Ser Ile
            100                 105                 110

Ile Val Ala Ile Arg Gly Thr Gln Glu Asn Ser Met Gln Asn Trp Ile
        115                 120                 125

Lys Asp Leu Ile Trp Lys Gln Leu Asp Leu Ser Tyr Pro Asn Met Pro
130                 135                 140

Asn Ala Lys Val His Ser Gly Phe Phe Ser Ser Tyr Asn Asn Thr Ile
145                 150                 155                 160

Leu Arg Leu Ala Ile Thr Ser Ala Val His Lys Ala Arg Gln Ser Tyr
                165                 170                 175

Gly Asp Ile Asn Val Ile Val Thr Gly His Ser Met Gly Gly Ala Met
            180                 185                 190

Ala Ser Phe Cys Ala Leu Asp Leu Ala Ile Asn Leu Gly Ser Asn Ser
        195                 200                 205

Val Gln Leu Met Thr Phe Gly Gln Pro Arg Val Gly Asn Ala Ala Phe
210                 215                 220

Ala Ser Tyr Phe Ala Lys Tyr Val Pro Asn Thr Ile Arg Val Thr His
225                 230                 235                 240

Gly His Asp Ile Val Pro His Leu Pro Pro Tyr Phe Ser Phe Leu Pro
                245                 250                 255

His Leu Thr Tyr His His Phe Pro Arg Glu Val Trp Val Asn Asp Ser
            260                 265                 270

Glu Gly Asp Ile Thr Glu Gln Ile Cys Asp Asp Ser Gly Glu Asp Pro
        275                 280                 285

Asn Cys Cys Arg Cys Ile Ser Thr Trp Ser Leu Ser Val Gln Asp His
290                 295                 300

Phe Thr Tyr Leu Gly Val Asp Met Glu Ala Asp Trp Ser Thr Cys
305                 310                 315                 320

Arg Ile Ile Thr Ala Glu Asn Val Arg Gln Leu Gln Lys Asp Leu Ala
                325                 330                 335

Ser Asn Ile Ile Val Ser Lys His Ser Val Asp Val Thr Ile Val Glu
            340                 345                 350

Pro Ser Ser Gln Thr Tyr
        355
```

<210> SEQ ID NO 29
<211> LENGTH: 29
<212> TYPE: DNA
<213> ORGANISM: Artificial Sequence
<220> FEATURE:
<223> OTHER INFORMATION: Primer for OsLip1

<400> SEQUENCE: 29
cacctactcc gattgggctt aatttcaca                                29

<210> SEQ ID NO 30
<211> LENGTH: 35
<212> TYPE: DNA
<213> ORGANISM: Artificial Sequence
<220> FEATURE:
<223> OTHER INFORMATION: Primer for OsLip1

<400> SEQUENCE: 30
gaacaagact gtatcagttt acataacaac caatg                         35

```
<210> SEQ ID NO 31
<211> LENGTH: 20
<212> TYPE: DNA
<213> ORGANISM: Artificial Sequence
<220> FEATURE:
<223> OTHER INFORMATION: Guide sequence for genome editing of OsLip1

<400> SEQUENCE: 31
atttaacagc tctttataca                                                   20

<210> SEQ ID NO 32
<211> LENGTH: 20
<212> TYPE: DNA
<213> ORGANISM: Artificial Sequence
<220> FEATURE:
<223> OTHER INFORMATION: Guide sequence for genome editing of OsLip1

<400> SEQUENCE: 32
attggatcaa ggacttgata                                                   20

<210> SEQ ID NO 33
<211> LENGTH: 20
<212> TYPE: DNA
<213> ORGANISM: Artificial Sequence
<220> FEATURE:
<223> OTHER INFORMATION: Guide sequence for genome editing of OsLip1

<400> SEQUENCE: 33
acctttgcgt taggcatgtt                                                   20

<210> SEQ ID NO 34
<211> LENGTH: 20
<212> TYPE: DNA
<213> ORGANISM: Artificial Sequence
<220> FEATURE:
<223> OTHER INFORMATION: Guide sequence for genome editing of OsLip1

<400> SEQUENCE: 34
agcgagatca agcgcacaga                                                   20

<210> SEQ ID NO 35
<211> LENGTH: 20
<212> TYPE: DNA
<213> ORGANISM: Artificial Sequence
<220> FEATURE:
<223> OTHER INFORMATION: Guide sequence for genome editing of OsLip1

<400> SEQUENCE: 35
aagtggtggt aagttagatg                                                   20

<210> SEQ ID NO 36
<211> LENGTH: 364
<212> TYPE: PRT
<213> ORGANISM: Oryza sativa
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (278)..(281)
<223> OTHER INFORMATION: Xaa can be any naturally occurring amino acid

<400> SEQUENCE: 36
```

```
Met Met Gly Gly Trp Phe Gly Cys Val Cys Arg Phe Met Glu Arg Trp
1               5                   10                  15

Arg Cys Val Ser Val Leu Ala Leu Val Leu Leu Ser Asn Ala Ser
            20                  25                  30

His Gly Arg Xaa Asp Ile Ser Val Gln His Ser Xaa Gln Gln Thr Leu
            35                  40                  45

Asn Tyr Ser His Thr Leu Ala Met Thr Leu Val Glu Tyr Ala Ser Ala
        50                  55                  60

Val Tyr Met Thr Asp Leu Thr Ala Leu Tyr Thr Trp Thr Cys Ser Arg
65                  70                  75                  80

Cys Asn Asp Leu Thr Gln Gly Phe Glu Met Lys Ser Leu Ile Val Asp
                85                  90                  95

Val Glu Asn Cys Leu Gln Ala Phe Val Gly Val Asp Tyr Asn Leu Asn
            100                 105                 110

Ser Ile Ile Val

```
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (266)..(269)
<223> OTHER INFORMATION: Xaa can be any naturally occurring amino acid

<400> SEQUENCE: 37
```

Met Glu Arg Arg Arg Arg Val Ala Val Leu Ala Leu Val Leu Leu Leu
1               5                   10                  15

Leu Ser Ala Cys His Gly Arg Arg Glu Phe Ser Val Lys Asn His Xaa
            20                  25                  30

Asp Gln Ser Leu Ile Tyr Asp His Thr Leu Ala Lys Thr Ile Val Glu
        35                  40                  45

Tyr Ala Ser Ala Val Tyr Met Thr Asp Leu Thr Ala Leu Tyr Thr Trp
50                  55                  60

Thr Cys Ser Arg Cys Asn Asp Leu Thr Gln Asp Phe Glu Met Arg Ser
65                  70                  75                  80

Leu Ile Val Asp Val Glu Asn Cys Leu Gln Ala Phe Val Gly Val Asp
                85                  90                  95

His Asn Leu Asn Ala Ile Ile Val Ala Ile Arg Gly Thr Gln Glu Asn
            100                 105                 110

Ser Val Gln Asn Trp Ile Lys Asp Leu Val Trp Lys Gln Leu Asp Leu
        115                 120                 125

Ser Tyr Pro Asp Met Pro Asn Ala Lys Val His Ser Gly Phe Phe Ser
    130                 135                 140

Ser Tyr Asn Asn Thr Ile Leu Arg Leu Ala Ile Thr Ser Ala Val His
145                 150                 155                 160

Lys Ala Arg Lys Thr Tyr Gly Asp Ile Gly Val Ile Val Thr Gly His
                165                 170                 175

Ser Met Gly Gly Ala Met Ala Ala Phe Cys Ala Leu Asp Leu Ala Ile
            180                 185                 190

Lys Leu Gly Ser Asp Asn Val Gln Leu Met Thr Phe Gly Gln Pro Arg
        195                 200                 205

Val Gly Asn Ala Val Phe Ala Ser Tyr Phe Ala Lys Tyr Val Pro Asn
    210                 215                 220

Thr Ile Arg Leu Val His Gly His Asp Ile Val Pro His Leu Pro Pro
225                 230                 235                 240

Tyr Phe Ser Phe Leu Ser Lys Leu Thr Tyr His His Phe Pro Arg Glu
                245                 250                 255

Val Trp Ile Asp Glu Xaa Asp Gly Asn Xaa Xaa Xaa Xaa Thr Thr Glu
            260                 265                 270

Gln Ile Cys Asp Ala Ser Gly Glu Asp Pro Asn Cys Cys Arg Cys Leu
        275                 280                 285

Ser Ile Leu Ser Leu Ser Ile Gln Asp His Phe Thr Tyr Leu Gly Val
    290                 295                 300

Asp Met Glu Ser Asp Asp Trp Ser Thr Cys Arg Ile Ile Thr Ala Gln
305                 310                 315                 320

Ser Val Glu Arg Leu Arg Lys His Leu Ser Ser Asn Ile Ile Met Thr
                325                 330                 335

Lys His Ala Ile Glu Val Ser Ile Val Glu Asn Ser Met Gln Thr Asp
            340                 345                 350

Trp Ser Ser Ser Arg
        355

```
<210> SEQ ID NO 38
<211> LENGTH: 357
<212> TYPE: PRT
<213> ORGANISM: Triticum aestivum
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (266)..(269)
<223> OTHER INFORMATION: Xaa can be any naturally occurring amino acid

<400> SEQUENCE: 38
```

Met Gly Arg Trp Arg Arg Ala Gly Val Leu Ala Leu Val Leu Leu Leu
1               5                   10                  15

Leu Ser Ala Cys His Gly Arg Arg Glu Phe Ser Val Lys Asn His Xaa
            20                  25                  30

Gly Gln Ser Leu Ile Tyr Asp His Thr Leu Ala Lys Thr Ile Val Glu
        35                  40                  45

Tyr Ala Ser Ala Val Tyr Met Thr Asp Leu Thr Ala Leu Tyr Thr Trp
50                  55                  60

Thr Cys Ser Arg Cys Asn Asp Leu Thr Gln Asp Phe Glu Met Arg Ser
65                  70                  75                  80

Leu Ile Val Asp Val Glu Asn Cys Leu Gln Ala Phe Val Gly Val Ala
                85                  90                  95

His Asn Leu Asn Ser Ile Ile Val Ala Ile Arg Gly Thr Gln Glu Asn
            100                 105                 110

Ser Val Gln Asn Trp Ile Lys Asp Leu Val Trp Lys Gln Leu Asp Leu
        115                 120                 125

Ser Tyr Pro Asp Met Pro Asn Ala Lys Val His Ser Gly Phe Phe Ser
130                 135                 140

Ser Tyr Asn Asn Thr Ile Leu Arg Leu Ala Ile Thr Ser Asp Val His
145                 150                 155                 160

Asn Ala Arg Lys Thr Tyr Gly Asp Ile Gly Val Ile Val Thr Gly His
                165                 170                 175

Ser Met Gly Gly Ala Met Ala Ala Phe Cys Ala Leu Asp Leu Ala Ile
            180                 185                 190

Lys Leu Gly Ser Asp Asn Val Gln Leu Met Thr Phe Gly Gln Pro Arg
        195                 200                 205

Val Gly Asn Ala Val Phe Ala Ser Tyr Phe Ala Lys Tyr Val Pro Asn
210                 215                 220

Thr Ile Arg Leu Val His Gly His Asp Ile Val Pro His Leu Pro Pro
225                 230                 235                 240

Tyr Phe Ser Phe Leu Ser Lys Leu Thr Tyr His His Phe Pro Arg Glu
                245                 250                 255

Val Trp Ile Asn Glu Ser Asp Gly Asn Xaa Xaa Xaa Xaa Thr Thr Glu
            260                 265                 270

Gln Ile Cys Asp Ala Ser Gly Glu Asp Pro Asn Cys Cys Arg Cys Leu
        275                 280                 285

Ser Ile Leu Ser Leu Ser Ile Gln Asp His Phe Thr Tyr Leu Gly Val
290                 295                 300

Asp Met Glu Ser Asp Asp Trp Ser Thr Cys Arg Ile Ile Thr Ala Gln
305                 310                 315                 320

Ser Val Glu Arg Leu Arg Lys Asp Leu Gly Ser Asn Ile Ile Met Thr
                325                 330                 335

```
Lys His Gly Val Glu Val Ser Ile Val Glu Asn Ser Met Gln Thr Asp
            340                 345                 350

Trp Ser Ser Ser Arg
        355

<210> SEQ ID NO 39
<211> LENGTH: 357
<212> TYPE: PRT
<213> ORGANISM: Triticum aestivum
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (266)..(269)
<223> OTHER INFORMATION: Xaa can be any naturally occurring amino acid

<400> SEQUENCE: 39

Met Glu Arg Arg Arg Val Ala Val Leu Ala Leu Val Leu Leu Leu
1               5                   10                  15

Leu Ser Ala Cys His Gly Arg Arg Glu Phe Ser Val Xaa Asn Gln Xaa
            20                  25                  30

Asp Gln Ser Leu Ile Tyr Asp His Thr Leu Ala Lys Thr Ile Val Glu
            35                  40                  45

Tyr Ala Ser Ala Val Tyr Met Thr Asp Leu Thr Ala Leu Tyr Thr Trp
50                  55                  60

Thr Cys Ser Arg Cys Asn Asp Leu Thr Gln Asp Phe Glu Met Arg Ser
65                  70                  75                  80

Leu Ile Val Asp Val Glu Asn Cys Leu Gln Ala Phe Val Gly Val Ala
                85                  90                  95

His Asn Leu Asn Ala Ile Ile Val Ala Ile Arg Gly Thr Gln Glu Asn
            100                 105                 110

Ser Val Gln Asn Trp Ile Lys Asp Leu Val Trp Lys Gln Leu Asp Leu
            115                 120                 125

Ser Tyr Pro Asp Met Pro Asn Ala Lys Val His Ser Gly Phe Phe Ser
130                 135                 140

Ser Tyr Asn Asn Thr Ile Leu Arg Leu Ala Ile Thr Ser Ala Val His
145                 150                 155                 160

Lys Ala Arg Lys Thr Tyr Gly Asp Ile Gly Val Ile Thr Gly His
                165                 170                 175

Ser Met Gly Gly Ala Met Ala Ala Phe Cys Ala Leu Asp Leu Ala Ile
            180                 185                 190

Lys Leu Gly Ser Asp Asn Val Gln Leu Met Thr Phe Gly Gln Pro Arg
            195                 200                 205

Val Gly Asn Ala Val Phe Ala Ser Tyr Phe Ala Lys Tyr Val Pro Asn
            210                 215                 220

Thr Ile Arg Leu Val His Gly His Asp Ile Val Pro His Leu Pro Pro
225                 230                 235                 240

Tyr Phe Ser Phe Leu Ser Lys Leu Thr Tyr His His Phe Pro Arg Glu
                245                 250                 255

Val Trp Ile Asp Asp Ser Asp Asp Asn Xaa Xaa Xaa Xaa Thr Thr Glu
            260                 265                 270

Gln Ile Cys Asp Ala Ser Gly Glu Asp Pro Asn Cys Cys Arg Cys Leu
```

```
              275                 280                 285
Ser Ile Leu Ser Leu Ser Ile Gln Asp His Phe Thr Tyr Leu Gly Val
            290                 295                 300

Asp Met Glu Ser Asp Asp Trp Ser Thr Cys Arg Ile Ile Thr Ala Gln
305                 310                 315                 320

Ser Val Glu Arg Leu Arg Lys Asp Leu Ala Ser Asn Ile Ile Met Thr
                325                 330                 335

Lys His Gly Val Glu Val Ser Ile Val Glu Asn Ser Val Gln Thr Asp
            340                 345                 350

Trp Ser Ser Ser Ile
            355

<210> SEQ ID NO 40
<211> LENGTH: 363
<212> TYPE: PRT
<213> ORGANISM: Triticum aestivum
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (272)..(275)
<223> OTHER INFORMATION: Xaa can be any naturally occurring amino acid

<400> SEQUENCE: 40

Met Gly Ser Arg Arg Trp Val Ala Ala Ala Ala Ala Ala Ala Met Val
1               5                   10                  15

Ala Phe Leu Leu Leu Ser Ala Ala Ser His Gly Gly Arg Arg Gly Pro
            20                  25                  30

Ser Phe Asn Ser Asn Xaa Asn Arg Thr Phe Val Phe Asn Tyr Thr Leu
        35                  40                  45

Ala Lys Thr Ile Val Glu Tyr Ala Ser Ala Val Tyr Met Thr Asp Leu
    50                  55                  60

Thr Ala Leu Tyr Thr Trp Thr Cys Ser Arg Cys Asn Asp Leu Thr Lys
65                  70                  75                  80

Gly Phe Glu Ile Arg Cys Ile Ile Val Asp Ile Gln Asn Cys Leu Gln
                85                  90                  95

Ala Phe Ile Gly Val Asp His Asn Leu Asn Ala Val Ile Val Ala Ile
            100                 105                 110

Arg Gly Thr Gln Glu Asn Ser Val Gln Asn Trp Ile Lys Asp Leu Val
        115                 120                 125

Trp Lys Gln Val Asp Leu Asn Tyr Pro Asn Met Pro Asp Ala Lys Val
    130                 135                 140

His Thr Gly Phe Tyr Ser Ala Tyr Asn Asn Thr Leu Leu Arg Pro Ala
145                 150                 155                 160

Ile Thr Asn Ala Val Arg Lys Ala Arg Arg Leu Tyr Gly Asp Ile Ser
                165                 170                 175

Ile Ile Val Thr Gly His Ser Met Gly Gly Ala Met Ala Ser Phe Cys
            180                 185                 190

Ala Leu Asp Leu Ala Ile Ser Leu Gly Ser Asp Thr Val His Leu Met
        195                 200                 205

Thr Phe Gly Gln Pro Arg Ile Gly Asn Ala Ala Phe Ala Ser Tyr Phe
    210                 215                 220

Glu Gln Tyr Val Pro Ser Ala Ile Arg Val Thr His Glu His Asp Ile
225                 230                 235                 240

Val Pro His Leu Pro Pro Tyr Phe Phe Phe Leu Pro Arg Leu Thr Tyr
```

```
                   245                 250                 255
His His Phe Pro Arg Glu Val Trp Glu His Asp Val Asp Gly Asn Xaa
                260                 265                 270

Xaa Xaa Xaa Thr Thr Phe Arg Val Cys Asp Gly Ser Gly Glu Asp Pro
            275                 280                 285

Asp Cys Cys Arg Ser Val Phe Ala Leu Phe Leu Ser Ala Ser Asp His
    290                 295                 300

Leu Thr Tyr Met Gly Val Glu Ile Ala Ala Asp Asp Trp Ser Thr Cys
305                 310                 315                 320

Arg Ile Val Met Ala Gln Ser Val Glu Arg Leu Gln Leu Tyr Leu Lys
                325                 330                 335

Ser Asn Val Ile Thr Trp Lys Asn Pro Val Asp Ile Ile Ala Asp
                340                 345                 350

His Ser Val Gln Thr Asp Pro Ser Ser Ser
                355                 360

<210> SEQ ID NO 41
<211> LENGTH: 363
<212> TYPE: PRT
<213> ORGANISM: Triticum aestivum
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (272)..(275)
<223> OTHER INFORMATION: Xaa can be any naturally occurring amino acid

<400> SEQUENCE: 41

Met Gly Thr Arg Arg Trp Val Ala Ala Ala Ala Val Xaa Met Val
1               5                   10                  15

Ala Leu Leu Leu Leu Ser Ala Ala Ser His Gly Gly Arg Arg Gly Pro
                20                  25                  30

Ser Phe Asn Ser Asn Xaa Asn Arg Thr Phe Val Phe Asn Tyr Thr Leu
            35                  40                  45

Ala Lys Thr Ile Val Glu Tyr Ala Ser Ala Val Asn Met Thr Asp Leu
    50                  55                  60

Thr Ala Leu Tyr Thr Trp Thr Cys Ser Arg Cys Asn Asp Leu Thr Lys
65                  70                  75                  80

Gly Phe Glu Ile Arg Cys Ile Ile Val Asp Ile Gln Asn Cys Leu Gln
                85                  90                  95

Ala Phe Ile Gly Val Asp His Asn Leu Asn Ala Val Ile Val Ala Ile
            100                 105                 110

Arg Gly Thr Gln Glu Asn Ser Val Gln Asn Trp Ile Lys Asp Leu Val
    115                 120                 125

Trp Lys Gln Val Asp Leu Asn Tyr Pro Asn Met Pro Asp Val Lys Val
130                 135                 140

His Thr Gly Phe Tyr Ser Ala Tyr Asn Asn Thr Leu Leu Arg Pro Ala
145                 150                 155                 160

Ile Thr Asn Ala Val Arg Lys Ala Arg Arg Leu Tyr Gly Asp Ile Ser
                165                 170                 175

Val Ile Val Thr Gly His Ser Met Gly Gly Ala Met Ala Ser Phe Cys
            180                 185                 190
```

```
Ala Leu Asp Leu Ala Ile Ser Leu Gly Ser Asp Ser Val His Leu Met
            195                 200                 205

Thr Phe Gly Gln Pro Arg Ile Gly Asn Ala Ala Phe Ala Ser Tyr Phe
        210                 215                 220

Glu Gln Tyr Val Pro Ser Ala Ile Arg Val Thr His Glu His Asp Ile
225                 230                 235                 240

Val Pro His Leu Pro Pro Tyr Phe Phe Phe Leu Pro His Leu Thr Tyr
                245                 250                 255

His His Phe Pro Arg Glu Val Trp Glu His Asp Val Asp Gly Asn Xaa
                260                 265                 270

Xaa Xaa Xaa Thr Thr Phe Arg Val Cys Asp Gly Ser Gly Glu Asp Pro
            275                 280                 285

Asp Cys Cys Arg Ser Val Phe Ala Leu Phe Leu Ser Ala Ser Asp His
        290                 295                 300

Leu Thr Tyr Met Gly Val Glu Ile Ala Ala Asp Asp Trp Ser Thr Cys
305                 310                 315                 320

Arg Ile Val Met Ala Gln Ser Val Glu Arg Leu Gln Leu Tyr Leu Ala
                325                 330                 335

Ser Asn Val Ile Thr Ser Lys Ile Pro Val Asp Ile Ile Ala Asp
            340                 345                 350

His Ser Val Gln Thr Asp Pro Ser Ser Ser
        355                 360

<210> SEQ ID NO 42
<211> LENGTH: 363
<212> TYPE: PRT
<213> ORGANISM: Triticum aestivum
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (272)..(275)
<223> OTHER INFORMATION: Xaa can be any naturally occurring amino acid

<400> SEQUENCE: 42

Met Gly Thr Arg Arg Trp Val Ala Ala Ala Ala Val Xaa Met Val
1               5                   10                  15

Ala Leu Leu Leu Leu Ser Ala Ala Ser His Gly Gly Arg Arg Gly Pro
            20                  25                  30

Ser Phe Asn Ser Asn Xaa Asn Arg Thr Phe Val Phe Asn Tyr Thr Leu
        35                  40                  45

Ala Lys Thr Ile Val Glu Tyr Ala Ser Ala Val Asn Met Thr Asp Leu
    50                  55                  60

Thr Ala Leu Tyr Thr Trp Thr Cys Ser Arg Cys Asn Asp Leu Thr Lys
65                  70                  75                  80

Gly Phe Glu Ile Arg Cys Ile Ile Val Asp Ile Gln Asn Cys Leu Gln
                85                  90                  95

Ala Phe Ile Gly Val Asp His Asn Leu Asn Ala Val Ile Val Ala Ile
            100                 105                 110

Arg Gly Thr Gln Glu Asn Ser Val Gln Asn Trp Ile Lys Asp Leu Val
        115                 120                 125

Trp Lys Gln Val Asp Leu Asn Tyr Pro Asn Met Pro Asp Val Lys Val
    130                 135                 140
```

-continued

```
His Thr Gly Phe Tyr Ser Ala Tyr Asn Asn Thr Leu Leu Arg Pro Ala
145                 150                 155                 160

Ile Thr Asn Ala Val Arg Lys Ala Arg Arg Leu Tyr Gly Asp Ile Ser
                165                 170                 175

Val Ile Val Thr Gly His Ser Met Gly Gly Ala Met Ala Ser Phe Cys
            180                 185                 190

Ala Leu Asp Leu Ala Ile Ser Leu Gly Ser Asp Ser Val His Leu Met
        195                 200                 205

Thr Phe Gly Gln Pro Arg Ile Gly Asn Ala Ala Phe Ala Ser Tyr Phe
    210                 215                 220

Glu Gln Tyr Val Pro Ser Ala Ile Arg Val Thr His Glu His Asp Ile
225                 230                 235                 240

Val Pro His Leu Pro Pro Tyr Phe Phe Phe Leu Pro His Leu Thr Tyr
                245                 250                 255

His His Phe Pro Arg Glu Val Trp Glu His Asp Val Asp Gly Asn Xaa
            260                 265                 270

Xaa Xaa Xaa Thr Thr Phe Arg Val Cys Asp Gly Ser Gly Glu Asp Pro
        275                 280                 285

Asp Cys Cys Arg Ser Val Phe Ala Leu Phe Leu Ser Ala Ser Asp His
    290                 295                 300

Leu Thr Tyr Met Gly Val Glu Ile Ala Ala Asp Asp Trp Ser Thr Cys
305                 310                 315                 320

Arg Ile Val Met Ala Gln Ser Val Glu Arg Leu Gln Leu Tyr Leu Ala
                325                 330                 335

Ser Asn Val Ile Thr Ser Lys Ile Pro Val Asp Ile Ile Ala Asp
            340                 345                 350

His Ser Val Gln Thr Asp Pro Ser Ser Ser Ser
        355                 360
```

<210> SEQ ID NO 43
<211> LENGTH: 363
<212> TYPE: PRT
<213> ORGANISM: Triticum aestivum
<220> FEATURE:
<221> NAME/KEY: misc_feature
<222> LOCATION: (272)..(275)
<223> OTHER INFORMATION: Xaa can be any naturally occurring amino acid

<400> SEQUENCE: 43

```
Met Gly Ser Arg Arg Trp Val Ala Ala Ala Ala Val Leu
1               5                   10                  15

Ala Leu Leu Leu Leu Ser Ala Ala Ser His Gly Gly Arg Arg Gly Pro
                20                  25                  30

Ser Val Asn Asn Ser Ile Asn Arg Thr Val Val Phe Asn Tyr Thr Leu
            35                  40                  45

Ala Lys Thr Ile Val Tyr Ala Ser Ala Val Tyr Met Thr Asp Leu Thr
        50                  55                  60

Ala Leu Tyr Thr Trp Thr Cys Ser Arg Cys Asn Asp Leu Thr Lys Gly
65                  70                  75                  80

Phe Glu Ile Arg Cys Ile Ile Val Asp Ile Gln Asn Cys Leu Gln Ala
                85                  90                  95

Phe Ile Gly Val Asp His Asn Leu Asn Ala Ile Ile Val Ala Ile Arg
            100                 105                 110

Gly Thr Gln Gln Glu Asn Ser Val Gln Asn Trp Ile Lys Asp Leu Val
        115                 120                 125
```

-continued

```
Trp Lys Gln Val Asp Leu Asn Tyr Pro Asn Met Pro Asn Ala Lys Val
            130                 135                 140
His Thr Gly Phe Tyr Ser Ala Tyr Asn Asn Thr Leu Leu Arg Pro Ala
145                 150                 155                 160
Ile Thr Asn Ala Val Arg Lys Ala Arg Arg Leu Tyr Gly Asp Ile Ser
                165                 170                 175
Val Ile Val Thr Gly His Ser Met Gly Gly Ala Met Ala Ser Phe Cys
            180                 185                 190
Ala Leu Asp Leu Ala Ile Ser Leu Gly Ser Asp Ser Val His Leu Met
        195                 200                 205
Thr Phe Gly Gln Pro Arg Ile Gly Asn Ala Ala Phe Ala Ser Tyr Phe
210                 215                 220
Glu Gln Tyr Val Pro Ser Ala Ile Arg Val Thr His Glu His Asp Ile
225                 230                 235                 240
Val Pro His Leu Pro Pro Tyr Phe Phe Phe Leu Pro His Leu Thr Tyr
                245                 250                 255
His His Phe Pro Arg Glu Val Trp Glu His Asp Val Asp Gly Ser Xaa
            260                 265                 270
Xaa Xaa Xaa Thr Thr Phe Arg Val Cys Asp Asp Ser Gly Glu Asp Pro
        275                 280                 285
Asp Cys Cys Arg Ser Val Phe Ala Leu Phe Leu Ser Ala Ser Asp His
290                 295                 300
Leu Thr Tyr Met Gly Val Glu Ile Ala Ala Asp Asp Trp Ser Thr Cys
305                 310                 315                 320
Arg Ile Val Met Ala Gln Ser Val Glu Arg Leu Gln Leu Tyr Leu Pro
                325                 330                 335
Ser Asn Val Ile Thr Ser Lys Asn Pro Val Asp Ile Ile Ala Asp
            340                 345                 350
His Ser Val Gln Thr Tyr Pro Ser Ser Ser Ser
        355                 360

<210> SEQ ID NO 44
<211> LENGTH: 363
<212> TYPE: PRT
<213> ORGANISM: Triticum aestivum
<220> FEATURE:
<221> NAME/KEY: misc_feature
<222> LOCATION: (272)..(275)
<223> OTHER INFORMATION: Xaa can be any naturally occurring amino acid

<400> SEQUENCE: 44

Met Gly Ser Arg Arg Trp Val Ala Ala Ala Ala Val Leu
1               5                   10                  15
Ala Leu Leu Leu Leu Ser Ala Ala Ser His Gly Gly Arg Arg Gly Pro
            20                  25                  30
Ser Val Asn Asn Ser Ile Asn Arg Thr Val Val Phe Asn Tyr Thr Leu
        35                  40                  45
Ala Lys Thr Ile Val Glu Tyr Ala Ser Ala Val Tyr Met Thr Asp Leu
    50                  55                  60
Thr Ala Leu Tyr Thr Trp Thr Cys Ser Arg Cys Asn Asp Leu Thr Lys
65                  70                  75                  80
Gly Phe Glu Ile Arg Cys Ile Ile Val Asp Ile Gln Asn Cys Leu Gln
                85                  90                  95
Ala Phe Ile Gly Val Asp His Asn Leu Asn Ala Ile Ile Val Ala Ile
            100                 105                 110
Arg Gly Thr Gln Glu Asn Ser Val Gln Asn Trp Ile Lys Asp Leu Val
```

```
            115                 120                 125
Trp Lys Gln Val Asp Leu Asn Tyr Pro Asn Met Pro Asn Ala Lys Val
    130                 135                 140

His Thr Gly Phe Tyr Ser Ala Tyr Asn Asn Thr Leu Leu Arg Pro Ala
145                 150                 155                 160

Ile Thr Asn Ala Val Arg Lys Ala Arg Arg Leu Tyr Gly Asp Ile Ser
                165                 170                 175

Val Ile Val Thr Gly His Ser Met Gly Gly Ala Met Ala Ser Phe Cys
            180                 185                 190

Ala Leu Asp Leu Ala Ile Ser Leu Gly Ser Asp Ser Val His Leu Met
            195                 200                 205

Thr Phe Gly Gln Pro Arg Ile Gly Asn Ala Ala Phe Ala Ser Tyr Phe
    210                 215                 220

Glu Gln Tyr Val Pro Ser Ala Ile Arg Val Thr His Glu His Asp Ile
225                 230                 235                 240

Val Pro His Leu Pro Pro Tyr Phe Phe Phe Leu Pro His Leu Thr Tyr
                245                 250                 255

His His Phe Pro Arg Glu Val Trp Glu His Asp Val Asp Gly Ser Xaa
            260                 265                 270

Xaa Xaa Xaa Thr Thr Phe Arg Val Cys Asp Asp Ser Gly Glu Asp Pro
            275                 280                 285

Asp Cys Cys Arg Ser Val Phe Ala Leu Phe Leu Ser Ala Ser Asp His
    290                 295                 300

Leu Thr Tyr Met Gly Val Glu Ile Ala Ala Asp Asp Trp Ser Thr Cys
305                 310                 315                 320

Arg Ile Val Met Ala Gln Ser Val Glu Arg Leu Gln Leu Tyr Leu Pro
                325                 330                 335

Ser Asn Val Ile Thr Ser Lys Asn Pro Val Asp Ile Ile Ile Ala Asp
            340                 345                 350

His Ser Val Gln Thr Tyr Pro Ser Ser Ser Ser
            355                 360

<210> SEQ ID NO 45
<211> LENGTH: 363
<212> TYPE: PRT
<213> ORGANISM: Triticum aestivum
<220> FEATURE:
<221> NAME/KEY: misc_feature
<222> LOCATION: (272)..(275)
<223> OTHER INFORMATION: Xaa can be any naturally occurring amino acid

<400> SEQUENCE: 45

Met Gly Ser Arg Arg Trp Val Val Ala Ala Ala Ala Ala Ala Val Leu
1               5                   10                  15

Ala Leu Leu Leu Leu Ser Ala Ala Ser His Gly Gly Arg Arg Gly Pro
            20                  25                  30

Ser Val Asn Asn Ser Ile Asn Arg Thr Val Val Phe Asn Tyr Thr Leu
        35                  40                  45

Ala Lys Thr Ile Val Glu Tyr Ala Ser Ala Val Tyr Met Thr Asp Leu
    50                  55                  60

Thr Ala Leu Tyr Thr Trp Thr Cys Ser Arg Cys Asn Asp Leu Thr Lys
65                  70                  75                  80

Gly Phe Glu Ile Arg Cys Ile Ile Val Asp Ile Gln Asn Cys Leu Gln
                85                  90                  95

Ala Phe Ile Gly Val Asp His Asn Leu Asn Ala Ile Ile Val Ala Ile
            100                 105                 110
```

```
Arg Gly Thr Gln Glu Asn Ser Val Gln Asn Trp Ile Lys Asp Leu Val
        115                 120                 125

Trp Lys Gln Val Asp Leu Asn Tyr Pro Asn Met Pro Asn Ala Lys Val
130                 135                 140

His Thr Gly Phe Tyr Ser Ala Tyr Asn Thr Leu Leu Arg Pro Ala
145                 150                 155                 160

Ile Thr Asn Ala Val Arg Lys Ala Arg Arg Leu Tyr Gly Asp Ile Ser
                165                 170                 175

Val Ile Val Thr Gly His Ser Met Gly Gly Ala Met Ala Ser Phe Cys
                180                 185                 190

Ala Leu Asp Leu Ala Ile Ser Leu Gly Ser Asp Ser Val His Leu Met
                195                 200                 205

Thr Phe Gly Gln Pro Arg Ile Gly Asn Ala Ala Phe Ala Ser Tyr Phe
                210                 215                 220

Glu Gln Tyr Val Pro Ser Ala Ile Arg Val Thr His Glu His Asp Ile
225                 230                 235                 240

Val Pro His Leu Pro Pro Tyr Phe Phe Phe Leu Pro His Leu Thr Tyr
                245                 250                 255

His His Phe Pro Arg Glu Val Trp Glu His Asp Val Asp Gly Ser Xaa
                260                 265                 270

Xaa Xaa Xaa Thr Thr Phe Arg Val Cys Asp Asp Ser Gly Glu Asp Pro
        275                 280                 285

Asp Cys Cys Arg Ser Val Phe Ala Leu Phe Leu Ser Ala Ser Asp His
        290                 295                 300

Leu Thr Tyr Met Gly Val Glu Ile Ala Ala Asp Asp Trp Ser Thr Cys
305                 310                 315                 320

Arg Ile Val Met Ala Gln Ser Val Glu Arg Leu Gln Leu Tyr Leu Pro
                325                 330                 335

Ser Asn Val Ile Thr Ser Lys Asn Pro Val Asp Ile Ile Ala Asp
                340                 345                 350

His Ser Val Gln Thr Tyr Pro Ser Ser Ser Ser
                355                 360

<210> SEQ ID NO 46
<211> LENGTH: 357
<212> TYPE: PRT
<213> ORGANISM: Triticum aestivum
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (290)..(291)
<223> OTHER INFORMATION: Xaa can be any naturally occurring amino acid
<220> FEATURE:
<221> NAME/KEY: misc_feature
<222> LOCATION: (343)..(345)
<223> OTHER INFORMATION: Xaa can be any naturally occurring amino acid

<400> SEQUENCE: 46

Met Glu Arg Arg Gly Leu Leu Lys Ala Ala Leu Leu Ala Ser Cys Leu
1               5                   10                  15

Leu Val Val Cys Ser Gly Arg Val Pro Thr Val Ile Gln Gln Xaa Xaa
                20                  25                  30

Pro Ser Thr Thr Ile Tyr Asn Ser Thr Leu Ala Lys Thr Leu Val Glu
                35                  40                  45

Tyr Ala Ala Ala Val Ser Thr Ala Asp Leu Thr Gln Leu Phe Thr Trp
```

```
                    50                  55                  60
Thr Cys Asp Arg Cys Gly Asp Leu Ile Glu Gly Phe Glu Met Met Asp
 65                  70                  75                  80

Ile Ile Val Asp Val Glu Asn Cys Leu Glu Ala Tyr Val Gly Phe Ala
                     85                  90                  95

Ser Asp Ile Asn Ala Val Val Val Phe Arg Gly Thr Gln Glu Asn
                100                 105                 110

Ser Ile Gln Asn Trp Ile Glu Asp Leu Leu Trp Lys Gln Leu Asp Leu
                115                 120                 125

Asp Tyr Pro Gly Met Pro Glu Ala Met Val His Arg Gly Phe Tyr Ser
                130                 135                 140

Ala Tyr His Asn Thr Thr Ile Arg Asp Gly Ile Val Ser Gly Ile Gln
145                 150                 155                 160

Lys Thr Gln Lys Leu His Gly Asp Val Pro Ile Met Val Thr Gly His
                165                 170                 175

Ser Met Gly Ala Ala Met Ala Ser Phe Cys Ala Leu Asp Leu Val Val
                180                 185                 190

Asn Tyr Gly Leu Asp Asp Val Lys Leu Met Thr Phe Gly Gln Pro Arg
                195                 200                 205

Val Gly Asn Ala Ala Phe Ala Ser Tyr Phe Lys Arg Tyr Leu Pro His
                210                 215                 220

Ala Ile Arg Val Thr Asn Ala Asn Asp Ile Val Pro His Leu Pro Pro
225                 230                 235                 240

Tyr Phe Ser Phe Phe Pro Gln Lys Thr Tyr His His Phe Pro Arg Glu
                245                 250                 255

Val Trp Val His Asp Val Gly Leu Gly Ser Leu Val Tyr Thr Val Glu
                260                 265                 270

Gln Ile Cys Asp Asp Ser Gly Glu Asp Pro Ala Cys Ser Arg Ser Val
                275                 280                 285

Ser Xaa Xaa Gly Asn Ser Ile Gln Asp His Ile Thr Tyr Leu Gly Val
                290                 295                 300

Ser Met His Ala Glu Ala Trp Ser Ser Cys Arg Ile Val Met Asp Tyr
305                 310                 315                 320

Ala Glu Leu Arg Tyr Lys Met Asp Leu His Gly Asn Val Val Leu Ser
                325                 330                 335

Lys Gln Gln Gln Ser Xaa Xaa Xaa Gly Leu Ser Asn Glu Arg Arg
                340                 345                 350

Arg His Ser Ala Gln
                355

<210> SEQ ID NO 47
<211> LENGTH: 357
<212> TYPE: PRT
<213> ORGANISM: Triticum aestivum
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (290)..(291)
<223> OTHER INFORMATION: Xaa can be any naturally occurring amino acid

<400> SEQUENCE: 47
```

Met Glu Arg Arg Ala Leu Leu Lys Thr Thr Leu Leu Ala Xaa Cys Leu
1               5                   10                  15

Leu Val Val Cys Ser Gly Arg Val Pro Met Val Ile Gln Gln Xaa Xaa
            20                  25                  30

Pro Ser Thr Thr Ile Tyr Asn Ser Thr Leu Ala Lys Thr Leu Val Glu
            35                  40                  45

Tyr Ala Ala Ile Tyr Thr Ala Asp Leu Thr Gln Leu Phe Thr Trp
50                  55                  60

Thr Cys Asp Arg Cys Gly Asp Leu Ile Glu Gly Phe Glu Met Met Asp
65                  70                  75                  80

Ile Ile Val Asp Val Glu Asn Cys Leu Glu Ala Tyr Val Gly Phe Ala
                85                  90                  95

Ser Asp Ile Asn Ala Val Ile Val Val Phe Arg Gly Thr Gln Glu Asn
            100                 105                 110

Ser Ile Gln Asn Trp Ile Glu Asp Leu Leu Trp Lys Gln Leu Asp Leu
            115                 120                 125

Asp Tyr Pro Gly Met Pro Glu Ala Met Val His Arg Gly Phe Tyr Ser
130                 135                 140

Ala Tyr His Asn Thr Thr Ile Arg Asp Gly Ile Val Ser Gly Ile Gln
145                 150                 155                 160

Lys Thr Arg Lys Leu His Gly Asp Val Pro Ile Met Val Thr Gly His
                165                 170                 175

Ser Met Gly Ala Ala Met Ala Ser Phe Cys Ala Leu Asp Leu Val Val
            180                 185                 190

Asn Tyr Gly Leu Asp Asp Val Lys Leu Met Thr Phe Gly Gln Pro Arg
            195                 200                 205

Val Gly Asn Ala Ala Phe Ala Ser Tyr Phe Lys Arg Tyr Leu Pro His
210                 215                 220

Ala Ile Arg Val Thr Asn Ala Asn Asp Ile Val Pro His Leu Pro Pro
225                 230                 235                 240

Tyr Phe Ser Phe Phe Pro Gln Lys Thr Tyr His His Phe Pro Arg Glu
                245                 250                 255

Val Trp Val His Asp Val Gly Leu Gly Ser Leu Val Tyr Thr Val Glu
            260                 265                 270

Gln Ile Cys Asp Asp Ser Gly Glu Asp Pro Ala Cys Ser Arg Ser Val
            275                 280                 285

Ser Xaa Xaa Gly Asn Ser Ile Gln Asp His Ile Thr Tyr Leu Gly Val
    290                 295                 300

Ser Met His Ala Glu Ala Trp Ser Ser Cys Arg Ile Val Met Asp Tyr
305                 310                 315                 320

Ala Glu Leu Arg Tyr Lys Met Asp Leu His Gly Asn Val Val Leu Ser
                325                 330                 335

Lys Gln Gln Gln Gln Gln Gln Pro Gly Leu Ser Asp Gln Arg Arg
            340                 345                 350

Arg His Ser Ala Gln
        355

<210> SEQ ID NO 48
<211> LENGTH: 369
<212> TYPE: PRT
<213> ORGANISM: Triticum aestivum
<220> FEATURE:
<221> NAME/KEY: misc_feature
<222> LOCATION: (1)..(12)
<223> OTHER INFORMATION: Xaa can be any naturally occurring amino acid
<220> FEATURE:

```
<221> NAME/KEY: misc_feature
<222> LOCATION: (16)..(20)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (37)..(38)
<223> OTHER INFORMATION: Xaa can be any naturally occurring amino acid
<220> FEATURE:
<221> NAME/KEY: misc_feature
<222> LOCATION: (41)..(46)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (104)..(105)
<223> OTHER INFORMATION: Xaa can be any naturally occurring amino acid
<220> FEATURE:
<221> NAME/KEY: misc_feature
<222> LOCATION: (110)..(110)
<223> OTHER INFORMATION: Xaa can be any naturally occurring amino acid
<220> FEATURE:
<221> NAME/KEY: misc_feature
<222> LOCATION: (114)..(115)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
```

```
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid
<220> FEATURE:
<221> NAME/KEY: misc_feature
<222> LOCATION: (155)..(155)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (171)..(172)
<223> OTHER INFORMATION: Xaa can be any naturally occurring amino acid
<220> FEATURE:
<221> NAME/KEY: misc_feature
<222> LOCATION: (181)..(183)
<223> OTHER INFORMATION: Xaa can be any naturally occurring amino acid
<220> FEATURE:
<221> NAME/KEY: misc_feature
<222> LOCATION: (204)..(206)
<223> OTHER INFORMATION: Xaa can be any naturally occurring amino acid
<220> FEATURE:
<221> NAME/KEY: misc_feature
<222> LOCATION: (209)..(210)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (231)..(232)
<223> OTHER INFORMATION: Xaa can be any naturally occurring amino acid
<220> FEATURE:
<221> NAME/KEY: misc_feature
<222> LOCATION: (236)..(236)
<223> OTHER INFORMATION: Xaa can be any naturally occurring amino acid
<220> FEATURE:
<221> NAME/KEY: misc_feature
<222> LOCATION: (243)..(243)
<223> OTHER INFORMATION: Xaa can be any naturally occurring amino acid
<220> FEATURE:
<221> NAME/KEY: misc_feature
<222> LOCATION: (257)..(257)
<223> OTHER INFORMATION: Xaa can be any naturally occurring amino acid
<220> FEATURE:
<221> NAME/KEY: misc_feature
<222> LOCATION: (259)..(260)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (277)..(281)
<223> OTHER INFORMATION: Xaa can be any naturally occurring amino acid
<220> FEATURE:
<221> NAME/KEY: misc_feature
<222> LOCATION: (286)..(286)
```

```
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
<220> FEATURE:
<221> NAME/KEY: misc_feature
<222> LOCATION: (302)..(305)
<223> OTHER INFORMATION: Xaa can be any naturally occurring amino acid
<220> FEATURE:
<221> NAME/KEY: misc_feature
<222> LOCATION: (307)..(307)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (314)..(314)
<223> OTHER INFORMATION: Xaa can be any naturally occurring amino acid
<220> FEATURE:
<221> NAME/KEY: misc_feature
<222> LOCATION: (317)..(317)
<223> OTHER INFORMATION: Xaa can be any naturally occurring amino acid
<220> FEATURE:
<221> NAME/KEY: misc_feature
<222> LOCATION: (319)..(319)
<223> OTHER INFORMATION: Xaa can be any naturally occurring amino acid
<220> FEATURE:
<221> NAME/KEY: misc_feature
<222> LOCATION: (321)..(321)
<223> OTHER INFORMATION: Xaa can be any naturally occurring amino acid
<220> FEATURE:
<221> NAME/KEY: misc_feature
<222> LOCATION: (329)..(329)
<223> OTHER INFORMATION: Xaa can be any naturally occurring amino acid
<220> FEATURE:
<221> NAME/KEY: misc_feature
<222> LOCATION: (337)..(339)
<223> OTHER INFORMATION: Xaa can be any naturally occurring amino acid
<220> FEATURE:
<221> NAME/KEY: misc_feature
<222> LOCATION: (342)..(342)
<223> OTHER INFORMATION: Xaa can be any naturally occurring amino acid
<220> FEATURE:
<221> NAME/KEY: misc_feature
<222> LOCATION: (345)..(347)
<223> OTHER INFORMATION: Xaa can be any naturally occurring amino acid
<220> FEATURE:
<221> NAME/KEY: misc_feature
<222> LOCATION: (350)..(351)
<223> OTHER INFORMATION: Xaa can be any naturally occurring amino acid
<220> FEATURE:
<221> NAME/KEY: misc_feature
<222> LOCATION: (353)..(359)
<223> OTHER INFORMATION: Xaa can be any naturally occurring amino acid
<220> FEATURE:
<221> NAME/KEY: misc_feature
<222> LOCATION: (361)..(362)
<223> OTHER INFORMATION: Xaa can be any naturally occurring amino acid
<220> FEATURE:
<221> NAME/KEY: misc_feature
<222> LOCATION: (364)..(365)
<223> OTHER INFORMATION: Xaa can be any naturally occurring amino acid
<220> FEATURE:
<221> NAME/KEY: misc_feature
<222> LOCATION: (369)..(369)
<223> OTHER INFORMATION: Xaa can be any naturally occurring amino acid

<400> SEQUENCE: 48

Xaa Xaa Xaa Xaa Xaa Xaa Xaa Xaa Xaa Xaa Xaa Met Glu Arg Xaa
1               5                   10                  15

Xaa Xaa Xaa Xaa Val Leu Ala Leu Xaa Leu Leu Leu Leu Xaa Xaa Cys
            20                  25                  30

Xaa Gly Arg Arg Xaa Xaa Ser Val Xaa Xaa Xaa Xaa Xaa Xaa Thr Xaa
```

```
                35                  40                  45
Ile Xaa Asn Xaa Thr Leu Ala Lys Thr Ile Val Glu Tyr Ala Ser Ala
        50                  55                  60

Xaa Tyr Met Thr Asp Leu Thr Ala Leu Xaa Thr Trp Thr Cys Ser Arg
 65              70                  75                  80

Cys Asn Asp Leu Thr Xaa Gly Phe Glu Met Arg Xaa Ile Ile Val Asp
                 85                  90                  95

Xaa Xaa Asn Cys Leu Xaa Ala Xaa Xaa Gly Val Asp His Xaa Ile Asn
            100                 105                 110

Ala Xaa Xaa Val Ala Ile Arg Gly Thr Gln Glu Asn Ser Val Gln Asn
        115                 120                 125

Gln Ile Lys Asp Leu Val Trp Lys Gln Ile Asp Leu Xaa Tyr Pro Xaa
        130                 135                 140

Met Pro Xaa Ala Lys Val His Xaa Gly Phe Xaa Ser Ala Tyr Asn Asn
145                 150                 155                 160

Thr Xaa Ile Arg Xaa Ala Thr Thr Ser Ala Xaa Xaa Lys Ala Arg Lys
                165                 170                 175

Ile Tyr Gly Asp Xaa Xaa Xaa Ile Val Thr Gly His Ser Met Gly Gly
                180                 185                 190

Ala Asn Ala Ser Phe Cys Ala Leu Asp Leu Ala Xaa Xaa Xaa Gly Ser
        195                 200                 205

Xaa Xaa Val Xaa Leu Met Thr Phe Gly Gln Pro Arg Xaa Gly Asn Ala
        210                 215                 220

Ala Phe Ala Ser Tyr Phe Xaa Xaa Tyr Val Pro Xaa Ala Ile Arg Val
225                 230                 235                 240

Thr His Xaa His Asp Ile Val Pro His Leu Pro Pro Tyr Phe Ser Phe
                245                 250                 255

Xaa Pro Xaa Xaa Thr Tyr His His Phe Pro Arg Glu Val Trp Xaa His
            260                 265                 270

Xaa Val Asp Gly Xaa Xaa Xaa Xaa Thr Thr Glu Gln Xaa Cys Asp
        275                 280                 285

Asp Ser Gly Glu Asp Pro Xaa Cys Cys Arg Ser Val Ser Xaa Xaa Xaa
        290                 295                 300

Xaa Ser Xaa Gln Asp His Xaa Thr Tyr Xaa Gly Val Xaa Met Xaa Ala
305                 310                 315                 320

Xaa Asp Trp Ser Thr Cys Arg Ile Xaa Met Ala Gln Ser Val Glu Arg
                325                 330                 335

Xaa Xaa Xaa Asp Leu Xaa Ser Asn Xaa Xaa Xaa Ser Lys Xaa Xaa Val
            340                 345                 350

Xaa Xaa Xaa Xaa Xaa Xaa Xaa Ser Xaa Xaa Thr Xaa Xaa Ser Ser Ser
        355                 360                 365

Xaa
```

PLANTS WITH REDUCED LIPASE 1 ACTIVITY

CROSS REFERENCE TO RELATED APPLICATIONS

This application is a divisional of U.S. patent application Ser. No. 16/653,288, filed Oct. 15, 2019, which issued as U.S. Pat. No. 11,116,227 on Sep. 14, 2021, which is a continuation of U.S. patent application Ser. No. 15/624,974, filed Jun. 16, 2017, which issued as U.S. Pat. No. 10,463,051 on Nov. 5, 2019, which claims priority to and is a non-provisional application of U.S. Provisional Patent Application Ser. No. 62/351,584 filed Jun. 17, 2016, all of which are incorporated herein by reference in their entirety.

FIELD

In one embodiment, the disclosure relates to a plant gene associated with shelf-life stability, rancidity and improved flavor of a plant product. In another embodiment, the disclosure relates to altering the expression or activity of one or more Lipase 1 (Lip1) genes in a plant. In one embodiment, the disclosure relates to human-induced non-transgenic mutations in one or more Lip1 genes of plants, including but not limited to wheat and rice.

SUBMISSION OF SEQUENCE LISTING

The contents of the electronic submission of the text file Sequence Listing, which is titled ARC-39563.txt, which was created Apr. 9, 2018, and is 89.0 KB in size, is incorporated herein by reference in its entirety.

BACKGROUND

Cereal crops are very important to a majority of the world's populations. For instance, wheat is the most important staple food of about two billion people (36% of the world population). Worldwide, wheat provides nearly 55% of the carbohydrates and 20% of the food calories consumed globally. It exceeds in acreage and production every other grain crop (including rice, maize, etc.) and is cultivated over a wide range of climatic conditions and the understanding of genetics and genome organization using molecular markers is of great value for genetic and plant breeding purposes.

The world's main wheat producing regions are China, India, United States, Russian Federation, France, Australia, Germany, Ukraine, Canada, Turkey, Pakistan, Argentina, Kazakhstan and United Kingdom. Most of the currently cultivated wheat varieties belong to *Triticum aestivum* L., which is known as common bread wheat and valued for bread making. The greatest portion of the wheat flour produced is used for bread making.

Bread wheat is a hexaploid, with three complete genomes termed A, B and D in the nucleus of each cell. Each of these genomes is almost twice the size of the human genome and consists of around 5,500 million nucleotides. On the other hand, durum wheat, also known as macaroni wheat or pasta wheat (*Triticum durum* or *Triticum turgidum* subsp. durum), is the major tetraploid species of wheat of commercial importance, which is widely cultivated today. Durum wheat has two complete genomes, termed the A and B genomes.

Wheat is a widely studied plant, but in some cases, development of new traits is hampered by limited genetic diversity in today's commercial wheat cultivars and also because the bread wheat genome typically has three functionally redundant copies of each gene (called homoeologs), and therefore, single gene alterations usually do not produce any readily visible phenotype such as those that have been found in diploid corn. Often in bread wheat, altered variants of all three homoeologs must be combined genetically in order to evaluate their effects.

Whole grain products present a challenge to the wheat industry because whole grain flour has a greatly reduced shelf life compared to refined flour (Doblado-Maldonado 2012). The reduced shelf life of whole grain flour is due primarily to degradation of lipids, which are the most unstable components of the milled whole grain (Pomeranz 1988; Tait and Gailliard 1998). Lipid degradation leads to the production of bitter, rancid and off flavors that negatively impact the shelf life and use of whole grain flour and products made from it. Similarly, stability and reduced shelf life are issues for the use of rice bran and products derived from it such as rice bran oil, due to the degradation of lipids.

The degradation of lipids occurs through the processes of both hydrolytic and oxidative rancidity. Lipases (EC 3.1.1.3) catalyze the hydrolysis of ester bonds in mono-, di- and tri-acylglycerides (TAG) into non-esterified or free fatty acids (FFA). Lipid degradation begins immediately upon milling whole grain flour or rice bran. Lipases have substantial enzymatic activity even at the low moisture content of milled grain (typically 10-14% for wheat) (Doblado-Maldonado 2012). Lipids can also be further degraded through autooxidation or by lipoxygenases (Lpx's). Lpx's (EC 1.13.11.12) are a class of non-heme iron-containing dioxygenases that catalyse the positional and specific dioxygenation of polyunsaturated fatty acids that contain 1,4-cis, cis pentadiene structures to produce the corresponding hydroperoxides. Following the formation of hydroperoxides, further degradation of lipids leads to the formation of smaller volatile compounds such as epoxyaldehydes, ketones, furans and lactones that cause off flavors and odors and reduce the shelf life of materials. Attempts to inactivate or reduce lipase and lipoxygenase activity in whole grain flour or rice bran by microwave, heat, vacuum, cold storage or chemical treatment have met with limited success or are very expensive to employ commercially.

Relatively few plant lipases have been characterized at the molecular and biochemical level (Seth et al. 2014 Protein Exp and Pur 95:13-21). For example, the rice genome annotation project currently has 73 genes annotated as putative lipases (Kawahara et al. (2013) *Rice* 6:4), but difficulties encountered in purification of rice lipase enzymes has hindered their characterization (Muniandy, K., et al. *The Nucleus* (2015): 1-6). Despite these difficulties, several rice bran lipolytic enzymes have been identified biochemically including Lipase I, Lipase II, a thermally stable lipase and an esterase (OsEST-b), (reviewed in Muniandy 2015 and Chuang et al. *Journal of agricultural and food chemistry* 59.5 (2011): 2019-2025). Of these enzymes, Lipase II and OsEST-b were recently purified and the rice genes coding for the enzymes have been identified (Vijayakumar and *Protein expression and purification* 88.1 (2013): 67-79; Chuang et al. 2011).

In wheat, lipase activities have been described in multiple tissues, including ungerminated wheat bran and wheat germ fractions as well as lipases produced during germination (Pomeranz, Y. *Wheat: chemistry and technology*. No. Ed. 3. American Association of Cereal Chemists, 1988). However, the genes coding for these lipases are largely uncharacterized. The present inventors have identified the Lipase 1 genes in wheat, in which the expression is located in the grain of the wheat plant.

The inventors have identified novel human induced non-transgenic Lip1 mutations and analyzed their phenotypes in plants, such as wheat and rice. With regard to wheat, since multiple Lipase genes (Lip 1, 2 and 3) are all expressed, each with one or more potential homoeologs in the A, B, and D genomes, it is unclear if altering one gene or gene family could positively affect shelf life or stability of whole grain flour in bread wheat. Mutations in the Lip1 genes in the wheat genome or rice genome provide a potential pathway for providing increased hydrolytic and oxidative stability in wheat/wheat flour and rice bran and products derived therefrom. The disclosure herein demonstrates that novel alleles in the Lip1 gene significantly improve shelf-life.

SUMMARY

In one embodiment, the disclosure relates to human-induced non-transgenic mutations in the Lip1 gene of plants. In one embodiment, the plant is a wheat plant or a rice plant.

In another embodiment, the disclosure relates to a plant, seeds, plant parts, and progeny thereof with decreased lipase activity compared to wild type plant, seeds, plant parts, and progeny thereof.

In another embodiment, the disclosure relates to a plant, seeds, plant parts, and progeny thereof with increased hydrolytic stability compared to wild type plant, seeds, plant parts, and progeny thereof.

In another embodiment, the disclosure relates to a plant, a seed, a plant part, and progeny thereof having reduced lipase activity compared to the wild type plant, wherein the reduction in lipase activity is caused by a human-induced non-transgenic mutation in one or more of the plant's Lip1 genes. In another embodiment, the Lip1 enzyme has reduced activity.

In another embodiment, the disclosure relates to a plant containing one or more mutated Lip1 genes, as well as seeds, pollen, plant parts and progeny of that plant.

In another embodiment, the disclosure relates to seeds, grain, milled grain, flour, or bran with increased hydrolytic stability from reduced Lip1 enzyme activity, which is caused by a human-induced non-transgenic mutation in one or more Lip1 genes In another embodiment, the disclosure relates to seeds, grain, milled grain, flour or bran with increased oxidative stability from reduced Lip1 enzyme activity, which is caused by a human-induced non-transgenic mutation in one or more Lip1 genes In another embodiment, the disclosure relates to seeds, grain, milled grain, flour or bran with improved sensory characteristics from reduced Lip1 enzyme activity, which is caused by a human-induced non-transgenic mutation in one or more Lip1 genes.

In one embodiment, the disclosure relates to plants having plant products, such as seeds and grains having a characteristic selected from the group consisting of increased shelf-life stability, reduced rancidity and improved flavor as a result of non-transgenic mutations in at least one of the Lip1 genes.

In one embodiment, the disclosure relates to multiple non-transgenic mutations in the Lip1 gene of a plant including but not limited to 1, 2, 3, 4, 5, 6, 7, 8, 9, 10, and greater than 10 mutations.

In one embodiment, the disclosure relates to wheat plants having wheat seeds, wheat grain and wheat flour having a characteristic selected from the group consisting of increased shelf-life stability, reduced rancidity and improved flavor as a result of non-transgenic mutations in at least one of the Lip1 genes.

In one embodiment, the disclosure relates to human-induced non-transgenic mutations in the Lip1 genes in the A, B or D genomes of a wheat plant.

In one embodiment, the disclosure relates to non-transgenic mutations in one or more Lipase1 (Lip1) genes. In one embodiment, one or more mutations are in the Lip1 gene of the A genome of wheat. In another embodiment, one or more mutations are in the Lip1 gene of the D genome of wheat. In another embodiment, one or more mutations are in the Lip1 gene of the B genome of wheat.

In one embodiment, the disclosure relates to non-transgenic mutations in the Lip-A1 gene of the A genome of wheat including but not limited to 1, 2, 3, 4, 5, 6, 7, 8, 9, 10, and greater than 10 mutations.

In one embodiment, the disclosure relates to non-transgenic mutations in the Lip-D1 gene of the D genome of wheat including but not limited to 1, 2, 3, 4, 5, 6, 7, 8, 9, 10, and greater than 10 mutations.

In one embodiment, the disclosure relates to non-transgenic mutations in the Lip-B1 gene of the B genome of wheat including but not limited to 1, 2, 3, 4, 5, 6, 7, 8, 9, 10, and greater than 10 mutations.

In another embodiment, the disclosure relates to non-transgenic mutations in the Lip-A1 gene of the A genome of wheat including but not limited to 1, 2, 3, 4, 5, 6, 7, 8, 9, 10, and non-transgenic mutations in the Lip-D1 gene of the D genome of wheat including but not limited to 1, 2, 3, 4, 5, 6, 7, 8, 9, 10, and greater than 10 mutations.

In another embodiment, the disclosure relates to non-transgenic mutations in the Lip-A1 gene of the A genome of wheat including but not limited to 1, 2, 3, 4, 5, 6, 7, 8, 9, 10, and non-transgenic mutations in the Lip-B1 gene of the B genome of wheat including but not limited to 1, 2, 3, 4, 5, 6, 7, 8, 9, 10, and greater than 10 mutations.

In another embodiment, the disclosure relates to non-transgenic mutations in the Lip-A1 gene of the A genome of wheat including but not limited to 1, 2, 3, 4, 5, 6, 7, 8, 9, 10, and non-transgenic mutations in the Lip-B1 gene of the B genome of wheat including but not limited to 1, 2, 3, 4, 5, 6, 7, 8, 9, 10, and greater than 10 mutations, and non-transgenic mutations in the Lip-D1 gene of the D genome of wheat including but not limited to 1, 2, 3, 4, 5, 6, 7, 8, 9, 10, and greater than 10 mutations.

In another embodiment, the disclosure relates to food, beverage, and food and beverage products incorporating a plant product, including but not limited to seeds, grain, milled grain, flour and bran having reduced Lip1 enzyme activity caused by a human-induced non-transgenic mutation in one or more Lip1 genes.

In another embodiment, this disclosure relates to a plant having reduced activity of one or more Lip1 enzymes compared to the wild type plants, created by the steps of obtaining plant material from a parent plant, inducing at least one mutation in at least one copy of an Lip1 gene of the plant material by treating the plant material with a mutagen to create mutagenized plant material (e.g., seeds or pollen), analyzing progeny plants to detect at least one mutation in at least one copy of a Lip1 gene, selecting progeny plants that have at least one mutation in at least one copy of an Lip1 gene, and optionally, crossing progeny plants that have at least one mutation in at least one copy of an Lip1 gene with other progeny plants that have at least one mutation in a different copy of an Lip1 gene, and repeating the cycle of identifying progeny plants having mutations and optionally crossing the progeny plants having mutations with other progeny plants having mutations to produce progeny plants with reduced Lip1 enzyme activity. In another embodiment, the method comprises growing or using the mutagenized plant material to produce progeny plants.

In another embodiment one or more mutations are in the Lip1 gene of a rice plant. In another embodiment, the disclosure relates to human-induced non-transgenic mutations in the Lip1 gene of rice and rice plants. In one embodiment, the disclosure relates to rice plants having rice seeds and bran with a characteristic selected from the group consisting of: increased shelf-life stability, increased oxidative stability, increased hydrolytic stability, reduced rancidity and improved flavor as a result of non-transgenic mutations in a Lip1 gene.

BRIEF DESCRIPTION OF THE SEQUENCE LISTING

The nucleic acid sequences listed in the accompanying sequence listing are shown using standard letter abbreviations for nucleotide bases. Only one strand of each nucleic acid sequence is shown, but the complementary strand is understood to be included by any reference to the displayed strand. In the accompanying sequence listing:

SEQ ID NO: 1 shows a *Triticum aestivum* gene for Lipase 1, A genome, Lip-A1 exons 1-10 (3,280 base pairs).
SEQ ID NO: 2 shows the Lip-A1 coding sequence of SEQ ID NO: 1 (1,060 base pairs).
SEQ ID NO: 3 shows the Lip-A1 protein sequence of SEQ ID NO. 2 (352 amino acids).
SEQ ID NO: 4 shows a *Triticum aestivum* gene for Lipase 1, D genome, Lip-D1 exons 1-10 (3,263 base pairs).
SEQ ID NO: 5 shows the Lip-D1 coding sequence of SEQ ID NO. 4 (1,056 base pairs).
SEQ ID NO: 6 shows the Lip-D1 protein sequence of SEQ ID NO. 5 (351 amino acids).
SEQ ID NO: 7 shows a *Triticum aestivum* gene for Lipase 1, B genome, Lip-B1 exons 1-10 (3,460 base pairs).
SEQ ID NO: 8 shows the Lip-B1 coding sequence of SEQ ID NO. 4 (1,059 base pairs).
SEQ ID NO: 9 shows the Lip-B1 protein sequence of SEQ ID NO. 5 (352 amino acids).
SEQ ID NOs: 10-11 show exemplary homoeolog specific TILLING primers that have proven useful in identifying useful mutations within the Lip-A1 gene sequences.
SEQ ID NOs: 12-13 show exemplary homoeolog specific TILLING primers that have proven useful in identifying useful mutations within the Lip-D1 gene sequences.
SEQ ID NOs: 14-15 show exemplary homoeolog specific TILLING primers that have proven useful in identifying useful mutations within the Lip-B1 gene sequences.
SEQ ID NOs: 16-17 show exemplary primers that have proven useful as markers for identifying intact or missing Lip-B1 locus sequences.
SEQ ID NOs: 18-19 show exemplary primers that have proven useful in expression analysis of the Lip1 genes in wheat.
SEQ ID NOs: 20-21 show exemplary primers that have proven useful in expression analysis of the Lip2 genes in wheat.
SEQ ID NOs: 22-23 show exemplary primers that have proven useful in expression analysis of the Lip3 genes in wheat.
SEQ ID NOs: 24-25 show exemplary primers that have proven useful in expression analysis of glyceraldehyde-phosphate dehydrogenase (GAPD).
SEQ ID NO: 26 shows an *Oryza sativa* gene for Lipase 1, OsLip1 exons 1-10 (3672 base pairs).
SEQ ID NO: 27 shows the OsLip1 coding region for SEQ ID NO: 26 (1,077 base pairs).
SEQ ID NO: 28 shows the OsLip1 protein sequence for SEQ ID NO: 27 (358 amino acids).
SEQ ID NOs: 29-30 show exemplary TILLING primers that have proven useful in identifying novel mutations within the OsLip1 gene sequence.
SEQ ID Nos: 31-35 show exemplary guide sequences for targeting genome editing of OsLip1.
SEQ ID NO. 36 shows the rice OsLip1 protein sequence.
SEQ ID NO. 37 shows the wheat Lip-A1 protein sequence.
SEQ ID NO. 38 shows the wheat Lip-B1 protein sequence.
SEQ ID NO. 39 shows the wheat Lip-D1 protein sequence.
SEQ ID NO. 40 shows the wheat Lip-A2 protein sequence.
SEQ ID NO. 41 shows the wheat Lip-D2 protein sequence.
SEQ ID NO. 42 shows the wheat Lip-B2.4 protein sequence.
SEQ ID NO. 43 shows the wheat Lip-B2.1 protein sequence.
SEQ ID NO. 44 shows the wheat Lip-B2.2 protein sequence.
SEQ ID NO. 45 shows the wheat Lip-B2.3 protein sequence.
SEQ ID NO. 46 shows the wheat Lip-A3 protein sequence.
SEQ ID NO. 47 shows the wheat Lip-B3 protein sequence.
SEQ ID NO. 48 shows the consensus protein sequence for the rice and wheat lipase protein sequence.

BRIEF DESCRIPTION OF THE FIGURES

FIG. 1 shows the protein alignment of rice Lipase 1 and wheat Lipases 1, 2 and 3, with SEQ ID NO. 36 showing rice lipase1 (OsLip1), SEQ ID NO. 37 showing wheat Lip-A1 protein sequence, SEQ ID NO. 38 showing wheat Lip-B1 protein sequence, SEQ ID NO. 39 showing wheat Lip-D1 protein sequence, SEQ ID NO. 40 showing wheat Lip-A2 protein sequence, SEQ ID NO. 41 showing wheat Lip-D2 protein sequence, SEQ ID NO. 42 showing wheat Lip-B2.4 protein sequence, SEQ ID NO. 43 showing wheat Lip-B2.1 protein sequence, SEQ ID NO. 44 showing wheat Lip-B2.2 protein sequence, SEQ ID NO. 45 showing wheat Lip-B2.3 protein sequence, SEQ ID NO. 46 showing wheat Lip-A3 protein sequence, SEQ ID NO. 47 showing wheat Lip-B3 protein sequence, and SEQ ID NO. 48 showing the consensus protein sequence for the rice and wheat lipase protein sequence.

DETAILED DESCRIPTION

Definitions

Figure 2:
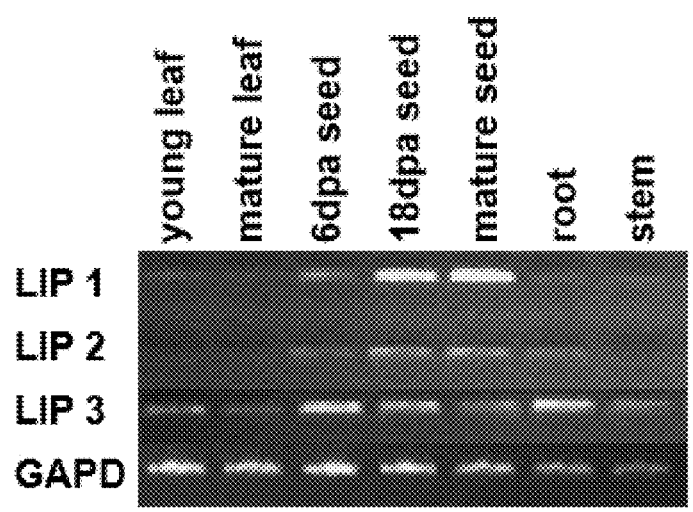
FIG. 2 shows the expression of the Lipase 1, 2 and 3 genes in various tissue types of wheat.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the term "allele" is any of one or more alternative forms of a gene, all of which relate to one trait or characteristic. In a diploid cell or organism, the two alleles of a given gene occupy corresponding loci on a pair of homologous chromosomes. An allele can be "wild-type" indicating the parental sequence at a particular nucleotide position, or "mutant" indicating a different nucleotide than the parental sequence. The term "heterozygous" indicates one wild-type and one mutant allele at a particular nucleotide position, and the term "homozygous" indicates two of the same allele at a particular nucleotide position.

As used herein, the terms "altering", "increasing", "increased", "reducing", "reduced", "inhibited" or the like are considered relative terms, i.e. in comparison with the wild-type or unaltered state. The "level of a protein" refers to the amount of a particular protein, for example Lip1, which may be measured by any means known in the art such as, for example, Western blot analysis, or mass spectrometry or other immunological means. The "level of an enzyme activity" refers to the amount of a particular enzyme measured in an enzyme assay. It would be appreciated that the level of activity of an enzyme might be altered in a mutant but not the expression level (amount) of the protein itself. Conversely, the amount of protein might be altered but the activity remain the same if a more or less active protein is produced. Reductions in both amount and activity are also possible such as, for example, when a gene encoding the enzyme is inactivated. In certain embodiments, the reduction in the level of protein or activity is by at least 10% or by at least 20% or by at least 30% or by at least 40% or by at least 50% or by at least 60% compared to the level of protein or activity in the endosperm of the unmodified plant, or by at least 70%, or by at least 80% or by at least 85% or by at least 90% or at least 95%. The reduction in the level of the protein or enzyme activity or gene expression may occur at any stage in the development of the grain, particularly during the grain filling stage, or at all stages of grain development through to maturity.

As used herein, amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443-453). Sequences may also be aligned using algorithms known in the art including but not limited to CLUSTAL V algorithm or the BLASTN or BLAST 2 sequence programs.

"Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the Blosum62 substitution matrix (Henikoff and Henikoff, 1992, Proc. Natl. Acad. Sci. USA 89: 10915-10919).

By the statement "sequence A is n % similar to sequence B," it is meant that n % of the positions of an optimal global alignment between sequences A and B consists of identical residues or nucleotides and conservative substitutions. By the statement "sequence A is n % identical to sequence B," it is meant that n % of the positions of an optimal global alignment between sequences A and B consists of identical residues or nucleotides.

As used herein, "hydrolytic stability" refers to the conversion of tri-acylglycerides (TAG) into non-esterified or free fatty acids (FFA). An increase or improvement in hydrolytic stability refers to a reduction in the rate of TAG conversion to FFA.

As used herein, "hydrolytic rancidity" refers to the odor or flavor that develops when triglycerides are hydrolyzed and free fatty acids are released. In some embodiments, rancidity in foods may be very slight, indicated by a loss of freshness. In other embodiments, rancidity in foods may be very severe, indicated by objectionable odors and/or flavors.

As used herein, "increase in shelf life" refers to an increase in the time period for which the product can remain sellable or useable. For example, millers commonly stamp 'use by' dates after milling for whole grain flour in the United States. A typical "use by" date may be four months. An "increase in shelf life" would extend the use by date as compared to a typical product. In some embodiments, an "increase in shelf life" may also refer to the reduction in accumulation of free fatty acids, or hexanal, or the reduction in objectionable flavors and odors.

As used herein, lipase is an enzyme that catalyzes the hydrolysis of fats (lipids). Lipases are a subclass of the esterases.

As used herein, "oxidative rancidity" refers to the degradation of a product by available oxygen in the air. Not to be bound by a particular theory, the double bonds of an unsaturated fatty acid can undergo cleavage, via a free radical process, releasing volatile aldehydes and ketones. Oxidation primarily occurs with unsaturated fats.

As used herein, an increase or improvement in "oxidative stability" refers to a reduction in the rate of degradation of a product by available oxygen.

As used herein, the term "plant" includes reference to an immature or mature whole plant, including a plant from which seed or grain or anthers have been removed. A seed or embryo that will produce the plant is also considered to be the plant. As used herein, the term plant encompasses cereals including but not limited to wheat and rice.

As used herein, the term "plant parts" includes plant protoplasts, plant cell tissue cultures from which plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide.

As used herein, an "Lip1 derivative" refers to a Lip1 protein/peptide/polypeptide sequence that possesses biological activity that is substantially reduced as compared to the biological activity of the whole Lip1 protein/peptide/polypeptide sequence. In other words, it refers to a polypeptide of a modified Lip1 protein that has reduced Lip1 enzymatic activity. The term "Lip11 derivative" encompasses the "fragments" or "chemical derivatives" of a modified Lip1 protein/peptide.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides," that due to mutagenesis are not 100% identical but nevertheless code for the same amino acid sequence.

A "reduced or non-functional fragment," as is used herein, refers to a nucleic acid sequence that encodes for a Lip1 protein that has reduced biological activity as compared the protein coding of the whole nucleic acid sequence. In other words, it refers to a nucleic acid or fragment(s) thereof that substantially retains the capacity of encoding a Lip1 polypeptide of the invention, but the encoded Lip1 polypeptide has reduced activity.

The term "fragment," as used herein, refers to a polynucleotide sequence, (e.g., a PCR fragment) which is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

With reference to polynucleotides of the disclosure, the term "isolated polynucleotide" is sometimes used. This term, when applied to DNA, refers to a DNA molecule that is separated from sequences with which it is immediately contiguous (in the 5' and 3' directions) in the naturally occurring genome of the organism from which it was derived. For example, the "isolated polynucleotide" may comprise a PCR fragment.

In another embodiment, the "isolated polynucleotide" may comprise a DNA molecule inserted into a vector, such as a plasmid or virus vector, or integrated into the genomic DNA of a prokaryote or eukaryote. An "isolated polynucleotide molecule" may also comprise a cDNA molecule.

In another embodiment, the term "isolated polynucleotide" may comprise RNA. In another embodiment, the term "isolated polynucleotide" may comprise exome captured DNA (King, Robert, et al. Mutation Scanning in Wheat by Exon Capture and Next-Generation Sequencing. *PloS one* 10.9 (2015): e0137549).

A wheat plant is defined herein as any plant of a species of the genus *Triticum*, which species is commercially cultivated, including, for example, *Triticum aestivum* L. ssp. *aestivum* (common or bread wheat), other subspecies of *Triticum aestivum, Triticum turgidum* L. ssp. durum (durum wheat, also known as macaroni or hard wheat), *Triticum monococcum* L. ssp. *monococcum* (cultivated einkorn or small spelt), *Triticum timopheevi* ssp. *timopheevi, Triticum turgigum* L. ssp. *dicoccon* (cultivated emmer), and other subspecies of *Triticum turgidum* (Feldman). The wheat may be hexaploid wheat having an AABBDD type genome, or tetraploid wheat having an AABB type genome. Since genetic variation in wheat transferred to certain related species, including rye and barley by hybridization, the disclosure also includes the hybrid species thus formed, including triticale that is a hybrid between bread wheat and rye. In one embodiment, the wheat plant is of the species *Triticum aestivum*, and preferably of the subspecies *aestivum*. Alternatively, since mutations or transgenes can be readily transferred from *Triticum aestivum* to durum wheat, the wheat is preferably *Triticum turgidum* L. ssp. Durum.

A rice plant is defined herein as any plant of a species of the genus *Oryza*, which species is commercially cultivated, including, for example, *Oryza sativa L. indica* and *Oryza sativa L. japonica* and other species such as *Oryza sativa* L. tropical japonica *Oryza rufipogon*. In one embodiment, the rice plant is of the species *Oryza sativa*, and preferably of the subspecies indica. Mutations or transgenes can be readily transferred from *Oryza sativa* indica to japonica and other rice species.

In one embodiment, the disclosure relates to non-transgenic mutations in one or more Lip1 genes of a plant. In another embodiment, the disclosure describes plants exhibiting seeds with deceased Lip1 activity as compared to wild type seeds without the inclusion of foreign nucleic acids in the plant genome. In yet another embodiment, the disclosure describes plants exhibiting seeds with increased oxidative stability as compared to wild type seeds, without the inclusion of foreign nucleic acids in the plant genome. In yet another embodiment, the disclosure describes plants exhibiting seeds with increased hydrolytic stability as compared to wild type seeds, without the inclusion of foreign nucleic acids in the plant genome.

In yet another embodiment, the disclosure describes plants exhibiting seeds producing flour and/or bran with increased shelf life as compared to wild type seeds, without the inclusion of foreign nucleic acids in the wheat plant genome.

In still another embodiment, the disclosure relates to a series of independent human-induced non-transgenic mutations in one or more Lip1 genes of a plant; plants having one or more of these mutations in at least one Lip1 gene thereof, and a method of creating and identifying similar and/or additional mutations in at least one Lip1 gene of a plant. Additionally, the disclosure relates to plants exhibiting plant products with decreased Lip1 activity and/or increased oxidative stability and/or increased hydrolytic stability and/or shelf life as compared to wild type plant products without the inclusion of foreign nucleic acids in the plants' genomes.

I. Lip1 Mutations

A. Lip1 Genes

In one embodiment, the disclosure relates to one or more non-transgenic mutations in the Lip1 gene of a plant. In one embodiment, the disclosure relates to multiple non-transgenic mutations in the Lip1 gene of a plant including but not limited to 1, 2, 3, 4, 5, 6, 7, 8, 9, 10, and greater than 10 mutations.

In another embodiment, the Lip1 gene of a plant may contain one or more non-transgenic mutations recited in Tables 1, 2, 3, and 4 and corresponding mutations in homoeologues and combinations thereof.

In another embodiment, the disclosure relates to corresponding mutations to the one or more non-transgenic mutations disclosed herein in the Lip1 gene in a corresponding homoeologue. By way of example, an identified mutation in the Lip-A1 gene of the A genome of a wheat plant may be a beneficial mutation in the Lip1 gene of the B and/or D genome. One of ordinary skill in the art will understand that the mutation in the homoeologue may not be in the exact location.

One of ordinary skill in the art understands there is natural variation in the genetic sequences of the Lip1 genes in different varieties of a specific plant.

1. Wheat Plants

The inventors have determined mutations that reduce Lip1 gene function are desired in order to improve the shelf of wheat products, including but not limited to wheat whole grain flour. Preferred mutations include missense and nonsense changes, including mutations that prematurely truncate the translation of one or more Lip1 proteins from messenger RNA, such as those mutations that create a stop codon within the coding region of an Lip1 messenger RNA. Such mutations include insertions, deletions, repeat sequences, splice junction mutations, modified open reading frames (ORFs) and point mutations. Some stop codon mutations are more effective than others because not all stop codon mutations reduce lipase activity to the same extent.

In still another embodiment, one or more mutations are in the Lip-A1 gene of the A genome. In still another embodiment, one or more mutations are in the Lip-D1 gene of the D genome. In another embodiment, one or more mutations are in the Lip-A1 and Lip-D1 genes of the A and D genomes.

In still another embodiment, one or more mutations are in the Lip-A1 gene of the A genome. In still another embodiment, one or more mutations are in the Lip-B1 gene of the B genome. In another embodiment, one or more mutations are in the Lip-A1 and Lip-B1 genes of the A and B genomes.

a. A Genome

In one embodiment, the disclosure relates to multiple non-transgenic mutations in the Lip1 gene of the A genome including but not limited to 1, 2, 3, 4, 5, 6, 7, 8, 9, 10, and greater than 10 mutations. In one embodiment, one or more non-transgenic mutations are in both alleles of the Lip1 gene in the A genome. In another embodiment, the non-transgenic mutations are identical in both alleles of the Lip1 gene of the A genome.

The following mutations identified in Tables 1, 2, 3, and 4 are exemplary of the mutations created and identified according to various embodiments disclosed herein. They are offered by way of illustration, not limitation. It is to be understood that the mutations below are merely exemplary and that similar mutations are also contemplated.

One exemplary mutation in Table 1 is G2141A, resulting in a change from guanine (wild-type allele) to adenine (mutant allele) at nucleotide position 2141 identified according to its position in the sequence of Lip-A1 SEQ ID NO: 1. This mutation results in a change from a tryptophan to a stop (*) codon at amino acid position 122 (W122*) identified according to its position in the expressed protein of Lip-A1 (SEQ ID NO: 3).

Table 1 provides examples of mutations created and identified in Lip-A1 in the A genome of wheat plants, variety Express. Nucleotide and amino acid changes are identified according to their positions in SEQ ID NOs: 1 and 3, respectively.

TABLE 1

Representative mutation alleles in the Lip-A1 gene in the A genome

| Primer SEQ ID NOs | Line | Gene | Nucleotide Mutation (SEQ ID NO: 1) | A.A Mutation (SEQ ID NO: 3) |
|---|---|---|---|---|
| 10, 11 | 1 | Lip-A1 | C1970T | A104V |
| 10, 11 | 2 | Lip-A1 | C2328T | A153V |
| 10, 11 | 3 | Lip-A1 | C2352T | A161V |
| 10, 11 | 4 | Lip-A1 | C2682T | A214V |
| 10, 11 | 5 | Lip-A1 | G1927A | A90T |
| 10, 11 | 6 | Lip-A1 | C1928T | A90V |
| 10, 11 | 7 | Lip-A1 | G1942A | A95T |
| 10, 11 | 8 | Lip-A1 | G1519A | C65Y |
| 10, 11 | 9 | Lip-A1 | G1791A | C87Y |
| 10, 11 | 10 | Lip-A1 | G1319A | D38N |
| 10, 11 | 11 | Lip-A1 | G1491A | D56N |
| 10, 11 | 12 | Lip-A1 | G1987A | E110K |
| 10, 11 | 13 | Lip-A1 | G2931A | E267K |
| 10, 11 | 14 | Lip-A1 | G2289A | G140E |
| 10, 11 | 15 | Lip-A1 | G2402A | G178R |
| 10, 11 | 16 | Lip-A1 | G2406A | G179E |
| 10, 11 | 17 | Lip-A1 | G2405A | G179R |
| 10, 11 | 18 | Lip-A1 | G2730A | G230E |
| 10, 11 | 19 | Lip-A1 | C2747T | H236Y |
| 10, 11 | 20 | Lip-A1 | C2789T | H250Y |
| 10, 11 | 21 | Lip-A1 | C2148T | L125F |
| 10, 11 | 22 | Lip-A1 | C2435T | L189F |
| 10, 11 | 23 | Lip-A1 | C1328T | L41F |
| 10, 11 | 24 | Lip-A1 | C2163T | P130S |
| 10, 11 | 25 | Lip-A1 | C2172T | P133S |
| 10, 11 | 26 | Lip-A1 | C2705T | P222S |
| 10, 11 | 27 | Lip-A1 | C2754T | P238L |
| 10, 11 | 28 | Lip-A1 | C2756T | P239S |
| 10, 11 | 29 | Lip-A1 | G2322A | R151H |
| 10, 11 | 30 | Lip-A1 | G2355A | R162K |
| 10, 11 | 31 | Lip-A1 | G2718A | R226Q |
| 10, 11 | 32 | Lip-A1 | G2802A | R254K |
| 10, 11 | 33 | Lip-A1 | G1764A | R78K |
| 10, 11 | 34 | Lip-A1 | G2158A | S128N |
| 10, 11 | 35 | Lip-A1 | C2298T | S143F |
| 10, 11 | 36 | Lip-A1 | G2625A | S195N |
| 10, 11 | 37 | Lip-A1 | C2914T | S261F |
| 10, 11 | 38 | Lip-A1 | G2184A | Splice Junction |
| 10, 11 | 39 | Lip-A1 | G2807A | Splice Junction |
| 10, 11 | 40 | Lip-A1 | G1799A | Splice Junction |
| 10, 11 | 41 | Lip-A1 | C2313T | T148I |
| 10, 11 | 42 | Lip-A1 | C2361T | T164I |
| 10, 11 | 43 | Lip-A1 | G2136A | V121I |
| 10, 11 | 44 | Lip-A1 | G2633A | V198I |

TABLE 1-continued

Representative mutation alleles in the Lip-A1 gene in the A genome

| Primer SEQ ID NOs | Line | Gene | Nucleotide Mutation (SEQ ID NO: 1) | A.A Mutation (SEQ ID NO: 3) |
|---|---|---|---|---|
| 10, 11 | 45 | Lip-A1 | G2723A | V228I |
| 10, 11 | 46 | Lip-A1 | G1781A | V84M |
| 10, 11 | 47 | Lip-A1 | G2140A | W122* |
| 10, 11 | 48 | Lip-A1 | G2141A | W122* |
| 10, 11 | 49 | Lip-A1 | G2902A | W257* |
| 10, 11 | 50 | Lip-A1 | G2903A | W257* |
| 10, 11 | 51 | Lip-A1 | G1514A | W63* |

In one embodiment, the disclosure relates to a polynucleotide of the Lip1-A1 gene in the A genome with one or more non-transgenic mutations listed in Table 1 and corresponding to SEQ ID NO: 1. In another embodiment, the polynucleotide with one or more non-transgenic mutations listed in Table 1 is 85%, 86%, 87%, 88%, 89%, 90%, 91%, 92%, 93%, 94%, 95%, 96%, 97%, 98%, 99% or greater than 99% identical to SEQ ID NO: 1. In yet another embodiment, the polynucleotide with one or more non-transgenic mutations listed in Table 1 is 85%, 86%, 87%, 88%, 89%, 90%, 91%, 92%, 93%, 94%, 95%, 96%, 97%, 98%, 99% or greater than 99% similar to SEQ ID NO: 1.

In still another embodiment, the polynucleotide with one or more non-transgenic mutation listed in Table 1 codes for a Lip-A1 protein, wherein the Lip-A1 protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 3. In still another embodiment, the polynucleotide with one or more non-transgenic mutation listed in Table 1 codes for a Lip-A1 protein, wherein the Lip-A1 protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 3.

b. D Genome

In one embodiment, the disclosure relates to multiple non-transgenic mutations in the Lip-D1 gene of the D genome including but not limited to 1, 2, 3, 4, 5, 6, 7, 8, 9, 10, and greater than 10 mutations. In one embodiment, one or more non-transgenic mutations are in both alleles of the Lip-D1 gene in the D genome. In another embodiment, the non-transgenic mutations are identical in both alleles of the Lip-D1 gene of the D genome.

In one embodiment, one or more mutations are in the Lip-D1 gene of the D genome. In one embodiment, the disclosure relates to multiple non-transgenic mutations in the Lip-D1 gene including but not limited to 1, 2, 3, 4, 5, 6, 7, 8, 9, 10, and greater than 10 mutations.

One exemplary mutation in Table 2 is C1780T, resulting in a change from cytosine in the wild-type sequence to a thymine in the mutant sequence at nucleotide position 1780 identified according to its position in the sequence of Lip-D1 SEQ ID NO: 4. This mutation results in a change of a glutamate to a stop (*) codon at amino acid position 88 (Q88*) identified according to its position in the expressed Lip-D1 protein (SEQ ID NO: 6).

Table 2 provides representative examples of mutations created and identified in Lip-D1 in the D genome of wheat plants, variety Express. Nucleotide and amino acid changes are identified according to their positions in SEQ TD NOs: 4 and 6, respectively.

TABLE 2

Representative mutation alleles in the Lip-D1 gene in the D genome

| Primer SEQ ID NOs | Line | Gene | Nucleotide Mutation (SEQ ID NO: 4) | A.A Mutation (SEQ ID NO: 6) |
|---|---|---|---|---|
| 12, 13 | 1 | Lip-D1 | G2162A | A134T |
| 12, 13 | 2 | Lip-D1 | G2310A | A152T |
| 12, 13 | 3 | Lip-D1 | C2323T | A156V |
| 12, 13 | 4 | Lip-D1 | C2398T | A181V |
| 12, 13 | 5 | Lip-D1 | C2401T | A182V |
| 12, 13 | 6 | Lip-D1 | G2421A | A189T |
| 12, 13 | 7 | Lip-D1 | C2663T | A213V |
| 12, 13 | 8 | Lip-D1 | C2675T | A217V |
| 12, 13 | 9 | Lip-D1 | G1337A | A48T |
| 12, 13 | 10 | Lip-D1 | G1343A | A50T |
| 12, 13 | 11 | Lip-D1 | G1512A | C67Y |
| 12, 13 | 12 | Lip-D1 | G1775A | C86Y |
| 12, 13 | 13 | Lip-D1 | G2352A | D166N |
| 12, 13 | 14 | Lip-D1 | G1735A | D73N |
| 12, 13 | 15 | Lip-D1 | G1971A | E109K |
| 12, 13 | 16 | Lip-D1 | G1331A | E46K |
| 12, 13 | 17 | Lip-D1 | G1768A | E84K |
| 12, 13 | 18 | Lip-D1 | G2350A | G165E |
| 12, 13 | 19 | Lip-D1 | G2374A | G173E |
| 12, 13 | 20 | Lip-D1 | G2373A | G173R |
| 12, 13 | 21 | Lip-D1 | G2385A | G177R |
| 12, 13 | 22 | Lip-D1 | G2602A | G193R |
| 12, 13 | 23 | Lip-D1 | G2633A | G203E |
| 12, 13 | 24 | Lip-D1 | G2648A | G208D |
| 12, 13 | 25 | Lip-D1 | C2728T | H235Y |
| 12, 13 | 26 | Lip-D1 | C1929T | H95Y |
| 12, 13 | 27 | Lip-D1 | A2892G | I257V |
| 12, 13 | 28 | Lip-D1 | T1299C | I35T |
| 12, 13 | 29 | Lip-D1 | C2132T | L124F |
| 12, 13 | 30 | Lip-D1 | C2599T | L192F |
| 12, 13 | 31 | Lip-D1 | C2620T | L199F |
| 12, 13 | 32 | Lip-D1 | C1295T | L34F |
| 12, 13 | 33 | Lip-D1 | C1313T | L40F |
| 12, 13 | 34 | Lip-D1 | G2384A | M176I |
| 12, 13 | 35 | Lip-D1 | G1471A | M53I |
| 12, 13 | 36 | Lip-D1 | C2147T | P129S |
| 12, 13 | 37 | Lip-D1 | C2156T | P132S |
| 12, 13 | 38 | Lip-D1 | C2686T | P221S |
| 12, 13 | 39 | Lip-D1 | C2779T | P252S |
| 12, 13 | 40 | Lip-D1 | C1780T | Q88* |
| 12, 13 | 41 | Lip-D1 | C2304T | R150C |
| 12, 13 | 42 | Lip-D1 | G2338A | R161K |
| 12, 13 | 43 | Lip-D1 | C2641T | R206C |
| 12, 13 | 44 | Lip-D1 | G1978A | S111N |
| 12, 13 | 45 | Lip-D1 | G2142A | S127N |
| 12, 13 | 46 | Lip-D1 | G2269A | S138N |
| 12, 13 | 47 | Lip-D1 | C2281T | S142F |
| 12, 13 | 48 | Lip-D1 | C2284T | S143F |
| 12, 13 | 49 | Lip-D1 | G2606A | S194N |
| 12, 13 | 50 | Lip-D1 | C2747T | S241F |
| 12, 13 | 51 | Lip-D1 | C1275T | S27F |
| 12, 13 | 52 | Lip-D1 | G1783A | Splice Junction |
| 12, 13 | 53 | Lip-D1 | G2788A | Splice Junction |
| 12, 13 | 54 | Lip-D1 | G2261A | Splice Junction |
| 12, 13 | 55 | Lip-D1 | G2885A | Splice Junction |
| 12, 13 | 56 | Lip-D1 | G2168A | Splice Junction |
| 12, 13 | 57 | Lip-D1 | G1346A | Splice Junction |
| 12, 13 | 58 | Lip-D1 | G1979A | Splice Junction |
| 12, 13 | 59 | Lip-D1 | C2627T | T201I |
| 12, 13 | 60 | Lip-D1 | C1473T | T54I |
| 12, 13 | 61 | Lip-D1 | G2683A | V220M |
| 12, 13 | 62 | Lip-D1 | G2722A | V233M |
| 12, 13 | 63 | Lip-D1 | G2107A | W115* |
| 12, 13 | 64 | Lip-D1 | G2125A | W121* |
| 12, 13 | 65 | Lip-D1 | G1498A | W62* |
| 12, 13 | 66 | Lip-D1 | G1497A | W62* |

In one embodiment, the invention relates to a polynucleotide of the Lip 1 gene in the D genome with one or more non-transgenic mutations listed in Table 2 and corresponding to SEQ ID NO: 4. In another embodiment, the polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% identical to SEQ ID NO: 4. In yet another embodiment, the polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% similar to SEQ ID NO: 4.

In still another embodiment, the polynucleotide with one or more non-transgenic mutation listed in Table 2 codes for a Lip-D1 protein, wherein the Lip-D1 protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 6. In still another embodiment, the polynucleotide with one or more non-transgenic mutation listed in Table 2 codes for a Lip-D1 protein, wherein the Lip-D1 protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 6.

c. B Genome

In one embodiment, the disclosure relates to multiple non-transgenic mutations in the Lip-B1 gene of the B genome including but not limited to 1, 2, 3, 4, 5, 6, 7, 8, 9, 10, and greater than 10 mutations. In one embodiment, one or more non-transgenic mutations are in both alleles of the Lip-B1 gene in the B genome. In another embodiment, the non-transgenic mutations are identical in both alleles of the Lip-B1 gene of the B genome.

In one embodiment, one or more mutations are in the Lip-B1 gene of the B genome. In one embodiment, the disclosure relates to multiple non-transgenic mutations in the Lip-B1 gene including but not limited to 1, 2, 3, 4, 5, 6, 7, 8, 9, 10, and greater than 10 mutations.

One exemplary mutation in Table 3 is G2299A, resulting in a change from guanine in the wild-type sequence to an adenine in the mutant sequence at nucleotide position 2299 identified according to its position in the sequence of Lip-B1 SEQ ID NO: 7. This mutation results in a change of a tryptophan to a stop (*) codon at amino acid position 116 (W116*) identified according to its position in the expressed Lip-B1 protein (SEQ ID NO: 9).

Table 3 provides representative examples of mutations created and identified in Lip-B1 in the B genome of wheat plants, variety Kronos. Nucleotide and amino acid changes are identified according to their positions in SEQ ID NOs: 7 and 9, respectively.

TABLE 3

Representative mutation alleles in the Lip-B1 gene in the B genome

| Primer SEQ ID NOs | Line | Gene | Nucleotide Mutation (SEQ ID NO: 7) | A.A Mutation (SEQ ID NO: 9) |
|---|---|---|---|---|
| 14, 15 | 1 | Lip-B1 | T1560A | Y61N |
| 14, 15 | 2 | Lip-B1 | C1599A | Splice Junction |
| 14, 15 | 3 | Lip-B1 | C1947T | S79F |
| 14, 15 | 4 | Lip-B1 | G1964A | E85K |
| 14, 15 | 5 | Lip-B1 | C2123T | A95V |
| 14, 15 | 6 | Lip-B1 | C2150T | A104V |
| 14, 15 | 7 | Lip-B1 | G2156A | R106K |
| 14, 15 | 8 | Lip-B1 | G2299A | W116* |
| 14, 15 | 9 | Lip-B1 | G2334A | S128N |
| 14, 15 | 10 | Lip-B1 | G2515A | A157T |
| 14, 15 | 11 | Lip-B1 | C2528T | A161V |
| 14, 15 | 12 | Lip-B1 | G2543A | G166E |
| 14, 15 | 13 | Lip-B1 | C2569T | H175Y |
| 14, 15 | 14 | Lip-B1 | G2578A | G178R |
| 14, 15 | 15 | Lip-B1 | G2801A | D196N |
| 14, 15 | 16 | Lip-B1 | C2813T | L200F |

TABLE 3-continued

Representative mutation alleles in the Lip-B1 gene in the B genome

| Primer SEQ ID NOs | Line | Gene | Nucleotide Mutation (SEQ ID NO: 7) | A.A Mutation (SEQ ID NO: 9) |
|---|---|---|---|---|
| 14, 15 | 17 | Lip-B1 | C2831T | P206S |
| 14, 15 | 18 | Lip-B1 | C2856T | A214V |

In one embodiment, the disclosure relates to a polynucleotide of the Lip1 gene in the B genome with one or more non-transgenic mutations listed in Table 3 and corresponding to SEQ ID NO: 7. In another embodiment, the polynucleotide with one or more non-transgenic mutations listed in Table 3 is 85%, 86%, 87%, 88%, 89%, 90%, 91%, 92%, 93%, 94%, 95%, 96%, 97%, 98%, 99% or greater than 99% identical to SEQ ID NO: 7. In yet another embodiment, the polynucleotide with one or more non-transgenic mutations listed in Table 2 is 85%, 86%, 87%, 88%, 89%, 90%, 91%, 92%, 93%, 94%, 95%, 96%, 97%, 98%, 99% or greater than 99% similar to SEQ ID NO: 7.

In still another embodiment, the polynucleotide with one or more non-transgenic mutation listed in Table 3 codes for a Lip-B1 protein, wherein the Lip-B1 protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 9. In still another embodiment, the polynucleotide with one or more non-transgenic mutation listed in Table 3 codes for a Lip-B1 protein, wherein the Lip-B1 protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 9.

2. Rice Plants

One of ordinary skill in the art understands there is natural variation in the genetic sequences of the Lip1 genes in different rice varieties. In one embodiment, one or more mutations are in the OsLip1 gene. In one embodiment, the disclosure relates to multiple non-transgenic mutations in the OsLip1 gene including but not limited to 1, 2, 3, 4, 5, 6, 7, 8, 9, 10, and greater than 10 mutations. In one embodiment, one or more non-transgenic mutations are in both alleles of the OsLip1 gene. In another embodiment, the non-transgenic mutations are identical in both alleles of the OsLip1 gene.

One exemplary mutation in Table 4 is T3424A, resulting in a change from thymine in the wild-type sequence to adenine in the mutant sequence at nucleotide position 3424 identified according to its position in the sequence of OsLip1 SEQ ID NO: 26. This mutation results in a change of a tyrosine to a stop (*) codon at amino acid position 156 (Y156*) identified according to its position in the expressed OsLip1 protein (SEQ ID NO: 28).

Table 4 provides representative examples of mutations created and identified in OsLip1 of rice plants. Nucleotide and amino acid changes are identified according to their positions in SEQ ID NOs: 26 and 28, respectively.

TABLE 4

Representative mutation alleles in the OsLip1 gene

| Primer SEQ ID NOs | Line | Gene | Nucleotide Mutation (SEQ ID NO: 26) | A.A Mutation (SEQ ID NO: 28) |
|---|---|---|---|---|
| 29, 30 | 1 | OsLip1 | A2629T | T73S |
| 29, 30 | 2 | OsLip1 | T3280C | M143T |
| 29, 30 | 3 | OsLip1 | T2358A | L46* |
| 29, 30 | 4 | OsLip1 | T2632A | W74R |
| 29, 30 | 5 | OsLip1 | T2666A | Splice Junction |
| 29, 30 | 6 | OsLip1 | A2943T | D94V |
| 29, 30 | 7 | OsLip1 | T3424A | Y156* |
| 29, 30 | 8 | OsLip1 | A3467T | K171* |

In one embodiment, the disclosure relates to a polynucleotide of the OsLip1 gene with one or more non-transgenic mutations listed in Table 4 and corresponding to SEQ ID NO: 26. In another embodiment, the polynucleotide with one or more non-transgenic mutations listed in Table 4 is 85%, 86%, 87%, 88%, 89%, 90%, 91%, 92%, 93%, 94%, 95%, 96%, 97%, 98%, 99% or greater than 99% identical to SEQ ID NO: 26.

In yet another embodiment, the polynucleotide with one or more non-transgenic mutations listed in Table 4 is 85%, 86%, 87%, 88%, 89%, 90%, 91%, 92%, 93%, 94%, 95%, 96%, 97%, 98%, 99% or greater than 99% similar to SEQ ID NO: 26.

In still another embodiment, the polynucleotide with one or more non-transgenic mutation listed in Table 4 codes for an OsLip1 protein, wherein the OsLip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical to SEQ ID NO: 28. In still another embodiment, the polynucleotide with one or more non-transgenic mutation listed in Table 4 codes for an OsLip1 protein, wherein the OsLip1 protein comprises one or more non-transgenic mutations and is 85%, 86%, 87%, 88%, 89%, 90%, 91%, 92%, 93%, 94%, 95%, 96%, 97%, 98%, 99% or greater than 99% similar to SEQ ID NO: 28.

B. Lip1 Proteins

In yet another embodiment, the disclosure relates to one or more non-transgenic mutations in the Lip1 genes (as discussed above in the section entitled Lip1 Mutations) that result in an Lip1 protein with one or more mutations as compared to wild type Lip1 protein. In one embodiment, the non-transgenic mutations include but are not limited to the mutations recited in Tables 1-3 for wheat and Table 4 for rice, corresponding mutations in homoeologues, and combinations thereof.

In another embodiment, the disclosure relates to one or more non-transgenic mutations in the Lip1 gene or promoter that inhibits production of the Lip1 protein. In some embodiments, a mutation in the Lip1 gene or promoter reduces expression of the Lip1 protein. In other embodiments, a mutation in the Lip1 gene or promoter creates an unstable or reduced function Lip1 protein. In another embodiment, the non-transgenic mutations include but are not limited to the mutations recited in Tables 1-3 for wheat and Table 4 for rice, corresponding mutations in homoeologues, and combinations thereof.

1. Expression Level of Lip1 Proteins

In another embodiment, the expression level of Lip1 proteins with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lip1 protein.

In yet another embodiment, the expression level of Lip-A1 protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lip-A1 protein.

In still another embodiment, the expression level of Lip-D1 protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lip-D1 protein.

In still another embodiment, the expression level of Lip-B1 protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type Lip-B1 protein.

In still another embodiment, the expression level of OsLip1 protein with one or more mutations disclosed herein is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type OsLip1 protein.

2. Activity of Lip1 Proteins

In yet another embodiment, the lipase activity of the Lip1 protein with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lip1 protein. In another embodiment, the Lip1 protein with one or more mutations disclosed herein has no activity or zero activity as compared to wild type Lip1 protein.

In yet another embodiment, the lipase activity of the Lip1 protein with one or more mutations disclosed herein is from 0-10% or from 10-30% or from 30-50% or from 50-70% or from 70-80% or from 80-90% or from 90-95% of the activity level of the wild type Lip1 protein.

In yet another embodiment, the lipase activity of the Lip1 protein from the Lip-A1 gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lip-A1 protein. In another embodiment, the Lip-A1 protein with one or more mutations disclosed herein has no activity or zero activity as compared to wild type Lip-A1 protein.

In yet another embodiment, the lipase activity of the Lip1 protein from the Lip-A1 gene with one or more mutations disclosed herein is from 0-10% or from 10-30% or from 30-50% or from 50-70% or from 70-80% or from 80-90% or from 90-95% of the activity level of the wild type Lip-A1 protein.

In yet another embodiment, the lipase activity of the Lip1 protein from the Lip-D1 gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lip-D1 protein. In another embodiment, the Lip-D1 protein with one or more mutations disclosed herein has no activity or zero activity as compared to wild type Lip-D1 protein.

In yet another embodiment, the lipase activity of the Lip1 protein from the Lip-D1 gene with one or more mutations disclosed herein is from 0-10% or from 10-30% or from 30-50% or from 50-70% or from 70-80% or from 80-90% or from 90-95% of the activity level of the wild type Lip-D1 protein.

In yet another embodiment, the lipase activity of the Lip1 protein from the Lip-B1 gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type Lip-B1 protein. In another embodiment, the Lip-B1 protein with one or more mutations disclosed herein has no activity or zero activity as compared to wild type Lip-B1 protein.

In yet another embodiment, the lipase activity of the Lip1 protein from the Lip-B1 gene with one or more mutations disclosed herein is from 0-10% or from 10-30% or from 30-50% or from 50-70% or from 70-80% or from 80-90% or from 90-95% of the activity level of the wild type Lip-B1 protein.

In yet another embodiment, the lipase activity of the Lip1 protein from the OsLip1 gene with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% of the activity level of the wild type OsLip1 protein. In another embodiment, the OsLip1 protein with one or more mutations disclosed herein has no activity or zero activity as compared to wild type OsLip1 protein.

In yet another embodiment, the lipase activity of the Lip1 protein from the OsLip1 gene with one or more mutations disclosed herein is from 0-10% or from 10-30% or from 30-50% or from 50-70% or from 70-80% or from 80-90% or from 90-95% of the activity level of the wild type OsLip1 protein.

II. Hydrolytic Stability; Oxidative Stability; Increased Shelf Life

In yet another embodiment, the disclosure relates to one or more non-transgenic mutations in a Lip1 gene of plant (as discussed above in the section entitled Lip1 Mutations) that results in increased shelf life of a plant product. In yet another embodiment, the disclosure relates to one or more non-transgenic mutations in a Lip1 gene in a plant (as discussed above in the section entitled Lip1 Mutations) that results in increased stability of products made from the grains or seeds of said plant with one or more Lip1 mutations as compared to products made from wild type grains or seeds. In one embodiment, the non-transgenic mutations include but are not limited to the mutations recited in Tables 1-4, corresponding mutations in homoeologues, and combinations thereof.

In yet another embodiment, the shelf life of whole grain flour made from wheat grains with one or more Lip1 mutations disclosed herein is increased from the typical shelf life of whole grain flour. Millers commonly stamp 'use by' dates of 3-9 months after milling for whole grain flour in the United States, but this shelf life can be reduced to 1-3 months by high storage temperatures and humidity. Shelf life can be determined by sensory characteristics of the flour and products made from it including color, flavor, texture, aroma, performance or overall preference of the finished product. Trained panelists can be used to assess differences between materials.

In yet another embodiment, shelf life of whole grain flour made from wheat grain with one or more mutations disclosed herein is increased by 1-9 months, or 2-10 months, or 3-11 months, or 4-12 months, or 5-13 months, or 6-14 months, or 7-15 months, or 8-16 months, or 9-17 months, or 10-18 months or 11-19 months, or 12-20 months, or 13-21 months, or 14-22 months, or 15-23 or 16-24 months as compared to the shelf life of whole grain flour made from wild-type grain.

In yet another embodiment, shelf life of whole grain flour made from wheat grain with one or more mutations disclosed herein is increased by 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, or greater than 30 months as compared to the shelf life of whole grain flour made from wild-type grain.

In yet another embodiment, the hydrolytic stability and/or oxidative stability of whole grain flour made from wheat grain with one or more mutations disclosed herein or rice bran made from rice grain with one or more mutations disclosed herein is increased due to decreased production of the decomposition products of fatty acids that can affect the smell or flavor of the product. Not to be bound by any particular theory, the stability of whole grain flour made from wheat grain with one or more mutations disclosed herein or rice bran made from rice grain with one or more mutations disclosed herein is increased due to the decreased production of the decomposition products of fatty acids.

In yet another embodiment, whole grain flour made from wheat grain with one or more mutations disclosed herein or rice bran made from rice grain with one or more mutations disclosed herein display decreased production of decomposition products of fatty acids, including but not limited to hexanal, or nonenal, or trihydroxydecanoic acid.

In still another embodiment, whole grain flour made from wheat grain with one or more mutations disclosed herein or rice bran made from rice grain with one or more mutations disclosed herein display a decrease in production of decomposition products of fatty acids, wherein said decrease is by 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 69, 69, 70, 71, 72, 73, 74, 75, 76, 77, 78, 79, 80, 81, 82, 83, 84, 85, 86, 87, 88, 89, 90, 91, 92, 93, 94, 95, 86, 97, 98, 99% and by more than 99% as compared to the production of degradation products of fatty acids in whole grain flour made from the wild-type grain or rice bran made from wild type rice grain.

In another embodiment, whole grain flour made from wheat grain with one or more mutations disclosed herein or rice bran made from rice grain with one or more mutations disclosed herein display a decreased production of decomposition products of fatty acids, including but not limited to hexanal, or nonenal, or trihydroxydecanoic acid, wherein the decreased production is from 1% to 5%, or from 5% to 10%, or from 10% to 15%, or from 15% to 20%, or from 20% to 25%, or from 25% to 30%, or from 30% to 35%, or from 35% to 40%, or from 40% to 45%, or from 45% to 50%, or from 50% to 55%, or from 55% to 60%, or from 65% to 70%, or from 70% to 75%, or from 75% to 80%, or from 80% to 85%, or from 85% to 90%, or from 90% to 95%, or from 95% to 99%, or by more than 99% as compared to the production of degradation products of fatty acids in whole grain flour made from the wild-type grain or rice bran made from wild type rice grain.

In another embodiment, whole grain flour made from wheat grain with one or more mutations disclosed herein or rice bran made from rice grain with one or more mutations disclosed herein display a decrease in decomposition products of fatty acids, including but not limited to hexanal, or nonenal, or trihydroxydecanoic acid, wherein said decrease is by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% as compared to the production of degradation products of fatty acids in whole grain flour made from the wild-type grain or rice bran made from wild type rice grain.

III. Transgenes

In one embodiment, the disclosure relates to a transgenic plant that comprises a transgene that encodes a polynucleotide, which down-regulates the expression of the Lip1 gene and/or the activity of the Lip1 protein. Examples of such polynucleotides include, but are not limited to, antisense polynucleotide, a sense polynucleotide, a catalytic polynucleotide, an artificial microRNA or a duplex RNA molecule.

In one embodiment, the disclosure relates to a wheat plant comprising a transgene that reduces the expression of the Lip1 gene and/or activity of the Lip1 protein, wherein the wheat plant has grains with improved shelf life as compared to grains from a wild type plant. In another embodiment, the disclosure relates to a rice plant comprising a transgene that reduces the expression of the Lip1 gene and/or activity of the Lip1 protein, wherein the rice plant has grains with improved shelf life as compared to grains from a wild type plant.

A. Antisense Polynucleotides

The term "antisense polynucleotide" shall be taken to refer to a DNA or RNA, or combination thereof, molecule that is complementary to at least a portion of a specific mRNA molecule encoding Lip1 and capable of interfering with a post-transcriptional event such as mRNA translation. An antisense polynucleotide in a plant will hybridize to a target polynucleotide under physiological conditions. As used herein, the term "an antisense polynucleotide which hybridizes under physiological conditions" means that the polynucleotide (which is fully or partially single stranded) is at least capable of forming a double stranded polynucleotide with mRNA encoding a protein.

Antisense molecules may include sequences that correspond to the structural gene or for sequences that effect control over the gene expression or splicing event. For example, the antisense sequence may correspond to the targeted coding region of Lip1 or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences, which may function to stabilize the molecule.

B. Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain").

The ribozymes in plants disclosed herein and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, the catalytic polynucleotides should also be capable of hybridizing a target nucleic acid molecule (for example mRNA encoding Lip1) under "physiological conditions," namely those conditions within a plant cell.

C. RNA Interference

RNA interference (RNAi) is particularly useful for specifically inhibiting the production of a particular protein. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering, WO 99/32619, WO 99/53050, WO 99/49029, and WO 01/34815.

In one example, a DNA is introduced that directs the synthesis of an at least partly double stranded (duplex) RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridize should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

In one embodiment, small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the barley plant in which it is to be introduced, e.g., as determined by standard BLAST search.

Another RNAi approach that may be used is multi-valent RNAi, as described in U.S. Pat. No. 9,200,276, which targets multiple sequences simultaneously that can be delivered through a spray application as opposed to developing a transgenic plant.

D. microRNA

MicroRNA regulation is a clearly specialized branch of the RNA silencing pathway that evolved towards gene regulation, diverging from conventional RNAi/Post transcriptional Gene Silencing (PTGS). MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression.

E. Co-Suppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

IV. Genomic Editing

In one embodiment, the disclosure relates to a plant with reduced expression of the Lip1 gene and/or reduced activity of the Lip1 protein, wherein reduced expression of the Lip1 gene and/or reduced activity of the Lip1 protein is achieved by genomic editing.

In one embodiment, the disclosure relates to a wheat plant with a genomically edited Lip1 gene, wherein the wheat plant has improved shelf life grains as compared to a wild type plant.

Genome editing, or genome editing with engineered nucleases (GEEN), is a type of genetic engineering in which DNA is inserted, replaced, or removed from a genome using artificially engineered nucleases, or "molecular scissors." The nucleases create specific double-stranded breaks (DSBs) at desired locations in the genome, and harness the cell's endogenous mechanisms to repair the induced break by natural processes of homologous recombination (HR) and nonhomologous end-joining (NHEJ). There are currently four main families of engineered nucleases being used: Zinc finger nucleases (ZFNs), Transcription Activator-Like Effector Nucleases (TALENs), the CRISPR/Cas system, and engineered meganuclease with a re-engineered homing endonucleases.

A. Zinc Finger Nucleases (ZFNs)

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms.

ZFNs consist of an engineered zinc finger DNA-binding domain fused to the cleavage domain of the FokI restriction endonuclease. ZFNs can be used to induce double-stranded breaks (DSBs) in specific DNA sequences and thereby promote site-specific homologous recombination with an exogenous template. The exogenous template contains the sequence that is to be introduced into the genome.

Publicly available methods for engineering zinc finger domains include: (1) Context-dependent Assembly (CoDA), (2) Oligomerized Pool Engineering (OPEN), and (3) Modular Assembly.

In one embodiment, the disclosure relates to reducing expression of the Lip1 gene and/or reducing activity of the Lip1 protein using ZFNs.

B. Transcription Activator-Like Effector Nucleases (TALENs)

TALEN is a sequence-specific endonuclease that consists of a transcription activator-like effector (TALE) and a FokI endonuclease. TALE is a DNA-binding protein that has a highly conserved central region with tandem repeat units of 34 amino acids. The base preference for each repeat unit is determined by two amino acid residues called the repeat-variable di-residue (RVD), which recognizes one specific nucleotide in the target DNA, Arrays of DNA-binding repeat units can be customized for targeting specific DNA sequences. As with ZFNs, dimerization of two TALENs on targeted specific sequences in a genome results in FokI-dependent introduction of DSBs, stimulating homology directed repair (HDR) and Non-homologous end joining (NHEJ) repair mechanisms.

In one embodiment, the disclosure relates to reducing expression of the Lip1 gene and/or reducing activity of the Lip1 protein using TALENs.

C. CRISPR/Cas System

The Clustered Regularly Interspaced Short Palindromic Repeats (CRISPR) Type II system is an RNA-Guided Endonuclease technology for genome engineering. There are two distinct components to this system: (1) a guide RNA and (2) an endonuclease, in this case the CRISPR associated (Cas) nuclease, Cas9.

The guide RNA is a combination of the endogenous bacterial crRNA and tracrRNA into a single chimeric guide RNA (gRNA) transcript. The gRNA combines the targeting specificity of the crRNA with the scaffolding properties of the tracrRNA into a single transcript. When the gRNA and the Cas9 are expressed in the cell, the genomic target sequence can be modified or permanently disrupted.

The gRNA/Cas9 complex is recruited to the target sequence by the base-pairing between the gRNA sequence and the complementarity to the target sequence in the genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the wild-type Cas9 can cut both strands of DNA causing a Double Strand Break (DSB). Cas9 will cut 3-4 nucleotides upstream of the PAM sequence. A DSB can be repaired through one of two general repair pathways: (1) NHEJ DNA repair pathway or (2) the HDR pathway. The NHEJ repair pathway often results in insertions/deletions (InDels) at the DSB site that can lead to frameshifts and/or premature stop codons, effectively disrupting the open reading frame (ORF) of the targeted gene.

The HDR pathway requires the presence of a repair template, which is used to fix the DSB. HDR faithfully copies the sequence of the repair template to the cut target sequence. Specific nucleotide changes can be introduced into a targeted gene by the use of HDR with a repair template.

In one embodiment, the disclosure relates to reducing expression of the Lip1 gene and/or reducing activity of the Lip1 protein using the CRISPR/cas9 system or similar technology (or a variant of the technology).

D. Meganuclease with Re-Engineered Homing Nuclease

Meganucleases are endodeoxyribonucleases characterized by a large recognition site (double-stranded DNA sequences of 12 to 40 base pairs); as a result this site generally occurs only once in any given genome. For example, the 18-base pair sequence recognized by the I-SceI meganuclease would on average require a genome twenty times the size of the human genome to be found once by chance (although sequences with a single mismatch occur about three times per human-sized genome). Meganucleases are therefore considered to be the most specific naturally occurring restriction enzymes.

Among meganucleases, the LAGLIDADG family of homing endonucleases has become a valuable tool for the study of genomes and genome engineering over the past fifteen years. By modifying their recognition sequence through protein engineering, the targeted sequence can be changed.

In one embodiment, the disclosure relates to reducing expression of the Lip1 gene and/or reducing activity of the Lip1 protein using a meganuclease with a re-engineered homing nuclease.

V. Wheat Cultivars

In one embodiment, a wheat cultivar having at least one Lip gene that is diploid, tetraploid, or hexaploid may be used. In another embodiment, the wheat is *Triticum aestivum*. In another embodiment, the wheat is *Triticum turgidum* ssp durum.

In one embodiment, any cultivar of wheat can be used to create mutations in an Lip1 gene. In one embodiment, any cultivar of wheat can be used to create mutations in an Lip-A1 gene. In another embodiment, any cultivar of wheat can be used to create mutations in an Lip-B1 gene. In another embodiment, any cultivar of wheat can be used to create mutations in an Lip-D1 gene.

In one embodiment, any cultivar of wheat can be used as lines to cross Lip1 mutations into different cultivars.

In another embodiment, any cultivar of wheat having at least one Lip1 gene may be used including but not limited to hard red spring wheat, hard white winter wheat, durum wheat, soft white spring wheat, soft white winter wheat, hard red winter wheat, common wheat, splelt wheat, emmer wheat, pasta wheat and turgidum wheat.

In one embodiment, hard red spring wheat includes but is not limited to Bullseye, Cabernet, Cal Rojo, Hank, Joaquin, Kelse, Lariat, Lassik, Malbec, Mika, PR 1404, Redwing, Summit 515, SY 314, Triple IV, Ultra, WB-Patron, WB-Rockland, Yecora Rojo, Accord, Aim, Anza, Baker, Beth Hashita, Bonus, Borah, Brim, Brooks, Buck Pronto, Butte 86, Cavalier, Challenger, Chief, Ciano T79, Colusa, Companion, Copper, Cuyama, Dash 12, Eldon, Enano, Express, Expresso, Jefferson, Genero F81, Grandin, Helena 554, Hollis, Imuris T79, Inia 66R, Jerome, Kern, Len, Marshall, McKay, Nomad, Northwest 10, Oslo, Pavon F76, Pegasus, Pitic 62, Poco Red, Powell, Probrand 711, Probrand 751, Probrand 771, Probrand 775, Probred, Prointa Queguay, Prointa Quintal, Rich, RSI 5, Sagittario, Scarlet, Serra, Shasta, Solano, Spillman, Sprite, Stander, Stellar, Stoa, Success, Summit, Sunstar 2, Sunstar King, Tadinia, Tammy, Tanori 71, Tara 2000, Tempo, Tesia T79, Topic, UI Winchester, Vance, Vandal, W444, Wampum, Wared, WB-Fuzion, Westbred 906R, Westbred 911, Westbred 926, Westbred 936, Westbred Discovery, Westbred Rambo, Yolo, and Zeke.

In another embodiment, hard white wheat includes but is not limited to Blanca Fuerte, Blanca Grande 515, Blanca Royale, Clear White, Patwin, Patwin 515, WB-Cristallo, WB-Paloma, WB-Perla, Alta Blanca, Blanca Grande, Delano, Golden Spike, ID377S, Klasic, Lochsa, Lolo, Macon, Otis, Phoenix, Pima 77, Plata, Pristine, Ramona 50, Siete Cerros 66, Vaiolet, and Winsome.

In yet another embodiment, durum wheat includes but is not limited to Crown, Desert King, Desert King HP, Duraking, Fortissimo, Havasu, Kronos, Maestrale, Normanno, Orita, Platinum, Q-Max, RSI 59, Saragolla, Tango, Tipai, Topper, Utopia, Volante, WB-Mead, Westmore, Aldente, Aldura, Altar 84, Aruba, Bittern, Bravadur, Candura, Cortez, Deluxe, Desert Titan, Durex, Durfort, Eddie, Germains 5003D, Imperial, Kofa, Levante, Matt, Mead, Mexicali 75, Minos, Modoc, Mohawk, Nudura, Ocotillo, Produra, Reva, Ria, Septre, Sky, Tacna, Titan, Trump, Ward, Westbred 803, Westbred 881, Westbred 883, Westbred 1000D, Westbred Laker, Westbred Turbo, and Yavaros 79.

In another embodiment, soft white spring wheat includes but is not limited to Alpowa, Alturas, Babe, Diva, JD, New Dirkwin, Nick, Twin, Whit, Blanca, Bliss, Calorwa, Centennial, Challis, Dirkwin, Eden, Edwall, Fielder, Fieldwin, Jubilee, Louise, Owens, Penawawa, Pomerelle, Sterling, Sunstar Promise, Super Dirkwin, Treasure, UI Cataldo, UI Pettit, Urquie, Vanna, Waduel, Waduel 94, Wakanz, Walladay, Wawawai, Whitebird, and Zak.

In still another embodiment, soft white winter wheat includes but is not limited to AP Badger, AP Legacy, Brundage 96, Bruneau, Cara, Goetze, Legion, Mary, Skiles, Stephens, SY Ovation, Tubbs, WB-Junction, WB-528, Xerpha, Yamhill, Barbee, Basin, Bitterroot, Bruehl, Castan, Chukar, Coda, Daws, Edwin, Eltan, Faro, Finch, Foote, Gene, Hill 81, Hiller, Hubbard, Hyak, Hyslop, Idaho 587, Kmor, Lambert, Lewjain, MacVicar, Madsen, Malcolm, Masami, McDermid, Moro, Nugaines, ORCF-101, ORCF-102, ORCF-103, Rod, Rohde, Rulo, Simon, Salute, Temple, Tres, Tubbs 06, UICF-Brundage, WB-523, and Weatherford.

In another embodiment, hard red winter wheat includes but is not limited to Andrews, Archer, Batum, Blizzard, Bonneville, Boundary, Declo, Deloris, Finley, Garland, Hatton, Hoff, Longhorn, Manning, Meridian, Promontory, Vona, Wanser, Winridge.

In another embodiment, common wheat (hexaploid, free threshing), *Triticum aestivum* ssp *aestivum* includes but is not limited to Sonora, Wit Wolkoring, Chiddam Blanc De Mars, India-Jammu, Foisy.

In still another embodiment, spelt wheat (hexaploid, not free threshing), *Triticum aestivum* ssp *spelta* includes but is not limited to Spanish Spelt, Swiss Spelt.

In yet another embodiment, Emmer Wheat (tetraploid), *Triticum turgidum* ssp. *dicoccum* includes but is not limited to Ethiopian Blue Tinge.

In another embodiment, pasta wheat (tetraploid, free threshing), *Triticum turgidum* ssp durum includes but is not limited to Kronos.

In yet another embodiment, *Turgidum* Wheat (tetraploid, free threshing), *Triticum turgidum* ssp *turgidum* includes but is not limited to Akmolinka, Maparcha.

In one embodiment, a cultivar of wheat having at least one Lip1 gene with substantial percent identity to SEQ ID NO: 1, SEQ ID NO: 2, SEQ ID NO: 4, SEQ ID NO: 5, SEQ ID NO: 7, and SEQ ID NO: 8 may be used with the methods and compositions disclosed herein.

As used herein with regard to the wheat cultivars, "substantial percent identity" means that the DNA sequence of the gene is sufficiently similar to SEQ ID NO: 1, 2, 4, 5, 7, and 8 at the nucleotide level to code for a substantially similar protein, allowing for allelic differences (or alternate mRNA splicing) between cultivars. In accordance with one embodiment of the invention, "substantial percent identity" may be present when the percent identity in the coding region between the Lip1 gene and SEQ ID NO: 1, 2, 4, 5, 7, and 8 is as low as about 85%, provided that the percent identity in the conserved regions of the gene is higher (e.g., at least about 90%). Preferably the percent identity in the coding region is 85-90%, more preferably 90-95%, and optimally, it is above 95%. Thus, one of skill in the art may prefer to utilize a wheat cultivar having commercial popularity or one having specific desired characteristics in which to create the Lip 1-mutated wheat plants, without deviating from the scope and intent of the present invention. Alternatively, one of skill in the art may prefer to utilize a wheat cultivar having few polymorphisms, such as an in-bred cultivar, in order to facilitate screening for mutations within one or more Lip1 genes in accordance with the present invention.

VI. Representative Methodology for Identification of Lip1 Mutations in a Plant

In order to create and identify the Lip1 mutations and plants disclosed herein, a method known as TILLING (Targeting Induced Local Lesions IN Genomes) was utilized. See McCallum et al., *Nature Biotechnology* 18:455-457, 2000; McCallum et al., *Plant Physiology,* 123:439-442, 2000; U.S. Publication No. 20040053236; and U.S. Pat. No. 5,994,075, all of which are incorporated herein by reference. In the basic TILLING methodology, plant materials, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

The hexaploid cultivar Express and tetraploid cultivar Kronos were used. The diploid rice cultivars TR64 and Cypress were used.

In one embodiment, seeds from a plant are mutagenized and then grown into M1 plants. The M1 plants are then allowed to self-pollinate and seeds from the M1 plant are grown into M2 plants, which are then screened for mutations in their Lip1 loci. While M1 plants can be screened for mutations in accordance with alternative embodiments of the invention, one advantage of screening the M2 plants is that all somatic mutations correspond to germline mutations.

One of skill in the art will understand that a variety of plant materials, including, but not limited to, seeds, pollen, plant tissue or plant cells, may be mutagenized in order to create the Lip1-mutated plants disclosed herein. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for Lip1 mutations instead of waiting until the M2 generation.

Mutagens that create primarily point mutations and deletions, insertions, transversions, and or transitions, such as chemical mutagens or radiation, may be used to create the mutations. Mutagens conforming with the method of the invention include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7, 12 dimethyl-benz(a) anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloro-ethyl)aminopropylamino] acridine dihydrochloride (ICR-170), formaldehyde, fast neutrons, and gamma irradiation. Spontaneous mutations in a Lip1 gene that may not have been directly caused by the mutagen can also be identified.

Other methods such as genome editing can also be used to alter the sequence of a target gene including its promoter to up or down regulate expression or activity. These methods are known to those skilled in the art, and include CRISPR, Talens, Zinc finger nucleases and miRNA among other methods. For example, see a review of these methods by Xiong et al. *Horticulture Research* 2: 15019, 2015.

Any suitable method of plant DNA preparation now known or hereafter devised may be used to prepare the wheat plant DNA for Lip1 mutation screening. For example, see Chen & Ronald, *Plant Molecular Biology Reporter* 17:53-57, 1999; Stewart and Via, *Bio Techniques* 14:748-749, 1993. Additionally, several commercial kits designed for this purpose are available, including kits from Qiagen (Valencia, CA) and Qbiogene (Carlsbad, CA).

In one embodiment, prepared DNA from individual wheat plants are pooled in order to expedite screening for mutations in one or more Lip1 genes of the entire population of plants originating from the mutagenized plant tissue. The size of the pooled group may be dependent upon the sensitivity of the screening method used. Preferably, groups of two or more individual wheat plants are pooled.

In another embodiment, after the DNA samples are pooled, the pools are subjected to Lip1 sequence-specific amplification techniques, such as Polymerase Chain Reaction (PCR). For a general overview of PCR, see *PCR Protocols: A Guide to Methods and Applications* (Innis, Gelfand, Sninsky, and White, eds.), Academic Press, San Diego, 1990.

Any primer specific to an Lip1 locus or the sequences immediately adjacent to one of these loci may be utilized to amplify the Lip1 sequences within the pooled DNA sample. Preferably, the primer is designed to amplify the regions of the Lip1 locus where useful mutations are most likely to arise. Most preferably, the primer is designed to detect exonic regions of one or more Lip1 genes. Additionally, it is preferable for the primer to target known polymorphic sites to design genome specific primers in order to ease screening for point mutations in a particular genome.

In one embodiment, wheat tilling primers are designed based upon the Lip1 genes of wheat: Lip-A1, Lip-D1 and Lip-B1 (SEQ ID NOs: 1, 2, 4, 5, 7 and 8). Table 5 shows exemplary primers that have proven useful in identifying mutations in Lip-A1 of wheat (SEQ ID NOs: 10-11), Lip-D1 (SEQ ID NOs: 12-13), Lip-B1 (SEQ ID NOs: 14-15). Also in Table 5 are exemplary primers (SEQ ID NOs: 16-17) that have proven useful as markers to identifying intact versus missing Lip-B1 genomic sequences, and exemplary primers (SEQ ID NOs: 18-25) that have proven useful to evaluate gene expression of multiple wheat lipase genes. These primers are also detailed in the Sequence Listing appended hereto.

In another embodiment, primers are designed based upon the OsLip1 DNA sequences (SEQ ID NOs: 26-27). Table 5 also shows exemplary primers that have proven useful in identifying mutations in OsLip1 (SEQ ID NOs: 29-30).

TABLE 5

Exemplary Primers

| SEQ ID NO: 10 | Ta_Lip1_A_L2 | GAAATTGATCTTCTGCAC TTGTGTTCAGGA |
|---|---|---|
| SEQ ID NO: 11 | Ta_Lip1_A_R1 | TGGGGATAATGTTAGAAC TAGGAGCTA |
| SEQ ID NO: 12 | Ta_Lip1_DB_L1 | GACAGGCAAAATCAATT GGGGTCATTT |

TABLE 5-continued

Exemplary Primers

| SEQ ID NO: 13 | Ta_Lip1_D_R3 | TGATCAGTGGGGAAATGT TAGAATTAGGAGA |
|---|---|---|
| SEQ ID NO: 14 | Ta_Lip1_B_L1 | CTGAAATTGATCTTCTGC ACTTGTGTTATTGCA |
| SEQ ID NO: 15 | Ta_Lip1_B_R1 | AGCATAACACAGCGATAA AGGCTTCCTAGG |
| SEQ ID NO: 16 | Ta_Lip1_B_Lmarker | TCTCTGTCAAGAATCACG GTC |
| SEQ ID NO: 17 | Ta_Lip1_B_Rmarker | GCTGCTGCATATGACACC TA |
| SEQ ID NO: 18 | Ta_Lip1_L1 | CACAGTGGATTTTTCTCC TCCT |
| SEQ ID NO: 19 | Ta_Lip1_R1 | CCGATATCCCCATATGTC TTTC |
| SEQ ID NO: 20 | Ta_Lip2_L1 | GACCCAGTTTCAACAGCA AC |
| SEQ ID NO: 21 | Ta_Lip2_R1 | CGGACCTAACAGCTCTAT ATA |
| SEQ ID NO: 22 | Ta_Lip3_L3 | CACTTGATCTTGTTGTGA ACTAC |
| SEQ ID NO: 23 | Ta_Lip3_R3 | GCGTGAGGCAAGTATCTC TT |
| SEQ ID NO: 24 | Ta_GAPD_F | TGTCCATGCCATGACTGC AA |
| SEQ ID NO: 25 | Ta_GAPD_R | CCAGTGCTGCTTGGAATG ATG |
| SEQ ID NO: 29 | OsLip1_L2 | CACCTACTCCGATTGGGC TTAATTTCACA |
| SEQ ID NO: 30 | OsLip1_R8 | GAACAAGACTGTATCAGT TTACATAACAACCAATG |

In another embodiment, the PCR amplification products may be screened for Lip1 mutations using any method that identifies nucleotide differences between wild type and mutant sequences. These may include, for example, without limitation, sequencing, denaturing high pressure liquid chromatography (dHPLC), constant denaturant capillary electrophoresis (CDCE), temperature gradient capillary electrophoresis (TGCE) (see Li et al., *Electrophoresis* 23(10):1499-1511, 2002), or by fragmentation using enzymatic cleavage, such as used in the high throughput method described by Colbert et al., *Plant Physiology* 126:480-484, 2001. Preferably, the PCR amplification products are incubated with an endonuclease that preferentially cleaves mismatches in heteroduplexes between wild type and mutant sequences.

In another embodiment, cleavage products are electrophoresed using an automated sequencing gel apparatus, and gel images are analyzed with the aid of a standard commercial image-processing program.

In another embodiment, DNA or RNA from plants with induced or naturally occurring mutations or deletions can be screened with or without PCR by next generation sequencing methods such as exome capture or TILLING by sequencing (King, Robert, et al. Mutation Scanning in Wheat by Exon Capture and Next-Generation Sequencing. *PloS one* 10.9 (2015): e0137549; Tsai, Helen, et al. Discovery of rare mutations in populations: TILLING by sequencing. *Plant physiology* 156.3 (2011): 1257-1268; Liu, Sanzhen, et al. "Gene mapping via bulked segregant RNA-Seq (BSR-Seq)." *PLoS One* 7.5 (2012): e36406).

In yet another embodiment, once an M2 plant having a mutated Lip1 gene sequence is identified, the mutations are analyzed to determine their effect on the expression, translation, and/or activity of an Lip1 enzyme. In one embodiment, the PCR fragment containing the mutation is sequenced, using standard sequencing techniques, in order to determine the exact location of the mutation in relation to the overall Lip1 sequence. Each mutation is evaluated in order to predict its impact on protein function (i.e., from completely tolerated to causing loss-of-function) using bioinformatics tools such as SIFT (Sorting Intolerant from Tolerant; Ng and Henikoff, *Nucleic Acids Research* 31:3812-3814, 2003), PSSM (Position-Specific Scoring Matrix; Henikoff and Henikoff, *Computer Applications in the Biosciences* 12:135-143, 1996) and PARSESNP (Taylor and Greene, *Nucleic Acids Research* 31:3808-3811, 2003). For example, a SIFT score that is less than 0.05 and a large change in PSSM score (e.g., roughly 10 or above) indicate a mutation that is likely to have a deleterious effect on protein function. These programs are known to be predictive, and it is understood by those skilled in the art that the predicted outcomes are not always accurate.

In another embodiment, if the initial assessment of a mutation in the M2 plant indicates it to be of a useful nature and in a useful position within an Lip1 gene, including its promoter, then further phenotypic analysis of the wheat plant containing that mutation may be pursued. In hexaploid wheat, mutations in each of the A, B and D genomes usually must be combined before a phenotype can be detected. In tetraploid wheat, A and B genome mutations are combined. In addition, the mutation containing plant can be backcrossed or outcrossed two times or more in order to eliminate background mutations at any generation. Then the backcrossed or outcrossed plant can be self-pollinated or crossed in order to create plants that are homozygous for the Lip1 mutations.

Several physical characteristics of these homozygous Lip1 mutant plants are assessed to determine if the mutation results in a useful phenotypic change in the wheat plant without resulting in undesirable negative effects, such as significantly reduced seed yields or issues with germination.

VII. Methods of Producing a Plant

In another embodiment, the disclosure relates to a method for producing a plant having plant products or plant parts with increased hydrolytic and/or oxidative stability. In another embodiment, the disclosure relates to a method for producing a plant having plant products or plant parts with an increased shelf-life.

In one embodiment, the method comprises inducing at least one non-transgenic mutation in at least one copy of an Lip1 gene in plant material or plant parts from a parent plant; growing or using the mutagenized plant material to produce progeny plants; analyzing mutagenized plant material and/or progeny plants to detect at least one mutation in at least one copy of a Lip1 gene; and selecting progeny plants that have at least one mutation in at least one copy of an Lip1 gene.

In another embodiment, the method further comprises crossing progeny plants that have at least one mutation in at least one copy of an Lip1 gene with other progeny plants that have at least one mutation in a different copy of an Lip1 gene. The process of identifying progeny plants with mutations and crossing said progeny plants with other progeny plants, which have mutations, can be repeated to produce progeny plants with reduced Lip1 enzyme activity.

In another embodiment, the disclosure relates to a method of producing a wheat plant comprising out-crossing Lip1 gene mutations in a wheat plant to a wild type wheat.

In another embodiment, the disclosure relates to a method for producing a wheat plant producing grains and flour with increased hydrolytic and oxidative stability and products from grain of said wheat plant having increased shelf life. In still another embodiment, the invention relates to a method for producing a wheat plant having reduced activity of one or more Lip1 enzymes compared to the wild type wheat plants.

In yet another embodiment, the disclosure relates to a method for producing a rice plant producing seeds with increased hydrolytic and oxidative stability and products from seeds of said rice plant having increased shelf life. In still another embodiment, the disclosure relates to a method for producing a rice plant having seeds with reduced activity of one or more Lip1 enzymes compared to the wild type rice plants.

In another embodiment, the activity of the Lip1 protein in a plant is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, or 95-99% of the activity of the Lip1 protein in the wild type plant.

In another embodiment, the activity of the Lip1 protein in grain from a plant is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, or 95-99% of the activity of the Lip1 protein in the wild type grain.

In another embodiment, the activity of the Lip1 protein in seed from a plant is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, or 95-99% of the activity of the Lip1 protein in the wild type seed.

A. Methods of Producing a Wheat Plant with One or More Mutations in the Lip1 Gene in More than One Genome In still another embodiment, the disclosure relates to a method for producing a wheat plant comprising inducing at least one non-transgenic mutation in at least one copy of a Lip1 gene in plant material from a parent wheat plant that comprises a mutation in a Lip1 gene; growing or using the mutagenized plant material to produce progeny wheat plants; and selecting progeny wheat plants that have at least one mutation in at least one copy of an a Lip1 gene.

In still another embodiment, the disclosure relates to a method for producing a wheat plant comprising inducing at least one non-transgenic mutation in at least one copy of a Lip1 gene in plant material from a parent wheat plant that comprises a mutation in a Lip1 gene; growing or using the mutagenized plant material to produce progeny wheat plants; crossing to plants containing at least one non-transgenic mutation in at least one copy of a Lip 1 gene, and selecting progeny wheat plants that have at least one mutation in at least two copies of an a Lip1 gene.

In yet another embodiment, the disclosure relates to a method for producing a wheat plant comprising inducing at least one non-transgenic mutation in at least one copy of an Lip1 gene in plant material from a parent wheat plant that comprises at least one mutation in two Lip1 genes; growing or using the mutagenized plant material to produce progeny wheat plants; crossing to plants containing at least one non-transgenic mutation in at least one copy of a Lip 1 gene, and selecting progeny wheat plants that have at least one mutation in three copies of an Lip1 gene. In this embodiment, there would be at least one mutation in the Lip1 gene of the A, B and D genomes.

For example, the parent wheat plant may have a mutation in a Lip-A1 gene of the A genome and is crossed to a plant with a mutation in a Lip-D1 gene of the D genome and the selected progeny wheat plants may have a mutation in both the Lip-A1 of the A genome and Lip-D1 gene of the D genome. Alternatively, the parent wheat plant may have a mutation in an Lip-A1 gene of the A genome and is crossed to a plant with a mutation in a Lip-B1 gene of the B genome and the selected progeny wheat plants may have a mutation in both the Lip-A1 of the A genome and Lip-B1 gene of the B genome. Alternatively, the parent wheat plant may have a mutation in an Lip-B1 gene of the B genome and is crossed to a plant with a mutation in a Lip-D1 gene of the D genome and the selected progeny wheat plants may have a mutation in both the Lip-B1 of the B genome and Lip-D1 gene of the D genome. Or the parent wheat plant may have a mutation in an Lip-A1 gene of the A genome and is crossed to a plant with a mutation in a Lip-D1 gene of the D and a plant with a mutation in a Lip-B1 gene of the B genome and the selected progeny wheat plants may have a mutation in the Lip-A1 gene of the A genome, the Lip-B1 gene of the B genome and the Lip-D1 gene of the D genome. These examples are provided merely for clarification and should not limit the methods or gene combinations disclosed herein.

In another embodiment, the disclosure relates to a method for producing a wheat plant comprising crossing a first wheat plant that has at least one non-transgenic mutation in a first Lip1 gene with a second wheat plant that has at least one non-transgenic mutation in a second Lip1 gene; and selecting progeny wheat plants that have at least one mutation in at least two copies of an Lip1 gene. In this embodiment, there would be at least one mutation in the Lip1 gene of the A and D genomes or the A and B genomes or the B and D genomes.

In another embodiment, the disclosure relates to a method for producing a wheat plant comprising crossing a first wheat plant that has at least one non-transgenic mutation in a first and second Lip1 gene with a second wheat plant that has at least one non-transgenic mutation in a third Lip1 gene; and selecting progeny wheat plants that have at least one mutation in all three copies of an Lip1 gene. In this embodiment, there would be at least one mutation in the Lip1 gene of the A, B and D genomes.

VIII. Plants, Seed and Parts of Plant

In one embodiment, a plant is produced according to the methods disclosed herein. In another embodiment, the plant, seed or parts of a plant have one or more mutations in an Lip1 gene. In another embodiment, the plant, seed or parts of a plant have one or more mutations in one or more Lip1 genes.

In another embodiment, the disclosure relates to a plant, seed or parts of a plant comprising one or more non-transgenic mutations in one or more Lip1 genes.

In another embodiment, the disclosure relates to a wheat plant, wheat seed or parts of a wheat plant comprising at least one non-transgenic mutation in the Lip1 gene in each of two genomes. In still another embodiment, the disclosure relates to a wheat plant, wheat seed or parts of a wheat plant comprising at least one non-transgenic mutation in the Lip1 gene in each of three genomes.

In one embodiment, the wheat plant, wheat seed or parts of a wheat plant comprises one or more non-transgenic mutations in both alleles of the Lip1 gene in the A genome. In another embodiment, the non-transgenic mutations are identical in both alleles of the Lip1 gene of the A genome.

In one embodiment, the wheat plant, wheat seed or parts of a wheat plant comprises one or more non-transgenic mutations in both alleles of the Lip1 gene in the B genome. In another embodiment, the non-transgenic mutations are identical in both alleles of the Lip1 gene of the B genome.

In one embodiment, the wheat plant, wheat seed or parts of a wheat plant comprises one or more non-transgenic mutations in both alleles of the Lip1 gene in the D genome. In another embodiment, the non-transgenic mutations are identical in both alleles of the Lip1 gene of the D genome.

In another embodiment, the wheat plant, wheat seed or parts of the wheat plant comprise a polynucleotide with one or more non-transgenic mutations listed in Table 1 and is 85%, 86%, 87%, 88%, 89%, 90%, 91%, 92%, 93%, 94%, 95%, 96%, 97%, 98%, 99% or greater than 99% identical or similar to SEQ ID NO: 1.

In still another embodiment, the wheat plant, wheat seed or parts of a wheat plant comprise a polynucleotide with one or more non-transgenic mutations listed in Table 1 that codes for a Lip1 protein, wherein the Lip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 3.

In another embodiment, the wheat plant, wheat seed or parts of the wheat plant comprise a polynucleotide with one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 1.

In still another embodiment, the wheat plant, wheat seed or parts of a wheat plant comprise a polynucleotide with one or more non-transgenic mutations that codes for a Lip1 protein, wherein the Lip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 3.

In another embodiment, the wheat plant, wheat seed or parts of the wheat plant comprise a polynucleotide with one or more non-transgenic mutations listed in Table 2 and is 85%, 86%, 87%, 88%, 89%, 90%, 91%, 92%, 93%, 94%, 95%, 96%, 97%, 98%, 99% or greater than 99% identical or similar to SEQ ID NO: 4.

In still another embodiment, the wheat plant, wheat seed or parts of a wheat plant comprise a polynucleotide with one or more non-transgenic mutations listed in Table 2 that codes for a Lip1 protein, wherein the Lip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In another embodiment, the wheat plant, wheat seed or parts of the wheat plant comprise a polynucleotide with one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 4.

In still another embodiment, the wheat plant, wheat seed or parts of a wheat plant comprise a polynucleotide with one or more non-transgenic mutations that codes for a Lip1 protein, wherein the Lip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In another embodiment, the wheat plant, wheat seed or parts of the wheat plant comprise a polynucleotide with one or more non-transgenic mutations listed in Table 3 and is 85%, 86%, 87%, 88%, 89%, 90%, 91%, 92%, 93%, 94%, 95%, 96%, 97%, 98%, 99% or greater than 99% identical or similar to SEQ ID NO: 7.

In still another embodiment, the wheat plant, wheat seed or parts of a wheat plant comprise a polynucleotide with one or more non-transgenic mutations listed in Table 3 that codes for a Lip1 protein, wherein the Lip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 9.

In another embodiment, the wheat plant, wheat seed or parts of the wheat plant comprise a polynucleotide with one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 7.

In still another embodiment, the wheat plant, wheat seed or parts of a wheat plant comprise a polynucleotide with one or more non-transgenic mutations that codes for a Lip1 protein, wherein the Lip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 9.

In another embodiment, the wheat plant, wheat seed or parts of a wheat plant has one or more mutations in the Lip1 gene including but not limited to one or more mutations enumerated in Tables 1-3 and corresponding mutations in the homoeologues. A wheat plant, wheat seed or parts of a wheat plant can be generated having 1, 2, 3, 4, 5, 6, 7, 8, 9, 10, 11, 12, 13, 14, 15, 16, 17, 18, 19, 20, 21, 22, 23, 24, 25 or greater than 25 of the mutations disclosed herein including but not limited to the mutations disclosed in Tables 1, 2 and 3 as well as mutations in the corresponding homoeologues.

In another embodiment, the wheat seed containing one or more mutations disclosed herein germinates at a rate comparable to wild type wheat seed. In still another embodiment, the wheat seed containing one or more mutations disclosed herein has physical characteristics, including but not limited to size, weight, length, comparable to wild type wheat seed.

In still another embodiment, the wheat plants containing one or more mutations disclosed herein has fertility comparable wild type wheat plants.

In one embodiment, the rice plant, rice seed or parts of a rice plant comprises one or more non-transgenic mutations in both alleles of the OsLip1 gene. In another embodiment, the non-transgenic mutations are identical in both alleles of the OsLip1 gene.

In another embodiment, the rice plant, rice seed or parts of the rice plant comprise a polynucleotide with one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 24.

In still another embodiment, the rice plant, rice seed or parts of the rice plant comprise a polynucleotide with one or more non-transgenic mutations that codes for a OsLip1 protein, wherein the OsLip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 26.

In another embodiment, the wheat plant, wheat seed or parts of a wheat plant has one or more mutations in the Lip1 gene including but not limited to one or more mutations enumerated in Tables 1-3 and corresponding mutations in the homoeologues. A wheat plant, wheat seed or parts of a wheat plant can be generated having 1, 2, 3, 4, 5, 6, 7, 8, 9, 10, 11, 12, 13, 14, 15, 16, 17, 18, 19, 20, 21, 22, 23, 24, 25 or greater than 25 of the mutations disclosed herein including but not limited to the mutations disclosed in Tables 1, 2 and 3, as well as mutations in the corresponding homoeologues.

In another embodiment, the rice seed containing one or more mutations disclosed herein germinates at a rate comparable to wild type rice seed. In still another embodiment, the rice seed containing one or more mutations disclosed herein has physical characteristics, including but not limited to size, weight, length, comparable to wild type rice seed.

In still another embodiment, the rice plants containing one or more mutations disclosed herein has fertility comparable wild type rice plants.

IX. Grain, Flour, Starch and Seeds

In another embodiment, the disclosure relates to a grain, flour, starch or bran comprising one or more non-transgenic mutations in the Lip1 gene. In another embodiment, the disclosure relates to grain comprising an embryo, wherein the embryo comprises one or more non-transgenic mutations in a Lip1 gene.

In another embodiment, the grain, flour, bran, or starch comprises one or more non-transgenic mutations in the Lip1 genes including but not limited to the mutations recited in Tables 1-3 for wheat and Table 4 for rice and the corresponding mutations in homoeologues. In still another embodiment, the disclosure relates to grain or flour comprising at least one non-transgenic mutation in the Lip1 gene in one, two or three genomes.

In still another embodiment, the disclosure relates to a wheat grain, flour or starch comprising one or more non-transgenic mutations in the Lip-A1 gene. In another embodiment, the non-transgenic mutations are identical in both alleles of the Lip-A1 gene of the A genome.

In one embodiment, the wheat grain, flour or starch comprises one or more non-transgenic mutations in both alleles of the Lip-D1 gene in the D genome. In another embodiment, the non-transgenic mutations are identical in both alleles of the Lip-D1 gene of the D genome.

In one embodiment, the wheat grain, flour or starch comprises one or more non-transgenic mutations in both alleles of the Lip-B1 gene in the B genome. In another embodiment, the non-transgenic mutations are identical in both alleles of the Lip-B1 gene of the B genome.

In one embodiment, the disclosure relates to wheat grain, wheat flour or starch comprising a polynucleotide of the Lip-A1 gene in the A genome with one or more non-transgenic mutations listed in Table 1 and corresponding to SEQ ID NO: 1. In another embodiment, the wheat grain or wheat flour comprise a polynucleotide with one or more non-transgenic mutations listed in Table 1 and is 85%, 86%, 87%, 88%, 89%, 90%, 91%, 92%, 93%, 94%, 95%, 96%, 97%, 98%, 99% or greater than 99% identical or similar to SEQ ID NO: 1.

In still another embodiment, wheat grain, wheat flour or starch comprise a polynucleotide with one or more non-transgenic mutations listed in Table 1 that codes for a Lip1 protein, wherein the Lip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 3.

In one embodiment, the disclosure relates to wheat grain, wheat flour or starch comprising a polynucleotide of the Lip-D1 gene in the D genome with one or more non-transgenic mutations listed in Table 2 and corresponding to SEQ ID NO: 4. In another embodiment, the wheat grain or wheat flour comprise a polynucleotide with one or more non-transgenic mutations listed in Table 2 and is 85%, 86%, 87%, 88%, 89%, 90%, 91%, 92%, 93%, 94%, 95%, 96%, 97%, 98%, 99% or greater than 99% identical or similar to SEQ ID NO: 4.

In still another embodiment, wheat grain, wheat flour or starch comprise a polynucleotide with one or more non-transgenic mutations listed in Table 2 that codes for a Lip-D1 protein, wherein the Lip-D1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 6.

In one embodiment, the disclosure relates to wheat grain, wheat flour or starch comprising a polynucleotide of the Lip-B1 gene in the B genome with one or more non-transgenic mutations listed in Table 3 and corresponding to SEQ ID NO: 7. In another embodiment, the wheat grain or wheat flour comprise a polynucleotide with one or more non-transgenic mutations listed in Table 3 and is 85%, 86%, 87%, 88%, 89%, 90%, 91%, 92%, 93%, 94%, 95%, 96%, 97%, 98%, 99% or greater than 99% identical or similar to SEQ ID NO: 7.

In still another embodiment, wheat grain, wheat flour or starch comprise a polynucleotide with one or more non-transgenic mutations listed in Table 3 that codes for a Lip-B1 protein, wherein the Lip-B1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 9.

In still another embodiment, the disclosure relates to wheat grain or flour comprising an endosperm and a reduced gene expression level, activity or expression level and activity of the Lip1 gene as compared to wild type wheat grain or flour.

In yet another embodiment, the disclosure relates to wheat grain or flour with one or more mutations in the Lip1 gene exhibiting increased shelf life as compared to wild type wheat grain or flour. In another embodiment, wheat grain or flour with one or more mutations in the Lip1 gene exhibits from 0-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In yet another embodiment, the disclosure relates to wheat grain or flour with one or more mutations in the Lip-A1 gene exhibiting increased shelf life as compared to wild type wheat grain or flour. In another embodiment, wheat grain or flour with one or more mutations in the Lip-A1 gene exhibits from 0-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In yet another embodiment, the disclosure relates to wheat grain or flour with one or more mutations in the Lip-D1 gene exhibiting increased shelf life as compared to wild type wheat grain or flour. In another embodiment, wheat grain or flour with one or more mutations in the Lip-D1 gene exhibits from 0-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In yet another embodiment, the disclosure relates to wheat grain or flour with one or more mutations in the Lip-B1 gene exhibiting increased shelf life as compared to wild type wheat grain or flour. In another embodiment, wheat grain or flour with one or more mutations in the Lip-B1 gene exhibits from 0-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In yet another embodiment, the disclosure relates to wheat grain or flour with one or more mutations in the Lip-A1 and Lip-D1 genes exhibiting increased shelf life as compared to wild type wheat grain or flour. In another embodiment, wheat grain or flour with one or more mutations in the Lip-A1 and Lip-D1 genes exhibits from 0-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In yet another embodiment, the disclosure relates to wheat grain or flour with one or more mutations in the Lip-A1 and Lip-B1 genes exhibiting increased shelf life as compared to wild type wheat grain or flour. In another embodiment, wheat grain or flour with one or more mutations in the Lip-A1 and Lip-B1 genes exhibits from 0-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In yet another embodiment, the disclosure relates to wheat grain or flour with one or more mutations in the Lip-B1 and Lip-D1 genes exhibiting increased shelf life as compared to wild type wheat grain or flour. In another embodiment, wheat grain or flour with one or more mutations in the Lip-B1 and Lip-D1 genes exhibits from 0-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In yet another embodiment, the disclosure relates to wheat grain or flour with one or more mutations in the Lip-A1, Lip-B1 and Lip-D1 genes exhibiting increased shelf life as compared to wild type wheat grain or flour. In another embodiment, wheat grain or flour with one or more mutations in the Lip-A1, Lip-B1 and Lip-D1 genes exhibits from 0-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain or flour.

In still another embodiment, the disclosure relates to rice grain comprising one or more non-transgenic mutations in the OsLip1 gene. In another embodiment, the non-transgenic mutations are identical in both alleles of the OsLip1 gene.

In one embodiment, the disclosure relates to rice grain comprising a polynucleotide of the OsLip1 gene with one or more non-transgenic mutations listed in Table 4 and corresponding to SEQ ID NO: 26. In another embodiment, the rice grain comprises a polynucleotide with one or more non-transgenic mutations listed in Table 4 and is 85%, 86%, 87%, 88%, 89%, 90%, 91%, 92%, 93%, 94%, 95%, 96%, 97%, 98%, 99% or greater than 99% identical or similar to SEQ ID NO: 26.

In still another embodiment, rice grain comprise a polynucleotide with one or more non-transgenic mutations listed in Table 4 that codes for a Lip1 protein, wherein the Lip1 protein comprises one or more non-transgenic mutations and is 85%, 86%, 87%, 88%, 89%, 90%, 91%, 92%, 93%, 94%, 95%, 96%, 97%, 98%, 99% or greater than 99% identical or similar to SEQ ID NO: 28.

In yet another embodiment, the disclosure relates to rice grain with one or more mutations in the OsLip1 gene exhibiting increased shelf life as compared to wild type rice grain.

In another embodiment, rice grain with one or more mutations in the Lip1 gene exhibits from 0-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% increased shelf life as compared to wild type grain.

X. Food Products

In one embodiment, the disclosure is directed to a flour or other product produced from the grain or flour discussed above. In another embodiments, the flour, the coarse fraction or purified starch may be a component of a food product. In one embodiment, a food product is produced from wheat grain disclosed herein. In still another embodiment, a food product is produced from rice grain disclosed herein.

The food product includes but is not limited to a bagel, a biscuit, a bread, a bun, a croissant, a dumpling, an English muffin, a muffin, a pita bread, a quickbread, a refrigerated/frozen dough products, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In one embodiment, the flour is a whole grain flour (ex.—an ultrafine-milled whole grain flour, such as an ultrafine-milled whole grain wheat flour). In one embodiment, the whole grain flour includes a refined flour constituent (ex.—refined wheat flour or refined flour) and a coarse fraction (ex.—an ultrafine-milled coarse fraction). Refined wheat flour may be flour which is prepared, for example, by grinding and bolting (sifting) cleaned wheat. The Food and Drug Administration (FDA) requires flour to meet certain particle size standards in order to be included in the category of refined wheat flour. The particle size of refined wheat flour is described as flour in which not less than 98% passes through a cloth having openings not larger than those of woven wire cloth designated "212 micrometers (U.S. Wire 70)."

In another embodiment, the coarse fraction includes at least one of: bran and germ. For instance, the germ is an embryonic plant found within the wheat kernel. The germ includes lipids, fiber, vitamins, protein, minerals and phytonutrients, such as flavonoids. The bran may include several cell layers and has a significant amount of lipids, fiber, vitamins, protein, minerals and phytonutrients, such as flavonoids.

For example, the coarse fraction or whole grain flour or refined flour of the present invention may be used in various amounts to replace refined or whole grain flour in baked goods, snack products, and food products. The whole grain flour (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In another embodiment, the whole grain flour or coarse fraction or refined flour may be a component of a nutritional supplement. The nutritional supplement may be a product that is added to the diet containing one or more ingredients, typically including: vitamins, minerals, herbs, amino acids, enzymes, antioxidants, herbs, spices, probiotics, extracts, prebiotics and fiber.

In a further embodiment, the nutritional supplement may include any known nutritional ingredients that will aid in the overall health of an individual, examples include but are not limited to carotenoids, vitamins, minerals, other fiber components, fatty acids, antioxidants, amino acids, peptides, proteins, lutein, ribose, omega-3 fatty acids, and/or other nutritional ingredients. Because of the high nutritional content of the endosperm of the present invention, there may be many uses that confer numerous benefits to an individual, including, delivery of fiber and other essential nutrients, increased digestive function and health, weight management, blood sugar management, heart health, diabetes risk reduction, potential arthritis risk reduction, and overall health and wellness for an individual.

In still another embodiments, the whole grain flour or coarse fraction or refined flour may be a component of a dietary supplement. The Code of Federal Regulations defines a dietary supplement as a product that is intended to supplement the diet and contains one or more dietary ingredients including: vitamins, minerals, herbs, botanicals, amino acids, and other substances or their constituents; is intended to be taken by mouth as a pill, capsule, tablet, or liquid; and is labeled on the front panel as being a dietary supplement.

In yet another embodiment, the whole grain flour or coarse fraction or refined flour may be a fiber supplement or a component thereof. The fiber supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage.

In another embodiment, the whole grain flour or coarse fraction or refined flour may be included as a component of a digestive supplement. The whole grain flour or coarse fraction or refined flour may be a component of a digestive supplement alone or in combination with one or more prebiotic compounds and/or probiotic organisms. Prebiotic compounds are non-digestible food ingredients that may beneficially affect the host by selectively stimulating the growth and/or the activity of a limited number of microorganisms in the colon. Examples of prebiotic compounds within the scope of the invention, may include, but are not limited to: oligosaccharides and inulins.

Probiotics are microorganisms which, when administered in adequate amounts, confer a health benefit on the host. Probiotic organisms include, but are not limited to: *Lactobacillus, Bifidobacteria, Escherichia, Clostridium, Lactococcus, Streptococcus, Enterococcus*, and *Saccharomyces*.

In yet another embodiment, the whole grain flour or coarse fraction or refined flour may be included as a component of a functional food. The Institute of Food Technologists defines functional foods as, foods and food components that provide a health benefit beyond basic nutrition. This includes conventional foods, fortified, enriched, or enhanced foods, and dietary supplements. The whole grain flour and coarse fraction or refined flour include numerous vitamins and minerals, have high oxygen radical absorption capacities, and are high in fiber, making them ideally suited for use in/as a functional food.

In another embodiment, the whole grain flour or coarse fraction or refined flour may be used in medical foods. Medical food is defined as a food that is formulated to be consumed or administered entirely under the supervision of a physician and which is intended for the specific dietary management of a disease or condition for which distinctive nutritional requirements, based on recognized scientific principles, are established by medical evaluation. The nutrient contents and antioxidant capacities of the whole grain flour and coarse fraction or refined flour make them ideal for use in medical foods.

In yet another embodiment, the whole grain flour or coarse fraction or refined flour may also be used in pharmaceuticals. The whole grain flour and coarse fraction or refined flour are high in fiber and have a very fine granulation making them suitable for use as a carrier in pharmaceuticals.

In still another embodiment, delivery of the whole grain flour or coarse fraction or refined flour as a nutritional supplement, dietary supplement or digestive supplement is contemplated via delivery mechanisms where the whole grain flour or coarse fraction is the single ingredient or one of many nutritional ingredients. Examples of delivery mechanisms include but are not limited to: instant beverage mixes, ready-to-drink beverages, nutritional bars, wafers, cookies, crackers, gel shots, capsules, and chews.

In yet another embodiment, a milling process may be used to make a multi-wheat flour, or a multi-grain coarse fraction. In one embodiment, bran and germ from one type of wheat may be ground and blended with ground endosperm or whole grain wheat flour of another type of wheat. Alternatively bran and germ of one type of grain may be ground and blended with ground endosperm or whole grain flour of another type of grain.

In still another embodiment, bran and germ from a first type of wheat or grain may be blended with bran and germ from a second type of wheat or grain to produce a multi-grain coarse fraction. It is contemplated that the invention encompasses mixing any combination of one or more of bran, germ, endosperm, and whole grain flour of one or more grains. This multi-grain, multi-wheat approach may be used to make custom flour and capitalize on the qualities and nutritional contents of multiple types of grains or wheats to make one flour.

The whole grain flour of the invention may be produced via a variety of milling processes. One exemplary process involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like.

After grinding, the grain is discharged and conveyed to a sifter. Any sifter known in the art for sifting a ground particle may be used. Material passing through the screen of the sifter is the whole grain flour of the invention and requires no further processing. Material that remains on the screen is referred to as a second fraction. The second fraction requires additional particle reduction. Thus, this second fraction may be conveyed to a second passage grinder.

After grinding, the second fraction may be conveyed to a second sifter. Material passing through the screen of the second sifter is the whole grain flour. The material that remains on the screen is referred to as the fourth fraction and requires further processing to reduce the particle size. The fourth fraction on the screen of the second sifter is conveyed back into either the first passage grinder or the second passage grinder for further processing via a feedback loop.

It is contemplated that the whole grain flour, coarse fraction, purified starch and/or grain products of the disclosure may be produced by a number of milling processes known in the art.

In another embodiment, the bran fraction is from rice and products are derived from it such as rice bran oil.

XI. Plant Breeding

In another embodiment, the disclosure is directed to methods for plant breeding using wheat plants and plant parts with one or more non-transgenic mutations in the Lip1 genes.

One such embodiment is the method of crossing wheat variety with one or more non-transgenic mutations in the Lip1 genes with another variety of wheat to form a first generation population of F1 plants. The population of first generation F1 plants produced by this method is also an embodiment of the invention. This first generation population of F1 plants will comprise an essentially complete set of the alleles of wheat variety with one or more non-transgenic mutations in the Lip1 genes. One of ordinary skill in the art can utilize either breeder books or molecular methods to identify a particular F1 plant produced using wheat variety with one or more non-transgenic mutations in the Lip1 genes, and any such individual plant is also encompassed by this invention. These embodiments also cover use of transgenic or backcross conversions of wheat varieties with one or more mutations in the Lip1 genes to produce first generation F1 plants.

In another embodiment, the invention relates to a method of developing a progeny wheat plant. A method of developing a progeny wheat plant comprises crossing a wheat variety with one or more non-transgenic mutations in the Lip1 genes with a second wheat plant and performing a breeding method. A specific method for producing a line derived from wheat variety with one or more non-transgenic mutations in the Lip1 genes is as follows.

One of ordinary skill in the art would cross wheat variety with one or more non-transgenic mutations in the Lip1 gene or genes with another variety of wheat, such as an elite variety. The F1 seed derived from this cross would be grown to form a homogeneous population. The F1 seed would contain one set of the alleles from wheat variety with one or more non-transgenic mutations in the Lip1 gene and one set of the alleles from the other wheat variety.

The F1 genome would be made-up of 50% wheat variety with one or more non-transgenic mutations in the Lip1 gene and 50% of the other elite variety. The F1 seed would be grown to form F2 seed. The F1 seed could be allowed to self, or bred with another wheat cultivar.

On average the F2 seed would have derived 50% of its alleles from wheat variety with one or more non-transgenic mutations in the Lip1 gene and 50% from the other wheat variety, but various individual plants from the population would have a much greater percentage of their alleles derived from wheat variety with one or more non-transgenic mutations in the Lip1 gene (Wang J. and R. Bernardo, 2000, Crop Sci. 40:659-665 and Bernardo, R. and A. L. Kahler, 2001, Theor. Appl. Genet. 102:986-992).

The F2 seed would be grown and selection of plants would be made based on visual observation and/or measurement of traits and/or marker assisted selection. The wheat variety with one or more non-transgenic mutations in the Lip1 gene-derived progeny that exhibit one or more of the desired wheat variety with one or more non-transgenic mutations in the Lip1 gene-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable wheat variety with one or more non-transgenic mutations in the Lip1 gene-derived traits.

The process of growing and selection would be repeated any number of times until a homozygous wheat variety with one or more non-transgenic mutations in the Lip1 gene-derived wheat plant is obtained. The homozygous wheat variety with one or more non-transgenic mutations in the Lip1 gene-derived wheat plant would contain desirable traits derived from wheat variety with one or more non-transgenic mutations in the Lip genes, some of which may not have been expressed by the other original wheat variety to which wheat variety with one or more non-transgenic mutations in the Lip1 gene was crossed and some of which may have been expressed by both wheat varieties but now would be at a level equal to or greater than the level expressed in wheat variety with one or more non-transgenic mutations in the Lip1 gene or genes.

The breeding process, of crossing, selfing, and selection may be repeated to produce another population of wheat variety with one or more non-transgenic mutations in the Lip1 gene-derived wheat plants with, on average, 25% of their genes derived from wheat variety with one or more non-transgenic mutations in the Lip1 gene, but various individual plants from the population would have a much greater percentage of their alleles derived from wheat variety with one or more non-transgenic mutations in the Lip1 gene or genes. Another embodiment of the invention is a homozygous wheat variety with one or more non-transgenic mutations in the Lip gene-derived wheat plant that has received wheat variety with one or more non-transgenic mutations in the Lip gene-derived traits. This breeding process can be repeated as many times as desired.

The disclosure is further described by the following paragraphs:

1. A plant comprising one or more mutations in the Lip1 gene, wherein said one or more mutations contributes to a product from said plant having a characteristic selected from the group consisting of: (a) increased shelf life; (b) reduced TAG to FFA production; (c) increased oxidative stability; (d) increased hydrolytic stability; (e) reduced hexanal production; and (f) improved sensory characteristics.
2. A wheat plant comprising a mutation in the Lip1 gene, wherein said mutation contributes to milled grain from said wheat plant having increased shelf-life compared to milled grain from a wild type wheat plant.
3. A wheat plant comprising a mutation in the Lip1 gene, wherein said mutation contributes to reduced TAG to FFA production in flour from grain of said plant as compared to flour from grain of a wild type wheat plant.
4. A wheat plant comprising a mutation in the Lip1 gene, wherein said mutation contributes to increased hydrolytic stability of products produced from said plant as compared to products produced from a wild type wheat plant.
5. A wheat plant comprising a mutation in the Lip1 gene, wherein said mutation contributes to increased oxidative stability of products produced from said plant as compared to products produced from a wild type wheat plant.
6. A wheat plant comprising a mutation in the Lip1 gene, wherein said mutation contributes to reduced hexanal production in flour from grain of said plant as compared to flour from grain of a wild type wheat plant.
7. A wheat plant comprising a mutation in the Lip1 gene, wherein said mutation contributes to products from said wheat plant having improved sensory aspects as compared to sensory aspects of products from a wild type wheat plant.
8. The wheat plant of any of the preceding paragraphs, further comprising one or more mutations in at least two genomes.
9. The wheat plant of any of the preceding paragraphs comprising one or more mutations in the A and B genomes.
10. The wheat plant of any of the preceding paragraphs comprising one or more mutations in the A and D genomes.
11. The wheat plant of any of the preceding paragraphs, further comprising one or more mutations in the A, B, and D genomes.
12. A wheat plant comprising one or more mutations in the Lip1 gene in the A genome, wherein said mutation contributes to products from said wheat plant having increased shelf-life compared to products from a wild type wheat plant.
13. A wheat plant comprising one or more mutations in the Lip1 gene in the A genome, wherein said mutation contributes to reduced TAG to FFA production from stored grain from said plant as compared to stored grain from a wild type wheat plant.
14. The wheat plant of any of the preceding paragraphs, wherein the Lip1 gene is Lip-A1.
15. The wheat plant of any of the preceding paragraphs, further comprising a mutation in the Lip1 gene of the D genome.
16. A wheat plant comprising one or more mutations in the Lip1 gene in the D genome, wherein said mutation contributes to products from said wheat plant having increased shelf-life compared to products from a wild type wheat plant.
17. A wheat plant comprising one or more mutations in the Lip1 gene in the D genome, wherein said mutation contributes to reduced TAG to FFA production in grain from said plant as compared to stored grain from a wild type wheat plant.
18. The wheat plant of any of the preceding paragraphs, wherein the Lip1 gene is Lip-D1.
19. The wheat plant of any of the preceding paragraphs further comprising two or more mutations in the Lip1 gene, wherein the mutations in the Lip1 gene are on at least two different genomes.

20. The wheat plant of any of the preceding paragraphs, further comprising a reduced level of Lip1 protein, relative to a wild-type wheat plant.

21. The wheat plant of any of the preceding paragraphs, further comprising reduced Lip1 enzyme activity relative to a wild-type wheat plant.

22. The wheat plant of any of the preceding paragraphs where the wheat plant is homozygous for the mutation.

23. The wheat plant of any of the preceding paragraphs, wherein products from said wheat plant have increased hydrolytic stability as compared to products from a wild type wheat plant.

24. The wheat plant of any of the preceding paragraphs, wherein products from said wheat plant have increased oxidative stability as compared to products from a wild type wheat plant.

25. The wheat plant of any of the preceding paragraphs, which is *Triticum aestivum* ssp. *aestivum*.

26. The wheat plant of any of the preceding paragraphs, which is *Triticum durum* or *Triticum turgidum* subsp. Durum.

27. The wheat plant of any of the preceding paragraphs, wherein the one or more mutations in the Lip1 gene is recited in any one of Tables 1-3.

28. The wheat plant of any of the preceding paragraphs, wherein the one or more mutations in the Lip1 gene results in an amino acid change recited in Tables 1-3 in the Lip1 protein.

29. A rice plant comprising one or more mutations in the OsLip1 gene, wherein said mutation contributes to rice seeds or bran from said rice plant having increased shelf-life compared to rice seeds or bran from a wild type rice plant.

30. A rice plant comprising one or more mutations in the OsLip1 gene, wherein said mutation contributes to reduced TAG to FFA production rice seeds or bran from said rice plant as compared to rice seeds or bran of a wild type rice plant.

31. A rice plant comprising one or more mutations in the OsLip1 gene, wherein said mutation contributes to increased hydrolytic stability of products produced from said rice plant as compared to products produced from a wild type rice plant.

32. A rice plant comprising one or more mutations in the OsLip1 gene, wherein said mutation contributes to increased oxidative stability of products produced from said plant as compared to products produced from a wild type rice plant.

33. A rice plant comprising one or more mutations in the OsLip1 gene, wherein said mutation contributes to reduced hexanal production in rice seeds or bran of said plant as compared to rice seeds or bran from a wild type rice plant.

34. A rice plant comprising one or more mutations in the OsLip1 gene, wherein said mutation contributes to products from said rice plant having improved sensory aspects as compared to sensory aspects of products from a wild type rice plant.

35. The rice plant of any of the preceding paragraphs, wherein the one or more mutations in the OsLip1 gene is recited in Table 4.

36. The rice plant of any of the preceding paragraphs, further comprising a reduced level of OsLip1 protein, relative to a wild-type rice plant.

37. The rice plant of any of the preceding paragraphs, further comprising reduced OsLip1 enzyme activity relative to a wild-type rice plant.

38. The rice plant of any of the preceding paragraphs where the rice plant is homozygous for the mutation.

39. Grain or seed from the plant of any of the preceding paragraphs, wherein the production of decomposition products of triacylglycerides is decreased in grain or seed made from said plant as compared to wild type grain or seed.

40. Grain or seed from the plant of any of the preceding paragraphs, wherein the production of decomposition products of triacylglycerides is decreased in grain or seed by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% as compared to grain or seed from a wild type plant.

41. Grain or seed from the plant of any of the preceding paragraphs, wherein the production of hexanal, or trans-2-nonenal, or trihydroxydecanoic acid or combinations thereof is decreased in grain or seed by at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95% as compared to grain or seed from a wild type plant.

42. Grain from the plant of any of the preceding paragraphs, wherein shelf life of whole grain flour made from wheat grain is increased by 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, or greater than 30 months as compared to the shelf life of grain or seed made from wild-type grain.

43. Grain comprising a mutation in an Lip1 gene, wherein said mutation contributes to reduced free fatty acid production in whole grain flour from said grain as compared to grain from a wild type wheat plant.

44. Grain comprising a mutation in an Lip1 gene, wherein said mutation contributes to increased shelf-life in whole grain flour from said grain as compared to grain from a wild type wheat plant.

45. Grain comprising a mutation in an Lip1 gene, wherein said mutation contributes to increased shelf-life in whole grain flour stored at a higher temperature as compared to grain from a wild type wheat plant.

46. Grain from the plant of any of the preceding paragraphs, wherein shelf life of whole grain flour made from wheat grain is improved as determined by sensory characteristics including color, flavor, texture, aroma, performance or overall preference of the finished product.

47. Rice seed or bran comprising a mutation in an OsLip1 gene, wherein said mutation contributes to reduced free fatty acid production in rice seed or bran from a rice plant as compared to rice seed or bran from a wild type rice plant.

48. Rice seed or bran comprising a mutation in an OsLip1 gene, wherein said mutation contributes to increased shelf-life in rice seed or bran from said rice plant as compared to rice seed or bran from a wild type rice plant.
49. Rice seed or bran comprising a mutation in an OsLip1 gene, wherein said mutation contributes to increased shelf-life in rice seed or bran stored at a higher temperature as compared to rice seed or bran from a wild type rice plant.
50. Rice seed or bran from the plant of any of the preceding paragraphs, wherein shelf life of rice seed or bran is improved as determined by sensory characteristics including color, flavor, texture, aroma, performance or overall preference of the finished product.
51. Rice seed or bran from the rice plant of any of the preceding paragraphs, wherein shelf life of rice seed or bran from said rice plant is increased by 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, or greater than 30 months as compared to the rice seed or bran from a wild-type plant.
52. Wheat grain from a wheat plant of any of the preceding paragraphs.
53. Flour comprising wheat grain of any of the preceding paragraphs.
54. A food product comprising a component of a wheat plant of any of the preceding paragraphs.
55. A wheat seed, plant part or progeny thereof from a wheat plant of any of the preceding paragraphs.
56. A wheat plant substantially as shown and described herein.
57. Grain substantially as shown and described herein.
58. Wheat seed, plant part or progeny thereof from a wheat plant substantially as shown and described herein.
59. Rice seed or bran from a rice plant of any of the preceding paragraphs.
60. A food product comprising a component of a rice plant of any of the preceding paragraphs.
61. A rice seed, plant part or progeny thereof from a rice plant of any of the preceding paragraphs.
62. A rice plant substantially as shown and described herein.
63. Rice seed and rice bran substantially as shown and described herein.
64. Rice seed, plant part or progeny thereof from a rice plant substantially as shown and described herein.

Example 1

This example describes the identification of novel alleles of Lip1.

A. Identification of Wheat and Rice Lipase 1 Genes

Figure 1:
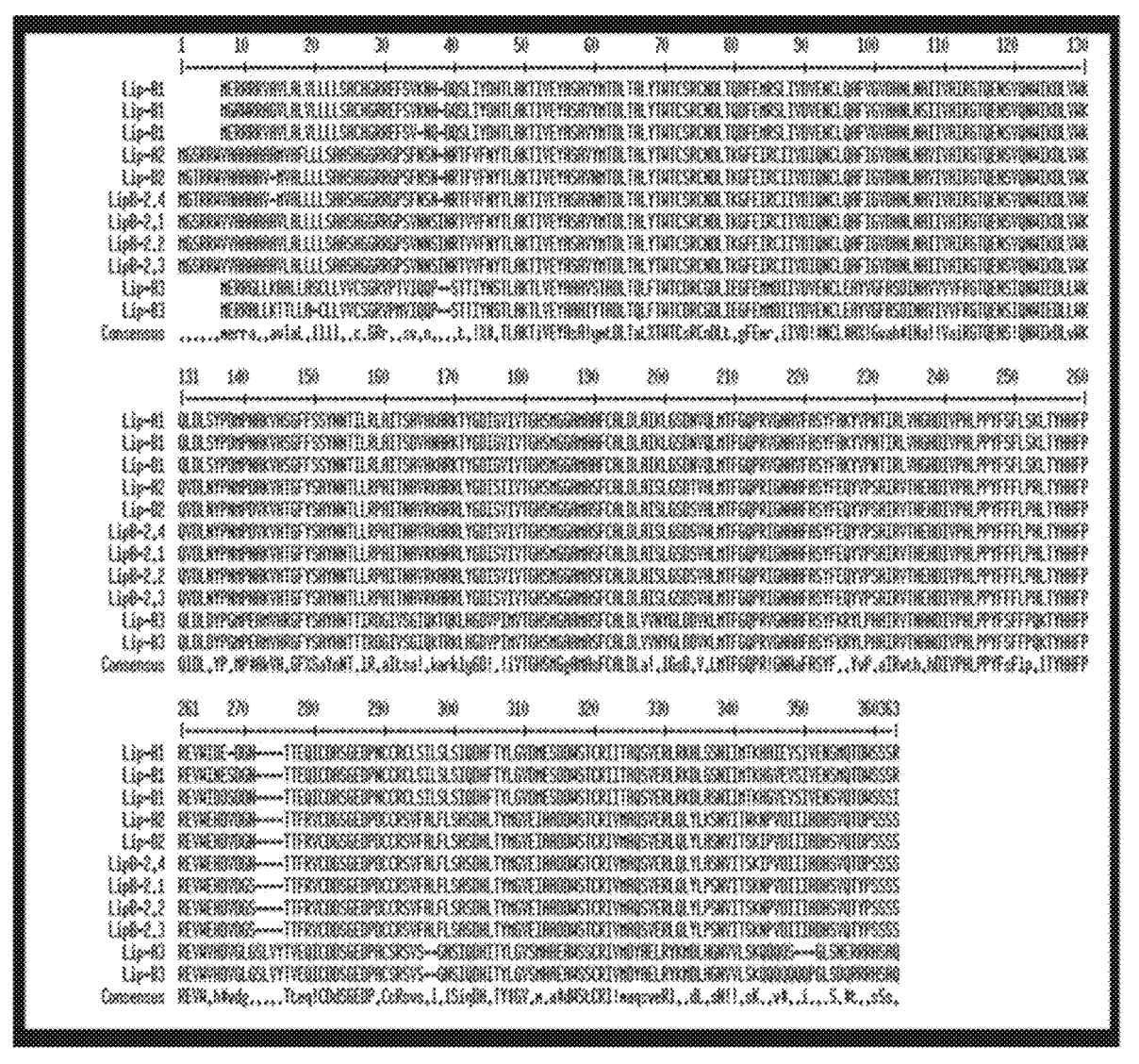

Multiple wheat lipase gene sequences were identified by homology to rice bran lipase II protein sequence (LOC_Os07g47250) using tblastn algoritm on public wheat genome databases. An alignment of the most similar identified translated wheat protein sequences is shown in FIG. 1. In order to assess gene expression for each of the wheat Lipase gene families Lip1, 2 and 3, reverse transcription PCR (RT-PCR) was used Freeman WM, Walker SJ, Vrana KE (January 1999). "*Quantitative RT-PCR: pitfalls and potential*". *BioTechniques* 26 (1): 112-22, 124-5. Total RNA was extracted from leaves from one week old plants, leaves from 4 weeks old plants, developing grains at 6 days post anthesis (DPA), developing grain at 18 DPA, mature grains, roots from 1 week old plants, and stems from 1 week old plants. Tissue was ground in liquid nitrogen and extracted using Qiagen RNeasy plant kit following manufacturer's instructions. For developing and mature seed, total RNA was extracted from frozen ground tissue using 1 mL solution containing 50 mM Tris-HCl (pH 9.0), 200 mM NaCl, 1% sarcosyl, 20 mM EDTA, and 5 mM DTT (Sigma-Aldrich. St. Louis, MO) as described by Verlotta et al BMC Plant Biology 10:263 (2010). After incubation for 5 minutes at room temperature, RNA was extracted using Trizol reagent (Invitrogen, Carlsbad, CA) followed by Qiagen RNeasy plant kit with buffer RLT following manufacturer instructions. Extracted RNA was treated in solution with DNAse I with a modified manufacturer's protocol using 3.5 µl of DNase per sample at a total incubation time of 30 minutes at room temperature (RNase free DNAse Kit, Qiagen, Valencia, CA) and then purified on RNeasy columns. Total RNA concentration and purity was quantified on a Nanodrop 2000c spectrophotometer (ThermoFisher Scientific, Grand Island, NY). 168 ng of Total RNA was used to evaluate genomic contamination and quality using an AdvanCE FS96 Fragment Analyzer (Advanced Analytical, Ames, IA). Lack of genomic contamination of RNA was confirmed by PCR and sequencing.

A total of 0.5 µg RNA was reverse transcribed using SuperScript III First-Strand Synthesis SuperMix following the manufacturer instructions (Invitrogen, Carlsbad, CA). cDNA were diluted 1:250, and 5 µl was used as a template for PCR in a 20l volume. Each reaction consisted of 1× Ex-Taq Buffer (Takara Biotechnology, Mountain View, CA), 0.125 mM dNTPs (Takara Biotechnology, Mountain View, CA), 0.125 µM each forward and reverse primers, and 0.83 U Ex-Taq Polymerase (Takara Biotechnology, Mountain View, CA). Primers for Glyceraldehyde 3-phosphate dehydrogenase (GAPD) were used as a control. (Jarosova et al. BMC Plant Biology 10 146 (2010)). PCR primers for Lip1 (SEQ ID NOs:18-19) Lip 2 (SEQ ID NOs:20-21) Lip3 (SEQ ID NOs: 22-23) and GAPD (SEQ ID NOs: 24-25) were used to evaluate gene expression as shown in FIG. 2. PCR conditions were 95° C. for 2 minutes, 30 cycles of 95° C. for 30 seconds, 60° C. for 30 seconds and 72° C. for 30 seconds followed by a final extension at 72° C. for 5 minutes. PCR products were separated on 1.1% agarose gels, and documented with a Bio-Rad Gel Imaging System (Bio-Rad, Hercules, CA, USA).

Figure 3:
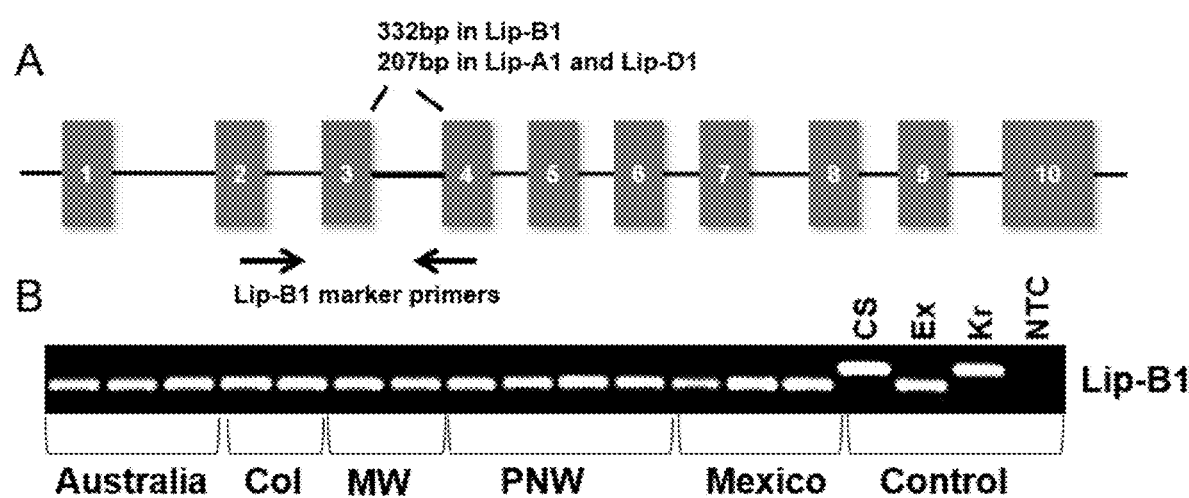
FIG. 3 shows the (A) Gene model of Lip-B1 of wheat. Boxes represent exons (numbered) and lines represent introns. Lip-B1 marker primers amplify a 332 bp PCR product in wheat varieties with intact Lip-B1 sequences and a 207 bp band representing Lip-A1 and Lip-D1 in varieties lacking this region of Lip-B1 sequence. (B) PCR products of Lip-B1 marker indicating that many varieties lack Lip-B1 sequence and that CS and Kr contain Lip-B1 sequences. CS—Chinese Spring, Ex—Express, Kr—Kronos, NTC—no template control.

Lip-B1 sequences were identified in the public databases for hexaploid wheat variety, Chinese Spring. However, PCR amplification of hexaploid wheat variety Express and other varieties indicated that all or part of this gene was missing in some hexaploid wheat varieties. Lip-B1 marker primers (SEQ ID NOs: 16-17) are exemplary primers that have proven useful as a marker to identify wheat varieties containing or lacking some or all of Lip-B1 genomic sequences (FIG. 3). Durum wheat variety Kronos had Lip-B1 sequence in the genome and mutation alleles were identified in that gene (Table 3).

B. Mutagenesis

In accordance with one exemplary embodiment of the present invention, wheat seeds of the hexaploid cultivar (*Triticum aestivum*) Express were vacuum infiltrated in H$_2$O (approximately 1,000 seeds/100 ml H$_2$O for approximately 4 minutes). The seeds were then placed on a shaker (45 rpm) in a fume hood at room temperature. The mutagen ethyl methanesulfonate (EMS) was added to the imbibing seeds to final concentrations ranging from about 0.75% to about 1.2% (v/v). Following an 18-hour incubation period, the EMS solution was replaced 4 times with fresh H$_2$O.

Rice seeds of the cultivar (*Oryza sativa*) IR64 or Cypress were vacuum infiltrated in H$_2$O (approximately 1,000 seeds/100 ml H$_2$O for approximately 4 minutes). The seeds were then placed on a shaker (45 rpm) in a fume hood at room temperature. The mutagen N-ethyl-N-nitrosourea (ENU) was added to the imbibing seeds to final concentrations from about 0.2, 0.3 or 0.5% for 5.5, 6 or 7 hours. In some cases a combination of EMS (0.2M) and ENU (0.15M) was used.

The seeds were then rinsed under running water for about 4-8 hours. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

C. DNA Preparation

DNA from the M2 plants produced in accordance with the above description was extracted and prepared in order to identify which M2 plants carried a mutation at one or more of their Lip1 loci. The M2 plant DNA was prepared using methods and reagents based on the Qiagen® (Valencia, CA) DNeasy® 96 Plant Kit. Approximately 50 mg of frozen plant sample was placed in each sample tube with a stainless steel bead, frozen in liquid nitrogen and ground 2 times for 45 seconds each at 21.5 Hz using the Retsch® Mixer Mill MM 300. Next, 300 µl of solution AP1 [Buffer AP1, solution DX and RNAse (100 mg/ml)] at 80° C. was added to each sample. The tubes were sealed and shaken for 15 seconds, then briefly centrifuged at 5,200×g. Following the addition of 100 µl Buffer P3, the tubes were shaken for 15 seconds. The samples were placed in a freezer at −20° C. for at least 20 min. The samples were then centrifuged for 20 minutes at 5,200×g. A filter plate was placed on the vacuum unit of Tecan Evo liquid handling robot and 400 µl of Buffer AW1 was added to each well. Following the addition of a 300 µl aliquot of supernatant to each well, vacuum was applied until dryness. Next, 650 µl of Buffer AW2 was added to each well of the filter plate. The filter plate was placed on a square well block and centrifuged for 20 minutes at 5,200×g. The filter plate was then placed on a new set of sample tubes and 90 µl of Buffer AE was applied to the filter. It was incubated at room temperature for 1 minute and then spun for 2 minutes at 5,200×g. This step was repeated with an additional 90 µl Buffer AE. The filter plate was removed and the tubes containing the pooled filtrates were capped. The individual samples were then normalized to a DNA concentration of 5 to 10 ng/µl for TILLING, or left un-normalized for genotyping applications.

D. Tilling

The M2 wheat DNA was pooled into groups of two individual plants. The DNA concentration for each individual within the pool was approximately 2 ng/µl with a final concentration of 4 ng/µl for the entire pool. The M2 rice DNA was pooled into groups of six individual plants. The DNA concentration for each individual within the pool was approximately 0.083 ng/µl or 0.17 ng/µl with a final concentration of 0.5 ng/µl or 1 ng/µl for the entire pool. Then, 5 µl of the pooled DNA samples was arrayed on microtiter plates and subjected to gene-specific PCR.

PCR amplification using SEQ IDs NOs: 10 and 11 (Lip-A1), or SEQ IDs NOs: 12 and 13 (Lip-D1) or SEQ IDs NOs:14 and 15 (Lip-B1), or SEQ IDs NOs: 29-30 was performed in 15 µl volumes containing 20 ng pooled DNA, 0.75× ExTaq buffer (Clonetech, Mountain View, CA), 1.1 mM additional MgCl$_2$, 0.3 mM dNTPs, 0.3 µM primers, 0.009 U Ex-Taq DNA polymerase (Clonetech, Mountain View, CA), 0.02 units DyNAzyme II DNA Polymerase (Thermo Scientific), and if necessary 0.33M Polymer-Aide PCR Enhancer (Sigma-Aldrich®). PCR amplification was performed using an MJ Research® thermal cycler as follows: 95° C. for 2 minutes; 8 cycles of "touchdown PCR" (94° C. for 20 second, followed by annealing step starting at 70-68° C. for 30 seconds and decreasing 1° C. per cycle, then a temperature ramp of 0.5° C. per second to 72° C. followed by 72° C. for 1 minute); 25-45 cycles of 94° C. for 20 seconds, 63 or 65° C. for 30 seconds, ramp 0.5° C./sec to 72° C., 72° C. for 1-2 minutes; 72° C. for 8 minutes; 98° C. for 8 minutes; 80° C. for 20 seconds; 60 cycles of 80° C. for 7 seconds-0.3 degrees/cycle.

PCR products (2-4 µl) were digested in 96-well plates. 3 µl of a solution containing 6 mM HEPES [4-(2-hydroxyethyl)-1-piperazineethanesulfonic acid] (pH 7.0), 6 mM MgCl$_2$, 6 mM NaCl, 0.012× Triton® X-100, 0.03 mg/ml of bovine serum albumin, 0.5× T-Digest Buffer [Advanced Analytical Technologies, Inc (AATI), Ames, IA], 0.912 U each of Surveyor® Endonuclease and Enhancer (Transgenomic®, Inc.), and 0.5× dsDNA Cleavage Enzyme (AATI, Ames, IA) was added to the PCR product. Digestion reactions were incubated at 45° C. for 45 minutes. The specific activity of the Surveyor enzyme was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 20 µl of Dilution Buffer E (AATI, Ames, IA) or 1×TE. The reactions were stored in the freezer until they were run on the Fragment Analyzer™ (AATI, Ames, IA) Capillary Electrophoresis System. Samples were run on the Fragment Analyzer™ utilizing the DNF-920-K1000T Mutation Discovery Kit (AATI, Ames, IA) according to the manufacturer's protocol.

After electrophoresis, the assays were analyzed using PROSize® 2.0 Software (AATI, Ames, IA). The gel image showed sequence-specific pattern of background bands common to all 96 lanes. Rare events, such as mutations, create new bands that stand out above the background pattern. Plants with bands indicative of mutations of interest were evaluated by TILLING individual members of a pool mixed with wild type DNA and then sequencing individual PCR products.

Example 2: Genotyping and Plant Breeding of Lip1 Lines

Plants carrying mutations confirmed by sequencing were grown as described above (e.g., the M3 plant could be backcrossed or outcrossed multiple times in order to eliminate background mutations and/or self-pollinated in order to create a plant that was homozygous for the mutation) or crossed to another plant containing Lip1 mutations in a different genome homoeolog and the process repeated. At each generation, the novel alleles were validated in the plant materials by extracting DNA, and genotyping by sequencing or by use of allele specific KASP (Kompetitive Allele Specific PCR) molecular markers (LGC Genomics, Beverly, MA) developed specifically for alleles of interest.

KASP genotyping was performed on DNA extracted from young leaves as described in Example 1. Each reaction consisted of 5 µl master mix (KASP High-Rox Universal 2× Master Mix, LGC Genomics) 0.14 µl KASP Assay Mix, and 40-60 ng DNA in a total reaction volume of 10.14 µl. The reaction mixture was then PCR amplified in a 96-well format using the following thermal cycling conditions: 94° C. for 15 minutes, then 10 cycles at 92° C. for 20 seconds followed by 61° C. for 60 seconds dropping 0.6° C. per cycle until reaching 55° C., then 35-40 cycles of 94° C. for 20 seconds followed by 55° C. for 60 seconds, and finally held at 8° C. until measurement. The subsequent reaction was evaluated at room temperature with a 7900 HT Fast Real-Time PCR system or QuantStudio 3system using controls of known genotypes (Applied Biosystems, Inc, Foster City, Ca, USA).

TABLE 6

Representative lines with combinations of mutation alleles in Lip-A1 and Lip-D1

| Line | Gene | Nucleotide Mutations | A.A. Mutation |
|---|---|---|---|
| 1 | Lip-A1 | G1514A | W63* |
|   | Lip-D1 | G1497A | W62* |
| 2 | Lip-A1 | G2141A | W122* |
|   | Lip-D1 | G2125A | W121* |
| 3 | Lip-A1 | G2141A | W122* |
|   | Lip-D1 | C1780T | Q88* |
| 4 | Lip-A1 | G1514A | W63* |
|   | Lip-D1 | C1780T | Q88* |

With regard to Table 6, the genomic nucleic acid designations of the mutations in Lip1 of the A genome named Lip-A1 correspond to the position in the reference sequence SEQ ID NO: 1. Amino acid designations of the Lip1 polypeptide of the A genome named Lip-A1 correspond to the amino acid position of reference sequence SEQ ID NO: 3. One exemplary mutation in Table 5 is G1514A, resulting in a change from guanine to adenine at nucleotide position 1514 identified according to its position in the sequence of Lip-A1 SEQ ID NO: 1. This mutation results in a change from a tryptophan to a stop (*) codon at amino acid position 63 (W63*) identified according to its position in the expressed protein of Lip-A1 (SEQ ID NO: 3). Genomic nucleic acid designations of the mutations in the Lip1 gene of the D genome named Lip-D1 correspond to the position in the reference sequence SEQ ID NO: 4. Amino acid designations of the mutations in the Lip1 gene of the D genome named Lip-D1 correspond to the amino acid position of reference sequence SEQ ID NO: 6.

Example 3: Improved Shelf-Life of Lip1 Novel Alleles

Analysis of Lipolytic Activity

For assessment of the impact of novel Lip1 allele combinations on shelf life of whole grain flour, seeds with moisture contents of approximately 10% were milled for 20 seconds at 22 1/s vibration frequency using a MixerMill 300 (Retsch GmbH, Haan, Germany) and 2 g samples of the resulting whole grain flour were stored in closed polyethylene bags. Accelerated aging of flour was conducted in a Percival E30BC8 (Percival Scientific Inc, Perry, Iowa, USA) with the temperature set at 37° C. for 6-8 weeks. Different incubation times and a range of additional milling, moisture content, storage media, temperatures and humidity conditions could also be employed for testing shelf life.

Analysis of triacylglycerides (TAG) and free fatty acid (FFA) contents in freshly milled and aged whole grain flour was performed to determine the content and profile of each (AOCS Method Ce 2b-11(2013); Christie W. (1993) Preparation of ester derivatives of fatty acids for chromatographic analysis. Advances in Lipid Methodology 2(69):e111). Two technical replicates on 2-5 biological replicates were analyzed for each genotypic combination. Briefly, lipids were extracted from duplicate samples of 500 mg whole grain wheat flour to which 10 mg/mL of an internal standard (TAG 15:0 Sigma-Aldrich®, St. Louis, MO) was added to a final concentration of 40 µg/mL. After adding 5 mL heptane, samples were placed on a platform shaker at low speed for 30 minutes, then centrifuged at 1760×g for 10 minutes at room temperature. The lipid layer was transferred and dried under a nitrogen stream (TurboVap®LV; Zymark, Hopkinton, MA). Lipids were resuspended in 1 mL of toluene and two 400-µL aliquots were transferred to fresh vials. A 2 mg/mL methyl ester standard (15:1 n-5 Nu-Check Prep, Inc., Elysian, MN) was added to a final concentration of 14.3p g/mL and also to a control vial as a derivatization blank. Alkali hydrolysis and methylation were performed by adding 1 mL of 0.5M dry methanolic sodium methoxide to a sample vial, capped, vortexed and heated at 65° C. for 1 hr. For acid catalyzed esterification and methylation, 1 mL of dry 3N methanolic HCl was added to the second sample vial, which was capped, vortexed and heated at 95° C. for 45 minutes. After vials were cooled, 1 mL of water and 1 mL of heptane each were added. The samples were vortexed and centrifuged for 2 min at 524×g. The upper, nonpolar phase of each vial was analyzed using gas chromatography (AOCS Method Ce 1-62 (1993)). Total fatty acid and TAG content were calculated relative to peak area of the internal standard (AOCS Method Ce 1-62 (1993)) and expressed as µg fatty acids (FA)/mg dry weight of sample+/−standard deviation.

TABLE 7

Conversion of TAG to FFA during accelerated aging of whole grain flour

| Line | Lip1 Genotype | Accelerated Aging Time | TAG (µg FA/mg) | FFA (µg FA/mg) |
|---|---|---|---|---|
| Parent Express | Wild-type | Freshly milled | 20.01 +/− 0.08 | 0.2 +/− 0.07 |
| Parent Express | Wild-type | 6 weeks 37° C. | 9.80 +/− 0.05 | 6.71 +/− 0.13 |
| Parent Express | Wild-type | 8 weeks 37° C. | 6.99 +/− 0.91 | 7.31 +/− 1.27 |

The conversion of TAG to FFA due to lipase activity in whole grain flour was analyzed in the wheat variety used for the discovery of mutation alleles. "Parent Express" indicates results from the un-mutagenized parental line. The "Lip1 Genotype" of this variety is "Wild-type" indicating that this material has no induced mutation alleles. As shown in Table 7, there was a high proportion of TAG compared to FFA in freshly milled whole grain flour. After accelerated aging for 6 or 8 weeks at 37° C. (corresponding to approximately 19 or 26 weeks at room temperature), the proportion of TAG decreased and FFA levels increased. The decrease in TAG and increase in FFA over time in whole grain flour is due to lipase activity (Galliard 1986 Hydrolytic and oxidative degradation of lipids during storage of wholemeal flour: Effects of bran and germ components J. Cereal Sci. 4: 179-192).

TABLE 8

Improved shelf-life of whole grain flour from lines with novel alleles of Lip1

| Exp. | Line | Lip1 Genotype | Accelerated Aging Time | TAG (µg FA/mg) | FFA (µg FA/mg) | Percent Improvement |
|---|---|---|---|---|---|---|
| 1 | 1 | Wild-type sibling | 4 weeks 37° C. | 8.16 +/− 0.20 | 5.31 +/− 0.29 | 31% |
| 1 | 1 | Homozygous Mutant | 4 weeks 37° C. | 10.66 +/− 0.46 | 4.15 +/− 0.29 | |
| 2 | 1 | Wild-type sibling | 6 weeks 37° C. | 9.25 +/− 0.41 | 5.67 +/− 0.66 | 17% |
| 2 | 1 | Homozygous Mutant | 6 weeks 37° C. | 10.87 +/− 0.15 | 5.10 +/− 0.12 | |
| 3 | 1 | Wild-type sibling | 8 weeks 37° C. | 5.54 +/− 0.82 | 8.05 +/− 0.49 | 33% |
| 3 | 1 | Homozygous mutant | 8 weeks 37° C. | 7.36 +/− 0.26 | 5.06 +/− 0.64 | |
| 3 | 2 | Wild-type sibling | 8 weeks 37° C. | 4.17 +/− 0.33 | 8.65 +/− 0.67 | 58% |
| 3 | 2 | Homozygous mutant | 8 weeks 37° C. | 6.60 +/− 1.3 | 8.61 +/− 0.98 | |

With regard to Tables 8 and 9, the "Experiment" column indicates materials that were analyzed in the same experiment. The "Line" column corresponds to wheat lines containing the combination of alleles in Table 6. For the Genotype column, "Wild-type sibling" indicates sibling lines resulting from the same crosses as the mutant alleles, but containing the wild-type alleles at the positions indicated in Table 6 for all the genes in the combination. "Homozygous mutant" indicates lines containing homozygous mutant alleles at the positions indicated in Table 6 for all the genes in the combination. For each experiment (Tables 8 and 9), homozygous mutants and wild-type siblings were grown under the same conditions, and grain was milled and aged at 37° C. at the same time prior to analysis.

After accelerated aging for 4 weeks at 37° C. (corresponding to approximately 12.8 weeks at room temperature), Line 1 homozygous for both Lip-A1(W63*) and Lip-D1 (W62*) had higher levels of TAG and lower levels of FFA compared to its wild-type sibling containing wild-type alleles for the Lip1 genes (Table 8, Experiment 1). The percent improvement due to the trait was calculated as the level of TAG retained in the lines with the homozygous alleles compared to their wild-type siblings. In Experiment 1, the improvement in TAG levels was 31%. FFA levels were also reduced. Improvements in TAG levels were also identified in Experiments 2 and 3 for Line 1 and in Experiment 3 for Line 2 (see Table 8).

This data demonstrates that novel alleles in Lip1 improve shelf-life of whole grain flour by reducing the degradation of TAG to FFA.

Methods: Hexanal Analysis

Oxidation of FFA by lipoxygenases produces hydroperoxides that are substrates for additional decomposition into multiple compounds including aldehydes such as hexanal. Hexanal levels produced in a sample can be used as a measure of oxidative rancidity (Fritsch and Gale, Hexanal as a measure of rancidity in low fat foods, *JAOCS* 54:225 (1977)). In order to test shelf-life of whole grain flour derived from grain of novel Lipase 1 mutant alleles, whole grain samples were milled and stored for 8 weeks at 37° C. and analyzed for hexanal levels as described below. Different incubation times and a range of additional milling, moisture, temperature and humidity conditions can also be employed for testing shelf life.

Whole grain flour was milled from mature seeds for 20 seconds at 22 l/s vibration frequency using a MixerMill 300 (Retsch GmbH, Haan, Germany) and stored in closed polyethylene bags. Accelerated aging of flour was conducted in a Percival E30BC8 (Percival Scientific Inc, Perry, Iowa, USA) with the temperature set at 37° C. 10 g samples of flour from 2-4 biological replicates were stored for 4-8 weeks at 37° C. Hexanal levels were analyzed by Medallion Labs (Minneapolis, MN, USA) using a method based on gas chromatography. Units were reported in parts per million (ppm) with a lower detection limit of <0.3 ppm and an upper limit of detection of 50 ppm.

TABLE 9

Reduced hexanal formation in lines with novel alleles of Lip1

| Experiment | Line | Genotype | Accelerated Aging Time | Hexanal (ppm) | Percent Improvement |
|---|---|---|---|---|---|
| 3 | Parent Express | Wild-type | Freshly milled | <0.3 | |
| 3 | Parent Express | Wild-type | 8 weeks 37° C. | 0.83 +/− 0.20 | |
| 3 | 1 | Wild-type sibling | 8 weeks 37° C. | 1.06 +/− 0.20 | 9.4% |
| 3 | 1 | Homozygous mutant | 8 weeks 37° C. | 0.96 +/− 0.06 | |
| 3 | 2 | Wild-type sibling | 8 weeks 37° C. | 0.90 +/− 0.14 | 8.9% |
| 3 | 2 | Homozygous mutant | 8 weeks 37° C. | 0.82 +/− 0.02 | |

As shown in Table 9, hexanal levels were below the limit of detection of <0.3 ppm in freshly milled samples. Hexanal levels increased after 8 weeks at 37° C. demonstrating the progression of oxidative rancidity. Homozygous mutant Lip1 wheat lines and Wild-type sibling controls were compared for hexanal production in whole grain flour stored at 37° C. for 8 weeks. In both wheat lines 1 and 2, hexanal production was reduced by approximately 9% in the Lip1 homozygous mutant lines compared to their sibling controls (see Table 9). This data demonstrates that novel alleles in Lip1 improve shelf-life of whole grain flour by reducing the production of hexanal.

Example 4: Improved Shelf Life by Sensory Characteristics of Lip1 Novel Alleles

Shelf life can be determined by sensory characteristics of the flour and products made from it including color, flavor, texture, aroma, appearance, performance or overall preference of the finished product. Trained panelists can be used to assess differences between materials. For example, Lip1 flour can be stored for various lengths of time, at various temperatures and/or humidities and compared to the wild-type sibling flour and/or parental flour by the panelists for preference in aroma, color, flavor, appearance and texture among other attributes. The flour can also be made into products such as bread, and the crumb and crust compared for in aroma, color, flavor, appearance or texture among other attributes. Bread or other products can also be stored for various lengths of time, at various temperatures and/or humidities and compared to the wild-type sibling flour and/or parental flour by the panelists for preference in in aroma, color, flavor, appearance or texture among other attributes.

Other methods can also be employed to assess sensory characteristics. For example, texture can be measured by a texture analyzer. Color can be measured by a Minolta chroma meter test. Compounds contributing to aroma or taste can be analyzed by liquid or gas chromatography and mass spectrometry.

Example 5: Genome Editing of Lipase 1 in Rice

Mutations in Lipase 1 can also be introduced by genome editing with the CRISPR/Cas or related system. Sequences producing guide RNAs targeting OsLip1 such as the guide sequences listed in Table 10 can be used. Guide RNA can be tested with kits such as GeneArt Precision gRNA Synthesis Kit (ThermoFisher Scientific) for complexing with GeneArt Platinum Cas9 Nuclease (ThermoFisher Scientific) in order to evaluate cleavage efficiency on template DNA prior to use.

TABLE 10

Guide sequences for targeting genome editing of OsLip1

| SEQ ID | Exon | Guide Sequence |
|---|---|---|
| SEQ ID NO: 31 | 3 | ATTTAACAGCTCTTTATACA |
| SEQ ID NO: 32 | 6 | ATTGGATCAAGGACTTGATA |
| SEQ ID NO: 33 | 6 | ACCTTTGCGTTAGGCATGTT |

TABLE 10-continued

Guide sequences for targeting genome editing of OsLip1

| SEQ ID | Exon | Guide Sequence |
|---|---|---|
| SEQ ID NO: 34 | 7 | AGCGAGATCAAGCGCACAGA |
| SEQ ID NO: 35 | 8 | AAGTGGTGGTAAGTTAGATG |

These guide sequences can be cloned into a vector and used for transformation of rice immature embryos using *Agrobacterium tumifaciens* and T-DNA (Hiei et al. (1994) *Plant J.* 6:271). After editing, elimination of the T-DNA can be performed by directly selecting progeny without the T-DNA or by crossing to another plant and selecting progeny without the T-DNA. Alternatively, transformation of rice and other plants can be performed using particle bombardment (Zhang et al. (1998) Mol. Breed. 4:551) with or without selectable markers followed by regeneration of plants. This process can be performed with DNA or RNA (see review by Wolter and Puchta (2017) Genome Biology 18:43).

The above examples are provided to illustrate the invention but not limit its scope. Other variants of the invention will be readily apparent to one of ordinary skill in the art and are encompassed by the appended claims and all their equivalents. The examples above used TILLING technology to create and identify mutations in one or more Lip1 genes of wheat and rice but one of ordinary skill in the art would understand that other methods such as targeted mutagenesis (also known as site-directed mutagenesis, site-specific mutagenesis, oligonucleotide-directed mutagenesis or genome editing) could be used to create the useful mutations disclosed herein in one or more Lip1 loci of a plant (see for example Zhang et al., *PNAS* 107(26):12028-12033, 2010; Saika et al., *Plant Physiology* 156:1269-1277, 2011). All publications, patents, and patent applications cited herein are hereby incorporated by reference.

INFORMATIONAL SEQUENCE LISTING

SEQ ID NO: 1 shows a *Triticum aestivum* gene for Lipase 1, A genome, Lip-A1 exons 1-10 (3,280 base pairs).
ATGGAGCGACGGAGGCGGGTCGCCGTGCTGGCCCTGGTGCTCCTGCTGCTCTCGGCT
TGTCATGGCAGAAGAGGTATGACCTCGATTATCTTTCTTTTTTTTGTTGGGTAACTG
TTCTAAGTTTTCCTCAAATGAATTCCAAGAACGCGTTAACTAATTCAGTAGCGATTG
GGCTGTTTACTGAATTCATTCTGACTGCCATGATTGGAGAAAGCATAGACGAATATC
AGTGCACACGCAGGCATTTCAAAAGGTGTAATCATGCAGGGAGAGAAAGGGGGCA
GCTATGGCACTGACGAAATTGCCCTGCTCCCTGTAAATTTCCCCAAGTTCTGATTGCC
TGTTAGCCGCACACTGGCCTACAACTGAACTAATTGAATGCACTTCTTGTTGTTGTG
GCTGGGGCCTTGGGGGTTGTATCCAAACATCTGGAGAAAGTTGTACCATCTTTGTGT
GGACAGAAAAGGAAATTAGGTGGCTGGCAGTTGGAACCTACCTGGTCCCTTGTTAA
CAAAATGAAGTTCTGGTTGCATATGGTTGGTCACCTCCAGAAAATAAAAGGGTTGA
ATTAAGAAGAACGAGTTGATGAACCGTGGCGGCAAAGAACCATTGTACTGTTGTGG
AGCTTGACTTGCTCTGGGGATTCCACTAGCATCACCCATGATGCCCCCAATTGATCTT
TAGCTGCCATATCTAAGCATTATGTTCAGTGATTCACAGCAAAAGACCATCATAGAT
TCTTTTGGAGCTTGGCTTGACAGATCTAGTGCGTGTACAACATATGGCACTTAACCT
AATACTCCTATTTGATAAGGCCCCCAACTGATTTTGTCTGTCATATACTCATATCACT
GCAATATTTTCAGTTATCCACTTGCTCTAGGTGGATTTGTGATTTGTGAATATAAGTG
GTTTCAGCCTTCAGGACATGAGAATAGGTGAAATTGAATCACCTATGCCCTTTTAAC
TTGGCTGTCACCCGTTCATGCTTAACCTCTCCTGGTAATTAGAACTTAGTTTGTTATA
TCCCTCAGATATTATATGCACAAACTTAATCAAAGTGAAATTCTGCTAAAAGCTGCC
ACAGATATGACAGGCAAAAATCAATTGGGGTCATTTATTCTGTTTGCTTTCAGTTTGT
TCAATTTGTTTTCTTGGCGCAAATGTTTGTCCATCTGCTTTGGCATCTTCTTATATCT
GAAATTGATCTTCTGCACTTGTGTTCAGGATTGCATCATTTATAATATGCTAATAAAC
TAACTGTTTTCATTATCGCAGAGTTCTCTGTCAAGAATCACGATCAGAGTCTTATATA
TGATCATACTCTTGCTAAGACCATTGTGGAGTATGCTTCGGCTGTAAGTTAAACTTAT
GCTCATTATTGCATTAAGTGCATGTCATGCTTTCTAAATGGAGCTTTAGTTCGTCTTT
GTCTTGAGTCTTGTTAAGTCAAAATTAACTAAATACTGTCTGCAGGTGTATATGACA
GATTTAACAGCTTTGTATACATGGACATGCTCAAGATGCAATGACTTGACTCAAGTA
AGAAACCTTGCAACTGTTCTCTTCCATTCATATCTATCTAGGGGTGCTTATTTGTTTT
CCTGAAACTATACTGTTCAAACAGTAAGGGATCTATCAAGATGCTCGCCAATGGTTG
GTTGGGTGTCATATGCAGCTGCCCGACAACTATACAGCTTATAGAATCTGTCCTTTCT

| INFORMATIONAL SEQUENCE LISTING |
|---|
| TATTTATATATTCACCTACTTCTGAAATAGGACTTCGAGATGAGGTCTCTAATTGTTG
ATGTGGAGAACTGCTTGCAGGTTCCTATCTTAACACACTCCATTTTAAGTTGTCATAA
ATTTCCGGCATATTTCTCATCAAGTGTACTGAACTTCTCATGATATGGCCTTCCTTTT
ACCTGCCATTCTACGGGTGAACATGTGACAGGCATTTGTCGGTGTAGCTCACAATC
TAAATGCCATAATAGTTGCAATCAGAGGGACTCAAGAGAACAGGTACTAATCAAAT
TGCATGTGCTTCTAGTATTCCCAGTTAAACCGGTATGCTTTATGTGTTACTATTCTGA
TTTCTTGAGTCACATGTCATTTATGTTTTAGATTTGCTTGCTCAGTGTGCAGAATTGG
ATCAAGGACTTGGTATGGAAGCAGCTTGATCTAAGCTATCCAGACATGCCAAATGC
AAAGGTTATTGCCAATAAACTGTTTATACTTTCTTAAAAGAGAAAAGGAAAGGCAG
ATGCACCTTTTTGCTAAAAGACTTTCTACTACTCTGGTTAAAGGTGCACAGTGGATTT
TTCTCCTCCTATAATAATACAATTTTGCGTCTAGCTATCACAAGTGCTGTGCACAACG
CAAGAAAGACATATGGGGATATCGGTGTCATAGTCACAGGGCACTCAATGGGAGGA
GCCATGGCTGCCTTCTGTGCACTCGATCTTGCTGTAAGTACACAAGATCCAATGTTTC
ACAAATACATTCAATGTCCAGACTCTTAATTCCTTCCAGGTTATATAAATTTCGGTCT
TGTTTCAAATTCCTAACACCAGCACTCTAATATTTGAGGCTTGTTATTATGTAAGCTG
TTGATTTTTCTCTTCAAACCCTATCCACAGATCAAGCTCGGAAGCGACAATGTTCAA
CTCATGACTTTCGGACAGCCTCGTGTTGGCAATGCTGTTTTCGCCTCCTACTTTGCCA
AATATGTACCAAACACAATTCGACTGGTACACGGACATGATATTGTGCCGCATTTGC
CACCTTATTTCTCCTTCCTTTCCAAACTGACGTACCACCACTTCCCAAGAGAGGTACA
CCTTGGGCACAAACTTATAAATATGCTTTCCAACTCCTAGGAAGCCTTTATCGCTGT
GTTATGCTTAGTGCTTGCTCATATTTTAGGTATGGATCGACGAATCTGATGGCAACA
CAACGGAACAGATATGTGATGCCAGCGGCGAAGACCCAAACTGCTGCAGGTTTTTA
CAGAGCACAGACCTCCTGCAGCTCAACTGCCTGTCTCTTTAGCTCCTAGTTCTAACA
TTATCCCCATCTATCGTCTTACTAGGTGCCTCTCCATATTGAGCCTGAGCATTCAGGA
CCATTTCACATACCTGGGAGTAGACATGGAATCAGATGACTGGAGCACCTGCAGAA
TCATCACAGCACAAAGCGTTGAGCGATTACGTAAGCATCTCAGCAGCAACATCATC
ATGACAAAGCACGCCATCGAGGTCTCCATTGTCGAGAATAGCATGCAGACAGACTG
GAGCAGTTCCAGATAG |

SEQ ID NO: 2 shows the Lip-A1 coding sequence of SEQ ID NO: 1
(1,060 base pairs).
ATGGAGCGACGGAGGCGGGTCGCCGTGCTGGCCCTGGTGCTCCTGCTGCTCTCGGCT
TGTCATGGCAGAAGAGGAGTTCTCTGTCAAGAATCACGATCAGAGTCTTATATATGA
TCATACTCTTGCTAAGACCATTGTGGAGTATGCTTCGGCTGTGTATATGACAGATTTA
ACAGCTTTGTATACATGGACATGCTCAAGATGCAATGACTTGACTCAAGACTTCGAG
ATGAGGTCTCTAATTGTTGATGTGGAGAACTGCTTGCAGGCATTTGTCGGTGTAGCT
CACAATCTAAATGCCATAATAGTTGCAATCAGAGGGACTCAAGAGAACAGTGTGCA
GAATTGGATCAAGGACTTGGTATGGAAGCAGCTTGATCTAAGCTATCCAGACATGCC
AAATGCAAAGGTGCACAGTGGATTTTTCTCCTCCTATAATAATACAATTTTGCGTCT
AGCTATCACAAGTGCTGTGCACAACGCAAGAAAGACATATGGGGATATCGGTGTCA
TAGTCACAGGGCACTCAATGGGAGGAGCCATGGCTGCCTTCTGTGCACTCGATCTTG
CTATCAAGCTCGGAAGCGACAATGTTCAACTCATGACTTTCGGACAGCCTCGTGTTG
GCAATGCTGTTTTCGCCTCCTACTTTGCCAAATATGTACCAAACACAATTCGACTGGT
ACACGGACATGATATTGTGCCGCATTTGCCACCTTATTTCTCCTTCCTTTCCAAACTG
ACGTACCACCACTTCCCAAGAGAGGTATGGATCGACGAATCTGATGGCAACACAAC
GGAACAGATATGTGATGCCAGCGGCGAAGACCCAAACTGCTGCAGGTGCCTCTCCA
TATTGAGCCTGAGCATTCAGGACCATTTCACATACCTGGGAGTAGACATGGAATCAG
ATGACTGGAGCACCTGCAGAATCATCACAGCACAAAGCGTTGAGCGATTACGTAAG
CATCTCAGCAGCAACATCATCATGACAAAGCACGCCATCGAGGTCTCCATTGTCGAG
AATAGCATGCAGACAGACTGGAGCAGTTCCAGATAG SEQ ID NO: 3 shows the Lip-A1 protein sequence of SEQ ID NO. 2
(352 amino acids).
MERRRRVAVLALVLLLLSACHGRREFSVKNHDQSLIYDHTLAKTIVEYASAVYMTDLT
ALYTWTCSRCNDLTQDFEMRSLIVDVENCLQAFVGVAHNLNAIIVAIRGTQENSVQNWI
KDLVWKQLDLSYPDMPNAKVHSGFFSSYNNTILRLAITSAVHNARKTYGDIGVIVTGHS
MGGAMAAFCALDLAIKLGSDNVQLMTFGQPRVGNAVFASYFAKYVPNTIRLVHGHDIV
PHLPPYFSFLSKLTYHHFPREVWIDESDGNTTEQICDASGEDPNCCRCLSILSLSIQDHFTY
LGVDMESDDWSTCRIITAQSVERLRKHLSSNIIMTKHAIEVSIVENSMQTDWSSSR SEQ ID NO: 4 shows a *Triticum aestivum* gene for Lipase 1, D genome,
Lip-D1 exons 1-10 (3,263 base pairs).
ATGGAGCGACGGAGGCGGGTCGCTGTGCTGGCCCTGGTGCTCCTGCTGCTCTCGGCT
TGTCATGGAAGAAGAGGTATGACCTCGATTATCTTTCTTTTTTTGTTGGGTAACTGT
TCTAAGTTTTCCTCAAATGAATTCCAAGAACGTGTTAACTAATTCAGTAGCGATCGG
GCTGTTTACTGAGTTCATTCTGACTGCCATGATTGAAGCAAGCATAGATGAATATCA
GTGCATACGCAGGCATTTCAAAAGGTGTAATCATGCAGGGAGAGAAAGGGGGCAGC
TGTGGCACTGACGAAATTGCCCTGCTCCCTGTAAATTTCGCCGAGTTCTGATTGCCTG
TTAGCAGCACACTGGCCAACAACTGAACTAATTGAATGCACTTCTTGTTGTGGCTGG
GGCCTTGGGGGTTGTATCCAAACATCTGGAAAAGTTGTACTATCTTTGTGTGGACA
GAAAAGGAAATTAGGTGGCCGACAGTTGGAACTTACCTGGTGCCTTGTTAACAAAA
TGGAGTTCTGGTTGCATATTGGTTGGTCATCTCTAGAAAATAAAAGGGTTGAATTAA
GAAGAACAGATTGATGATGAACCGTGGCAGCAAACAACCATTGTACTGTTGTGGAG
CTTGACTTGCTCTGGGGACTCTACTAGCATCATCCACGATGCCCCCAATTGATCTTTA
GCTGCCATATCTAAGCATTATTTTCAGTGATTCACAGCAAAAGACCATCATAGATTC
TTTTGGAGCTTGGCTTGACAGATCTAGTGCGTTTACAGCATATGGCACTTAACCTAG
TACTCCTATTTGATAAGCCCCCCACCTGATTTCTGTCTGTCATGTACTCATATCGTTG

```
CAATATTTTCAGTTATCCACTTGCTCTAGGTGGATTCTGTGATTTGTGAATATAAGTG
GTTTCAGAGAATAGGTGAAATTGAATCATCTATGCCCTTTTAACTTGGCTGTCACCC
GTTCATGCTTAACCTCTCCTGGTAATTAGAACTTACTTTTGTTCTATCCCTCAGATAT
TATATGCACAAACTGAATCAAAGCGAACTTGTGCTAGAAGCTGCCACAGATATGAC
AGGCAAAAATCAATTGGGGTCATTTATTCTGTTTGCTTTCATTTTGTTCAATTTGTCT
TTCTTGGCGTAAATGTTTGTCCATCTGCTTTGGCATCTTCTTATGTCTGAAATTGATCT
TCTGCACTTGTGCTCAAGATGGCATCATTTAATATGCTAGTAAACTAACTGTTTTCAT
TGTCGCAGAGTTCTCTGTCAATCAGGATCAGAGTCTTATATATGATCATACTCTTGCT
AAGACCATCGTGGAATATGCTTCGGCTGTAAGTTAAACTTATGCTCATTATTCCATT
AAATGCATGTCATGCTTTCTAAATGGAGCTTTAGTTCGTCTTTATCTAGAATCTTGTT
AAGTCAAATTAACTAAATACTGTCTGCAGGTGTATATGACAGATTTAACAGCTTTGT
ATACATGGACATGCTCAAGATGCAATGACTTGACTCAAGTAAGAAACCTTCCAACTG
TTCTCTTCCATTCATATCTATCTAGGGGTGCTTATTTGTTTTCCTGAAATTACAACTGT
CAAACAGTAAGGGATCTATCAAGATGCTCGCAATGTTGGTTGGGTGTCATATGCA
GCAGCCGTCAACTATACAGCTTATAGAATCTGTCCTTTCTTTATTTATACATTCACCT
ACTTCTGAAATAGGACTTCGAGATGAGGTCTCTAATTGTTGATGTGGAGAACTGCTT
GCAGGTTCCTATCTTAACACACTCCATTTTAAGTTGTCATAAATTTCCGGCATATTTC
TTATCAAGTGTACTAAACTTTTCATGATATGGCCTTCCTTTTACCTGCCATTCTACGG
GTGAACAATGTGACAGGCATTTGTCGGTGTAGCTCACAATCTAAATGCCATAATAGT
TGCAATCAGAGGGACTCAAGAGAACAGGTACTAATAAAATTGCATGTGCTTCTAGT
ATTCCCAGTTAAACCGGTATGCTTTATGTGTTACTATTCTGATTTCTTGAGTTACATG
TCATTTATGTTTTAGATTTGCTTGCTCAGTGTGCAGAATTGGATCAAGGACTTGGTAT
GGAAGCAGCTTGATCTAAGCTATCCAGACATGCCAAATGCAAAGGTTATTGCCAAT
AAACTGTTTATACTTTCTTAAAAGAGAAAAGGAAAGGCAGATGCACGTTTTGCTAAA
AGACTTTCTACTACTCTGGTTAAAGGTGCACAGTGGATTTTTCTCCTCCTATAATAAT
ACAATTTTGCGTCTAGCTATCACAAGTGCTGTGCACAAGGCAAGAAAGACATATGG
GGATATCGGCGTCATAGTCACAGGGCACTCAATGGGAGGAGCCATGGCTGCCTTCT
GTGCACTCGATCTTGCTGTAAGTACACAAGATCCAATGTTTCACAAATACATTCAAT
GTCCAGACTCTTAATTCCTTCCAGGTTATAAAGTGCGGTCTTGCATCATATTCCTAAC
ACCAGCACTCTAATAATTGAGGCTTGTTATTATGTAAGCTGTTGATTTTTCTCTTCAA
ACCCTATCCACAGATCAAGCTCGGAAGCGACAATGTTCAACTCATGACTTTCGGACA
GCCTCGTGTTGGCAATGCTGTTTTCGCCTCCTACTTTGCCAAATATGTGCCAAACACA
ATTCGACTGGTACACGGACATGATATCGTGCCGCATTTGCCACCTTATTTCTCCTTTC
TTTCCAAACTGACGTACCACCACTTCCCAAGAGAGGTATACCTTGGGCACAAACGTA
TAATTACGCTTTCTTGGATATCAACTCAGTCCCTGGGCTTCATCTCTGTGCTATGCTT
ATTCCGCCCAAATTTCAGGTATGGATCGATGATTCTGACGACAACACAACCGAACAG
ATTTGTGATGCCAGCGGCGAAGACCCAAACTGCTGCAGGTTTTACAGCTCAGACCTT
CCTTGCAGTTCAATTGCCTGTCTCTTCTCCTAATTCTAACATTTCCCCACTGATCATTT
TACTAGGTGCCTCTCCATACTGAGTTTGAGCATTCAGGACCATTTCACATACCTGGG
AGTCGATATGGAATCAGATGACTGGAGCACCTGCAGAATCATCACAGCACAAAGTG
TTGAGCGACTACGGAAGGATCTCGCCAGCAACATCATCATGACAAAGCACGGCGTC
GAGGTCTCCATTGTCGAGAATAGCGTGCAGACAGACTGGAGCAGTTCCATATAG
```

SEQ ID NO: 5 shows the Lip-D1 coding sequence of SEQ ID NO. 4 (1,056 base pairs).

```
ATGGAGCGACGGAGGCGGGTCGCTGTGCTGGCCCTGGTGCTCCTGCTGCTCTCGGCT
TGTCATGGAAGAAGAGAGTTCTCTGTCAATCAGGATCAGAGTCTTATATATGATCAT
ACTCTTGCTAAGACCATCGTGGAATATGCTTCGGCTGTGTATATGACAGATTTAACA
GCTTTGTATACATGGACATGCTCAAGATGCAATGACTTGACTCAAGACTTCGAGATG
AGGTCTCTAATTGTTGATGTGGAGAACTGCTTGCAGGCATTTGTCGGTGTAGCTCAC
AATCTAAATGCCATAATAGTTGCAATCAGAGGGACTCAAGAGAACAGTGTGCAGAA
TTGGATCAAGGACTTGGTATGGAAGCAGCTTGATCTAAGCTATCCAGACATGCCAAA
TGCAAAGGTGCACAGTGGATTTTTCTCCTCCTATAATAATACAATTTTGCGTCTAGCT
ATCACAAGTGCTGTGCACAAGGCAAGAAAGACATATGGGGATATCGGCGTCATAGT
CACAGGGCACTCAATGGGAGGAGCCATGGCTGCCTTCTGTGCACTCGATCTTGCTAT
CAAGCTCGGAAGCGACAATGTTCAACTCATGACTTTCGGACAGCCTCGTGTTGGCAA
TGCTGTTTTCGCCTCCTACTTTGCCAAATATGTGCCAAACACAATTCGACTGGTACAC
GGACATGATATCGTGCCGCATTTGCCACCTTATTTCTCCTTTCTTTCCAAACTGACGT
ACCACCACTTCCCAAGAGAGGTATGGATCGATGATTCTGACGACAACACAACCGAA
CAGATTTGTGATGCCAGCGGCGAAGACCCAAACTGCTGCAGGTGCCTCTCCATACTG
AGTTTGAGCATTCAGGACCATTTCACATACCTGGGAGTCGATATGGAATCAGATGAC
TGGAGCACCTGCAGAATCATCACAGCACAAAGTGTTGAGCGACTACGGAAGGATCT
CGCCAGCAACATCATCATGACAAAGCACGGCGTCGAGGTCTCCATTGTCGAGAATA
GCGTGCAGACAGACTGGAGCAGTTCCATATAG
```

SEQ ID NO: 6 shows the Lip-A1 protein sequence of SEQ ID NO. 5 (351 amino acids).

```
MERRRRVAVLALVLLLLSACHGRREFSVNQDQSLIYDHTLAKTIVEYASAVYMTDLTA
LYTWTCSRCNDLTQDFEMRSLIVDVENCLQAFVGVAHNLNAIIVAIRGTQENSVQNWIK
DLVWKQLDLSYPDMPNAKVHSGFFSSYNNTILRLAITSAVHKARKTYGDIGVIVTGHSM
GGAMAAFCALDLAIKLGSDNVQLMTFGQPRVGNAVFASYFAKYVPNTIRLVHGHDIVP
HLPPYFSFLSKLTYHHPPREVWIDDSDDNTTEQICDASGEDPNCCRCLSILSLSIQDHFTY
LGVDMESDDWSTCRIITAQSVERLRKDLASNIIMTKHGVEVSIVENSVQTDWSSSI
```

-continued

INFORMATIONAL SEQUENCE LISTING

SEQ ID NO: 7 shows a *Triticum aestivum* gene for Lipase 1, B genome (3,460 base pairs).
ATGGGGAGGTGGAGGCGGGCCGGCGTGCTGGCTCTGGTGCTCCTGCTGCTCTCCGCT
TGCCATGGAAGACGAGgtatggtatggttaccttttctttccttttttcttgcgaaacatagtaagtagaacatatcacaaacgtg
cttcggttaccaattttgatgcttgcttgttgggtgactgttctaagttttcctcaaatgaatttccaagaacgtgttagctaattcagtagcgatcg
ggctgtttactgaattcattctgactgccataattagagaaagcataagatgaatgtcagtgcatacgcaggcttttcaaaaggtgtaatcatgc
agggagaggaaggggggcagctgtggcagactgacgaaattgccctgctccctgtaaatttcgccaagttctgattgctgttagccgcgca
ctggccaacaactcaactaattgaatgcgcttcttgttgttgtggctggggccttggggggttgtatccaaacatctggaaaaagttgtactatctt
tgtgtggacagaaaaggaaattaggtggctgacagttggaacatacctggtgccttgttaacataacgaagttctggttgcatatggttggtca
cctccagaaaatagaagtgttgaattaagaagaacgagtcgatgaaccgtggcaggcaaacagccattatactgttgtggagcttgacttgct
ctggggattctactagcatcatccatgatgccccaattgatctttagctgccatatctaagcattattttcagtgattcacagcaaaagaccatc
ataacttatttggagcttggcttgacagatctagtgcgtttacaacatatggcacttaacctaactcctatttgataaggccccaactgatttc
tgtctgtcatatactcatatcattgcaatattttcagttatccacttgctcaggtggattctgtgatttgtgaatataagtggtttcagccttcaggac
atgagaataggtgaaattgaatcatctatgccatttaacttggctgtcacccgttcatgataacctctcctggtaattagaacttacttttgttctat
acacaaacttaatcaaagtgaacttgtgctaaaagctgccacagatatgacaggcaaaaatcaattgggtcatttattctgtttgctttcagttt
gttcaatttgtttttcttggcataaatgtttgtccatctgctttggcatcttcttatatctgaaattgatcttctgaaattgatcttctgcacttgtgttattgcatcatttaatatg
ctaataaactaactgttttcattatcgcagAGTTCTCTGTCAAGAATCACGGTCAGAGTCTTATATATGA
TCATACTCTTGCTAAGACCATCGTGGAGTATGCTTCGGCTgtaagtttaacttatgctcattattgcattaa
atgcatgtcatgattctaaatagagattagtttgtattgtatgaatcttgttaagtcaaattaactaaatactgtctgcagGTGTATATG
ACAGATTTAACAGCTTTGTATACATGGACATGCTCAAGATGCAATGACTTGACTCAA
gtaagaaaccgtccaactgttctcttccattcatatctactccctccgtcccaaaattattgtcttaaatttgtctagatacggatgtacctaatacta
aaacgtgacttgatacatccgtatttagacaaatctaagacaagaatttgggacggagggagtatctaggggtgatatttgttttcctgaaatt
ataactgttcaaacagtaagggatctatcaagatgctcgccaatggttggttaggtgtcatatgcagcagcccgtcaactatacagcttataga
atctgtcatttctttatttatacattcacctacttctgaaatagACTTCGAGATGAGGTCTCTAATTGTTGATGTG
GAGAACTGCTTGCAGgttcctatcttaacacactccattttaagttgtcataaatttccggcatatttcttatcaagtgtactgaacat
ctcatgatatggccttccttttacctgccattctacgggtgaacaatgtgacagGCATTTGTCGGTGTAGCTCACAATC
TAAATTCCATAATAGTTGCAATCAGAGGAACTCAAGAGAACAGgtactaatcaaattgcatgtgct
tctagtattcccagttaaaccggtatgcttttatgtgttactattccgatttcttgagtcacatgtcatttatgttttagatttgcttgctcagTGTGC
AGAATTGGATCAAGGACTTGGTATGGAAGCAGCTTGATCTAAGCTATCCAGACATG
CCAAATGCAAAGgttattgccaataaactgtttatactttcttaaaagagaaaaggaaaggcagatgcacctttttgctaaaagactt
tctactactctggttaaagGTGCACAGTGGATTTTTCTCCTCCTATAATAATACAATTTTGCGTCT
AGCTATCACAAGTGATGTGCAACGCAAGAAAGACATATGGGGATATTGGTGTCA
TAGTCACAGGGCACTCAATGGGAGGAGCCATGGCTGCCTTCTGTGCACTCGATCTTG
CTgtaagtacacaagatccaatgttttcacaaatacattcaatgtccagactcttaattcctcccaggttataaattgcggtatgtatcaaattcct
aacaccagcactctaatatttgaggcttgttattatgtaagctgttgattttctcttcaaaccctatccacagATCAAGCTCGGAAG
CGACAATGTTCAACTCATGACTTTCGGACAGCCTCGTGTCGGCAATGCTGTTTTCGC
CTCCTACTTTGCCAAATATGTACCAAACACAATTCGACTGGTACACGGACATGATAT
TGTGCCGCATTTGCCACCTTATTTCTCCTTTCTTTCCAAACTGACGTACCACCACTTC
CCAAGAGAGgtatacctgggcacaaacttataaatatgattccaactcctaggaagcctttatcgctgtgttatgcttagtgcttgctc
atattttagGTATGGATCAACGAATCTGATGGCAACACAACGGAACAGATATGTGATGCC
AGCGGCGAAGACCCAAACTGCTGCAGgtttttacagagcacagaccttccttgcggctcaactgatgtctctttagc
tcctagttctgacattatcccatcgatcgttttactagGTGCCTCTCCATATTGAGCCTGAGCATTCAGGACC
ATTTCACATACCTGGGAGTAGACATGGAATCAGATGACTGGAGCACCTGCAGAATC
ATCACAGCACAAAGCGTTGAGCGATTACGTAAGGATCTCGGCAGCAACATCATCAT
GACAAAGCACGGCGTCGAGGTCTCCATTGTCGAGAATAGCATGCAGACAGACTGGA
GCAGTTCCAGATAG SEQ ID NO: 8 shows the Lip-B1 coding sequence of SEQ ID NO. 4
(1,059 base pairs).
ATGGGGAGGTGGAGGCGGGCCGGCGTGCTGGCTCTGGTGCTCCTGCTGCTCTCCGCT
TGCCATGGAAGACGAGAGTTCTCTGTCAAGAATCACGGTCAGAGTCTTATATATGAT
CATACTCTTGCTAAGACCATCGTGGAGTATGCTTCGGCTGTGTATATGACAGATTTA
ACAGCTTTGTATACATGGACATGCTCAAGATGCAATGACTTGACTCAAGACTTCGAG
ATGAGGTCTCTAATTGTTGATGTGGAGAACTGCTTGCAGGCATTTGTCGGTGTAGCT
CACAATCTAAATTCCATAATAGTTGCAATCAGAGGAACTCAAGAGAACAGTGTGCA
GAATTGGATCAAGGACTTGGTATGGAAGCAGCTTGATCTAAGCTATCCAGACATGCC
AAATGCAAAGGTGCACAGTGGATTTTTCTCCTCCTATAATAATACAATTTTGCGTCT
AGCTATCACAAGTGATGTGCAACGCAAGAAAGACATATGGGGATATTGGTGTCA
TAGTCACAGGGCACTCAATGGGAGGAGCCATGGCTGCCTTCTGTGCACTCGATCTTG
CTATCAAGCTCGGAAGCGACAATGTTCAACTCATGACTTTCGGACAGCCTCGTGTCG
GCAATGCTGTTTTCGCCTCCTACTTTGCCAAATATGTACCAAACACAATTCGACTGGT
ACACGGACATGATATTGTGCCGCATTTGCCACCTTATTTCTCCTTTCTTTCCAAACTG
ACGTACCACCACTTCCCAAGAGAGGTATGGATCAACGAATCTGATGGCAACACAAC
GGAACAGATATGTGATGCCAGCGGCGAAGACCCAAACTGCTGCAGGTGCCTCTCCA
TATTGAGCCTGAGCATTCAGGACCATTTCACATACCTGGGAGTAGACATGGAATCAG
ATGACTGGAGCACCTGCAGAATCATCACAGCACAAAGCGTTGAGCGATTACGTAAG
GATCTCGGCAGCAACATCATCATGACAAAGCACGGCGTCGAGGTCTCCATTGTCGA
GAATAGCATGCAGACAGACTGGAGCAGTTCCAGATAG SEQ ID NO: 9 shows the Lip-B1 protein sequence of SEQ ID NO. 5
(353 amino acids).
MGRWRRAGVLALVLLLLSACHGRREFSVKNHGQSLIYDHTLAKTIVEYASAVYMTDLT
ALYTWTCSRCNDLTQDFEMRSLIVDVENCLQAFVGVAHNLNSIIVAIRGTQENSVQNWI
KDLVWKQLDLSYPDMPNAKVHSGFFSSYNNTILRLAITSDVHNARKTYGDIGVIVTGHS
MGGAMAAFCALDLAIKLGSDNVQLMTFGQPRVGNAVFASYFAKYVPNTIRLVHGHDIV
PHLPPYFSFLSKLTYHHFPREVWINESDGNTTEQICDASGEDPNCCRCLSILSLSIQDHFTY
LGVDMESDDWSTCRIITAQSVERLRKDLGSNIIMTKHGVEVSIVENSMQTDWSSSR

| INFORMATIONAL SEQUENCE LISTING | | | |
|---|---|---|---|
| SEQ ID NO: 10 | Ta_Lip1_A_L2 | | GAAATTGATCTTCTGCACTTGTGTTCAGGA |
| SEQ ID NO: 11 | Ta_Lip1_A_R1 | | TGGGGATAATGTTAGAACTAGGAGCTA |
| SEQ ID NO: 12 | Ta_Lip1_DB_L1 | | GACAGGCAAAAATCAATTGGGGTCATTT |
| SEQ ID NO: 13 | Ta_Lip1_D_R3 | | TGATCAGTGGGGAAATGTTAGAATTAGGAGA |
| SEQ ID NO: 14 | Ta_Lip1_B_L1 | | CTGAAATTGATCTTCTGCACTTGTGTTATTGCA |
| SEQ ID NO: 15 | Ta_Lip1_B_R1 | | AGCATAACACAGCGATAAAGGCTTCCTAGG |
| SEQ ID NO: 16 | Ta_Lip1_B_Lmarker | | TCTCTGTCAAGAATCACGGTC |
| SEQ ID NO: 17 | Ta_Lip1_B_Rmarker | | GCTGCTGCATATGACACCTA |
| SEQ ID NO: 18 | Ta_Lip1_L1 | | CACAGTGGATTTTTCTCCTCCT |
| SEQ ID NO: 19 | Ta_Lip1_R1 | | CCGATATCCCCATATGTCTTTC |
| SEQ ID NO: 20 | Ta_Lip2_L1 | | GACCCAGTTTCAACAGCAAC |
| SEQ ID NO: 21 | Ta_Lip2_R1 | | CGGACCTAACAGCTCTATATA |
| SEQ ID NO: 22 | Ta_Lip3_L3 | | CACTTGATCTTGTTGTGAACTAC |
| SEQ ID NO: 23 | Ta_Lip3_R3 | | GCGTGAGGCAAGTATCTCTT |
| SEQ ID NO: 24 | Ta_GAPD_F | | TGTCCATGCCATGACTGCAA |
| SEQ ID NO: 25 | Ta_GAPD_R | | CCAGTGCTGCTTGGAATGATG |

SEQ ID NO: 26 shows an *Orzya sativa* gene for Lipase 1, OsLip1 exons 1-10 (3672 base pairs).
ATGATGGGAGGTTGGTTTGGATGTGTCTGTAGGTTCATGGAGAGGTGGAGATGCGTC
AGTGTGTTGGCTCTGGTGCTCTTGCTGTCAAATGCTTCCCATGGGAGAGGTAGTTTC
ATGTGACCCTTTGCCCTAAGTTTCCAATTTTGATGCTTGTTGGGTAATTGTTCTAAGT
TTGCCTCAATGTATTCCAAAATGGGTTAACGTTTAACAGAACAAATAGCAAATCAAG
GTATTAGTAACTGACTGCTTTGGTGGGAGAAAGCAGACCAATGCTTATGCAGGCATC
TGTAATAAGGTTTAATTTTCTAGAGAAATGGGGAGTGCTGATGATGGATGAGATTGT
CTTGTTCTTTTGATTTTACCAAGTTCTGGGTTTTGGCTGTCGGTTTGGTATGAAATGA
CCAGTAATTTACTGGAGTTACTGGACTAGTTGACCAAGTTATAGCTGTTCTGCTGTTG
TAATTGGGGATGCATGAGCAAGAGTAGGTGGGTGACAGTTGGAATTTCTTGCTGCCC
TGTCCTTACTAATATAATTGATGCCCTAATTGCTGAAAAGGAAGACAAGGTTGGTGG
GTGAGTAGAAAATAACAACATTGGAAATAAAGAAGTTGATGGCAAGAAAGATAAT
GGATATAATTGTGCTCAGAGATTCCTATTATTCCAAACACATATTTGAACCTTAAAC
CTAATATTTATTGAGTTCTCAACTTCTTTCTTGCTTCCTTAAACTTGAATTCCACTTCA
TTACAGCTTGTGGATTCTTTGCATTCATAAAACTTTGTCTCAGGATCCTGAAATATGT
GAAGTTCAAACATTTATAGAGTATTCTTTAGTTTGGCCTTCACCAATGCAAGCTTGA
CACTCTGTTGGTGAAAGTTTATTTAGTACTGCTATATGCTGCATGCCATCTGCCATAT
ATTATATACACAACTTGATCGAGCATTTTTTCTGCACCACCTACTCCGATTGGGCTTA
ATTTCACAAGAAGATTTAGCTAGCAGTTAGCACAATTTTTGGGGCATTAATAGTTAC
TCGTCACATGGAACTGCTGATTTGAGGTTTAAGATTGAGCTTGAAGCTACCACAAGT
TTACCAGGCCAGAACGTGATACTGGGGCCACTTTTCCTATAAGTTTGATGCCATAAA
AATTGAGAATATGAAATCAGCTTTCGGCTTTCCTTCACTTATGAGCAAATGGGGCTT
AAATATCTTAAGCATGTCCAAACAAGTCAAATGTCCTTAATCAATTTTCTTTTCATTTG
TCAACATTTGATTTTATTACCGAATATAATGTCGGTTCGTCTGCTGCATACCTTCGTA
TAGTAGATGTAGTTGATCATCAATGTTTGTATTCATGCTCTCATCATCAAAAACTGG
AGTGAACTAACTTTTTTCATTATAACAGATATCTCTGTCCAGCACTCTCAGCAAACTT
TGAACTATAGCCATACTCTTGCCATGACTCTTGTGGAATATGCTTCTGCTGTAAGAA
ACTTTTCCTTATTTTTACATAAGCAGTATGTGTTCTAGGTAACATTTCTGTTCATGTTT
TGCATTTCACAAAGGCAACTGTCTCTCTTTCTTGTTTTCTCCTTTTGCCCCAAAATAA
AATCAGCTACTTTAAAAATGAAAAAAGAAGAAGAACTTAGCTGATGGCTCTTC
GTTTTCTCCAGGTGTACATGACAGATTTAACAGCTCTTTATACATGGACGTGCTCAA
GGTGTAATGACTTGACTCAAGTAAGAAGCCTTCAAGTTTGTTCTGTTCAATTCATATT
TAGAGGGATACTCATTAACTGCGAAGTAAAGCTTATATTGTTACTGATGGTTGGGGG
CAGAATCACCTCAAATGTCCGCTTGTCAGGATCTGCCATTCCTCTTAATGAATCATA
AAAGCATTTCCTTTTCTTCTTCTTTAGGAAAATATTTCTTTTGTCATGGACAGGAT
AAATTTGTTGCTAGTTTTGATATGACTACATTTGAAATAGGGCTTTGAGATGAAATC
TCTAATCGTGGATGTGGAGAACTGCCTACAGGTTCTTATCTTACAAATTTCAAACTA
ATATCATAAAATTCTCGATGATATTTGAGTACATTAAGCGTTTAATGATTTTATTTATA

| INFORMATIONAL SEQUENCE LISTING |
|---|
| TTGTGTGACACTATGTGGGTGAACAATGTAACAGGCATTCGTTGGTGTGGATTATAA
TTTAAATTCAATAATTGTTGCAATAAGAGGGACTCAAGAAAACAGGTACACTGATTT
TGCACAGTGTGTTACTGTTCCCTGTTCCCATGTGATTTATATCTTGATTTGCTTACTCA
GTATGCAGAATTGGATCAAGGACTTGATATGGAAACAACTTGATCTGAGCTATCCTA
ACATGCCTAACGCAAAGGTTATTATCGCTAGCAAAGTGTTTCTATCTCCTTAAGTCCT
TTTATTAAAAGAAGATCAGTGCCTTTTTTTTCCCCTAAAATATCTCCACTTCTCTGTTT
AAAGGTGCACAGTGGATTTTTCTCCTCCTATAATAACACGATTTTACGTCTAGCATC
ACAAGTGCTGTCCACAAGGCAAGACAGTCATATGGAGATATCAATGTCATAGTTAC
AGGGCACTCAATGGGAGGAGCCATGGCATCCTTCTGTGCGCTTGATCTCGCTGTAAG
TACCCCCGAGGCTCAAAGTTTTACTAATACATCCAGTGTTCAGATTACAGACTCTTCT
AAGACATTATAGATGTAATATCTGTATCACATTCTTTCCATAAAAAAATTGAATGCC
ATCATTGGTTGTTATGTAAACTGATACAGTCTTGTTCTTTTACTCTGTCCACAGATCA
ATCTTGGAAGCAATAGTGTTCAACTCATGACTTTCGGACAGCCTCGTGTTGGCAATG
CTGCTTTTGCCTCTTATTTTGCCAAATATGTGCCCAACACGATTCGAGTCACACATGG
ACATGATATTGTGCCACATTTGCCCCCTTATTTCTCCTTTCTTCCCCATCTAACTTACC
ACCACTTCCCAAGAGAGGTATGCCTCACAGGCTTGCACATAAGCTAATTAAGAATGC
GCTCTTGTACACTTAACTTGGCCCTGGCTTTATCTATTTTATCACTATAGCACACTTT
ATGAATTTTTGTATTAACACCCTTTTTATATTTACCATTAATAATACAAAATCAATGC
CTAGTGCAGCAAGTTGTTAGATGCTCTGCACACCTTCCATGGGACAATGATACTAAT
CTAAATCAAATATGCTAATATTCTTTAGAGATGTGGTGTTACATCCTGTACAGTGTA
CACACATAATATGCTTGTTCGAATTTCAGGTATGGGTCAATGATTCTGAGGGCGACA
TAACCGAACAGATATGTGATGATAGTGGTGAAGATCCAAATTGCTGCAGGTTTAGA
GGCTCATTTTAACAACCTAACAACTCAAATCTGGTTTTTTAGCTTCTAATTATAATT
TCTGTTCCCTCGTTTATTTCCTAGGTGCATCTCCACATGGAGTTTGAGCGTTCAAGAC
CATTTCACATACCTGGGAGTTGATATGGAAGCTGACGACTGGAGCACTTGTAGAATC
ATCACAGCTGAAAATGTTAGGCAACTCCAAAAGGATCTCGCCAGCAACATCATCGT
CTCCAAGCACTCTGTCGATGTCACTATTGTAGAACCTAGTTCACAAACATATTGA

SEQ ID NO: 27 shows the OsLip1 coding sequence of SEQ ID NO: 26
(1,077 base pairs).
ATGATGGGAGGTTGGTTTGGATGTGTCTGTAGGTTCATGGAGAGGTGGAGATGCGTC
AGTGTGTTGGCTCTGGTGCTCTTGCTGTCAAATGCTTCCCATGGGAGAGATATCTCTG
TCCAGCACTCTCAGCAAACTTTGAACTATAGCCATACTCTTGCCATGACTCTTGTGG
AATATGCTTCTGCTGTGTACATGACAGATTTAACAGCTCTTTATACATGGACGTGCTC
AAGGTGTAATGACTTGACTCAAGGCTTTGAGATGAAATCTCTAATCGTGGATGTGGA
GAACTGCCTACAGGCATTCGTTGGTGTGGATTATAATTTAAATTCAATAATTGTTGC
AATAAGAGGAACTCAAGAAAACAGTATGCAGAATTGGATCAAGGACTTGATATGGA
AACAACTTGATCTGAGCTATCCTAACATGCCTAACGCAAAGGTGCACAGTGGATTTT
TCTCCTCCTATAATAACACGATTTTACGTCTAGCTATCACAAGTGCTGTCCACAAGG
CAAGACAGTCATATGGAGATATCAATGTCATAGTTACAGGGCACTCAATGGGAGGA
GCCATGGCATCCTTCTGTGCGCTTGATCTCGCTATCAATCTTGGAAGCAATAGTGTTC
AACTCATGACTTTCGGACAGCCTCGTGTTGGCAATGCTGCTTTTGCCTCTTATTTTGC
CAAATATGTGCCCAACACGATTCGAGTCACACATGGACATGATATTGTGCCACATTT
GCCCCCTTATTTCTCCTTTCTTCCCCATCTAACTTACCACCACTTCCCAAGAGAGGTA
TGGGTCAATGATTCTGAGGGCGACATAACCGAACAGATATGTGATGATAGTGGTGA
AGATCCAAATTGCTGCAGGTGCATCTCCACATGGAGTTTGAGCGTTCAAGACCATTT
CACATACCTGGGAGTTGATATGGAAGCTGACGACTGGAGCACTTGTAGAATCATCA
CAGCTGAAAATGTTAGGCAACTCCAAAAGGATCTCGCCAGCAACATCATCGTCTCC
AAGCACTCTGTCGATGTCACTATTGTAGAACCTAGTTCACAAACATATTGA SEQ ID NO: 28 shows the OsLip1 protein sequence of SEQ ID NO: 26 (358 amino acids).
MMGGWFGCVCRFMERWRCVSVLALVLLLSNASHGRDISVQHSQQTLNYSHTLAMTLV
EYASAVYMTDLTALYTWTCSRCNDLTQGFEMKSL1VDVENCLQAFVGVDYNLNSIIVAI
RGTQENSMQNWIKDLIWQLDLSYPNMPNAKVHSGFFSSYNNTILRLAITSAVHKARQS
YGDINVIVTGHSMGGAMASFCALDLAINLGSNSVQLMTFGQPRVGNAAFASYFAKYVP
NTIRVTHGHDIVPHLPPYFSFLPHLTYFIHFPREVWVNDSEGDITEQICDDSGEDPNCCRCI
STWSLSVQDHFTYLGVDMEADDWSTCRIITAENVRQLQKDLASNIIVSKHSVDVTIVEPS
SQTY |

| SEQ ID NO: 29 | OsLip1_L2 | CACCTACTCCGATTGGGCTTAATTTCACA |
|---|---|---|
| SEQ ID NO: 30 | OsLip1_R8 | GAACAAGACTGTATCAGTTTACATAACAACCA
ATG |

| SEQ ID | Exon | Guide Sequence |
|---|---|---|
| SEQ ID NO: 31 | 3 | ATTTAACAGCTCTTTATACA |
| SEQ ID NO: 32 | 6 | ATTGGATCAAGGACTTGATA |
| SEQ ID NO: 33 | 6 | ACCTTTGCGTTAGGCATGTT |
| SEQ ID NO: 34 | 7 | AGCGAGATCAAGCGCACAGA |
| SEQ ID NO: 35 | 8 | AAGTGGTGGTAAGTTAGATG |

What may be claimed is:

1. Wheat flour comprising an A genome and a D genome and one or more human induced mutations in a Lipase 1 gene in the A genome (Lip-A1) and one or more human induced mutations in a Lipase 1 gene in the D genome (Lip-D1), wherein the one or more human induced mutations in the Lip-A1 and Lip-D1 genes are homozygous and reduce Lipase 1 activity as compared to Lipase 1 activity from wild type Lip-A1 and Lip-D1 genes, and wherein the flour comprises a characteristic selected from the group consisting of: (a) increased hydrolytic stability as measured by reduction in the rate of conversion of mono-, di- or tri-acylglycerides (TAG) to free fatty acids (FFA) as compared to flour from grain of a wild type wheat plant; (b) increased oxidative stability as measured by a reduction in degradation by available oxygen as compared to flour from grain of a wild type wheat plant; (c) at least a 10% reduction in conversion of mono-, di- or tri-acylglycerides (TAG) to free fatty acids (FFA) as compared to flour from grain of a wild type wheat plant; (d) at least a 5% reduction in hexanal production as compared to flour from grain of a wild type wheat plant; and (e) combinations thereof.

2. The wheat flour of claim 1, wherein the flour has at least a 10% reduction in the conversion of mono-, di- or triacylglycerides (TAG) to free fatty acids (FFA) as compared to flour from grain of a wild type wheat plant.

3. The wheat flour of claim 1, wherein the flour has increased hydrolytic stability as measured by reduction in the rate of conversion of mono-, di- or tri-acylglycerides (TAG) to free fatty acids (FFA) as compared to flour from grain of a wild type wheat plant.

4. The wheat flour of claim 1, wherein the flour has increased oxidative stability as measured by a reduction in degradation by available oxygen as compared to flour from grain of a wild type wheat plant.

5. The wheat flour of claim 1, wherein the flour has at least a 5% reduction in hexanal production as compared to flour from grain of a wild type wheat plant.

6. The wheat flour of claim 1, wherein the flour is selected from the group consisting of: a whole grain flour, an ultrafine milled whole grain flour, a coarse fraction, a bran, and mixtures thereof.

7. The wheat flour of claim 1, wherein the one or more human induced mutations in the Lip1 gene of the A genome comprise a tryptophan to stop codon mutation at amino acid position 122 (W122*) or amino acid position 63 (W63*) of SEQ ID NO:3.

8. The wheat flour of claim 1, wherein the one or more human induced mutations in the Lip1 gene of the D genome comprise a tryptophan to stop codon mutation at amino acid position 62 (W62*) or a tryptophan to stop codon mutation at amino acid position 121 (W121*) of SEQ ID NO:6.

9. The wheat flour of claim 1, wherein the one or more human induced mutations in the Lip1 gene of the A genome comprise a tryptophan to stop codon mutation at amino acid position 122 (W122*) or amino acid position 63 (W63*) of SEQ ID NO:3, and the one or more human induced mutations in the Lip1 gene of the D genome comprise a tryptophan to stop codon mutation at amino acid position 62 (W62*) or a tryptophan to stop codon mutation at amino acid position 121 (W121*) of SEQ ID NO:6.

* * * * *